United States Patent
Radu et al.

(10) Patent No.: US 10,570,124 B2
(45) Date of Patent: Feb. 25, 2020

(54) DEOXYCYTIDINE KINASE BINDING COMPOUNDS

(71) Applicant: THE REGENTS OF THE UNIVERSITY OF CALIFORNIA, Oakland, CA (US)

(72) Inventors: Caius G. Radu, Los Angeles, CA (US); Raymond M. Gipson, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 16/068,658

(22) PCT Filed: Jan. 9, 2017

(86) PCT No.: PCT/US2017/012718
§ 371 (c)(1),
(2) Date: Jul. 6, 2018

(87) PCT Pub. No.: WO2017/120585
PCT Pub. Date: Jul. 13, 2017

(65) Prior Publication Data
US 2019/0016714 A1    Jan. 17, 2019

Related U.S. Application Data

(60) Provisional application No. 62/276,546, filed on Jan. 8, 2016.

(51) Int. Cl.
*C07D 417/12* (2006.01)
*C07D 417/14* (2006.01)
*A61P 35/00* (2006.01)

(52) U.S. Cl.
CPC ............ *C07D 417/12* (2013.01); *A61P 35/00* (2018.01); *C07D 417/14* (2013.01)

(58) Field of Classification Search
CPC ...... C07D 417/12; C07D 417/14; A61P 35/00
USPC ..................................................... 514/210.2
See application file for complete search history.

(56) References Cited

U.S. PATENT DOCUMENTS 8,101,740 B2    1/2012  Radu et al.
2013/0336883 A1    12/2013  Radu et al.

FOREIGN PATENT DOCUMENTS

| WO | WO-2015/023776 A2 | 2/2015 |
| WO | WO-2015/023776 A3 | 2/2015 |
| WO | WO-2016/130581 A2 | 8/2016 |
| WO | WO-2016/130581 A3 | 8/2016 |
| WO | WO-2016/130581 A8 | 8/2016 |

OTHER PUBLICATIONS

Cancer [online], [retrieved on Jul. 6, 2007] Retrieved from the Internet, URL: http://www.nlm.nih.gov/medlineplus/cancer.html (Year: 2007).*
Lala et al., Role of nitric oxide in tumor progression: Lessons from experimental tumors, Cancer and Metastasis Reviews (1998), 17, 91-106 (Year: 1998).*
Golub et al., Molecular Classification of Cancer: Class Discovery and Class Prediction by Gene Expression Monitoring, Science (1999), vol. 286, 531-537 (Year: 1999).*
Boulos, N. et al. (Mar. 31, 2011, e-published Jan. 24, 2011). "Chemotherapeutic agents circumvent emergence of dasatinib-resistant BCR-ABL kinase mutations in a precise mouse model of Philadelphia chromosome-positive acute lymphoblastic leukemia," *Blood* 117(13):3585-3595.
Extended European Search Report dated Jul. 4, 2019, for EP Application No. 17736514.5, 8 pages.
International Search Report dated May 10, 2017, for PCT Application No. PCT/US2017/012718, filed Jan. 9, 2017, 4 pages.
Murphy, J.M. et al. (Sep. 12, 2013, e-published Aug. 15, 2013). "Development of new deoxycytidine kinase inhibitors and noninvasive in vivo evaluation using positron emission tomography," *J Med Chem* 56(17):6696-6708.
Nathanson, D.A. et al. (Mar. 10, 2014, e-published Feb. 24, 2014). "Co-targeting of convergent nucleotide biosynthetic pathways for leukemia eradication," *J Exp Med* 211(3):473-486.
Nomme, J. et al. (Nov. 26, 2014, e-published Nov. 7, 2014). "Structure-guided development of deoxycytidine kinase inhibitors with nanomolar affinity and improved metabolic stability," *J Med Chem* 57(22):9480-9494.
PubChem CID-60202410, located at <https://pubchem.ncbi.nlm.nih.gov/compound/60202410>, create date Oct. 15, 2012, last accessed Apr. 20, 2017, 12 pages.
PubChem CID-60202449, located at <https://pubchem.ncbi.nlm.nih.gov/compound/60202449>, create date Oct. 15, 2012, last accessed Apr. 20, 2017, 8 pages.
Shu, C.J. et al. (Jul. 2010, e-published Jun. 16, 2010). "Novel PET probes specific for deoxycytidine kinase," *J Nucl Med* 51(7):1092-1098.
Written Opinion dated May 10, 2017, for PCT Application No. PCT/US2017/012718, filed Jan. 9, 2017, 5 pages.

* cited by examiner

*Primary Examiner* — Kristin A Vajda
(74) *Attorney, Agent, or Firm* — Mintz Levin Cohn Ferris Glovsky and Popeo, PC; Irina E. Britva

(57) ABSTRACT

There are provided, inter alia, compounds useful for binding to deoxycytidine kinase, and compounds and methods useful to modulate deoxycytidine kinase.

23 Claims, 21 Drawing Sheets

DI-82

(S)-DI-82                (R)-DI-82

1: vehicle
2: DI-82
3: (R)-DI-82
4: Compound 9R

1: vehicle
2: Compound 9R in P9
3: Compound 9R in P9'
4: (R)-DI-82 in P9
5: (R)-DI-82 in P9'

Group 1: Vehicle

Group 2: Compound 9R 25mg/kg

Group 3: Compound 9R 50mg/kg

Group 4: Compound 9R 100mg/kg

DEOXYCYTIDINE KINASE BINDING COMPOUNDS

CROSS-REFERENCES TO RELATED APPLICATIONS

This application is the national stage filing under USC 371 of international application PCT/US2017/012718, filed Jan. 9, 2017, which claims the benefit of U.S. Provisional Application No. 62/276,546, filed Jan. 8, 2016, which are hereby incorporated by reference in their entirety and for all purposes.

STATEMENT AS TO RIGHTS TO INVENTIONS MADE UNDER FEDERALLY SPONSORED RESEARCH AND DEVELOPMENT

This invention was made with Government support under Grant No. CA187678, awarded by the National Institutes of Health. The Government has certain rights in the invention.

BACKGROUND OF THE INVENTION

Deoxycytidine kinase (dCK) is an enzyme which plays a crucial role in role in cellular divisional and which functions in the phosphorylation of several deoxyribonucleosides and their nucleoside analogs. Deoxycytidine kinase is observed to be predominantly expressed in hematopoietic tissues and is unregulated in certain solid tumors. dCK deficiency is also associated with certain forms of resistance to antiviral and anticancer chemotherapeutic agents. dCK is a clinically important polypeptide target because of, for example, its role in cellular divisional, as well as its association with drug resistance and/or drug sensitivity. Compounds and compositions that bind to and inhibit dCK activities in vivo are desirable for the treatment of diseases and disorders where dCK activity is implicated.

BRIEF SUMMARY OF THE INVENTION

This disclosure provides, for example, compounds and compositions which are modulators of deoxycytidine kinase (dCK), and their use as medicinal agents, processes for their preparation, and pharmaceutical compositions that include disclosed compounds as at least one active ingredient. The disclosure also provides for the use of disclosed compounds as medicaments and/or in the manufacture of medicaments for the inhibition of deoxycytidine kinase (dCK) activity in warm-blooded animals such as humans.

In one aspect, provided herein are compounds of Formula (I), or a pharmaceutically acceptable salt or solvate thereof:

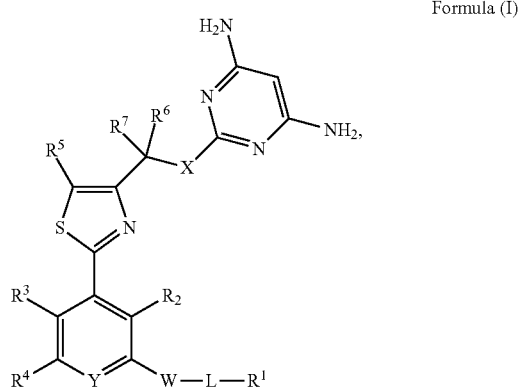

Formula (I)

wherein W is —O—, —S—, or —N($R^8$)—; L is optionally substituted alkylene, optionally substituted alkenylene, or optionally substituted alkynylene; X is —$CH_2$—, —O—, —N($R^8$)—, —S—, —S(O)—, or —S(O)$_2$—; Y is N or C($R^9$); $R^1$ is optionally substituted heterocycloalkyl; $R^2$, $R^3$, $R^4$ are independently hydrogen, halogen, —CN, —$N_3$, —$CF_3$, —$CCl_3$, —$CBr_3$, —$CI_3$, —CN, —C(O)H, —OH, —$NH_2$, —C(O)OH, —C(O)$NH_2$, —$NO_2$, —SH, optionally substituted alkyl, optionally substituted heteroalkyl, optionally substituted heterocycloalkyl, optionally substituted aryl, optionally substituted heteroaryl, optionally substituted alkoxy, or optionally substituted cycloalkyl; $R^5$ is hydrogen, halogen, —CN, —$N_3$, —$CF_3$, —$CCl_3$, —$CBr_3$, —$CI_3$, —CN, —C(O)H, —OH, —$NH_2$, —C(O)OH, —C(O)$NH_2$, —$NO_2$, —SH, optionally substituted alkyl, optionally substituted heteroalkyl, optionally substituted heterocycloalkyl, optionally substituted alkoxy, optionally substituted cycloalkyl, optionally substituted aryl, or optionally substituted heteroaryl; $R^6$ and $R^7$ are independently hydrogen, halogen, or optionally substituted alkyl; or $R^6$ and $R^7$ are taken together with the carbon to which they are attached to form a cycloalkyl; $R^8$ is hydrogen or optionally substituted alkyl; and $R^9$ is hydrogen, halogen, —CN, —$N_3$, —$CF_3$, —$CCl_3$, —$CBr_3$, —$CI_3$, —CN, —C(O)H, —OH, —$NH_2$, —C(O)OH, —C(O)$NH_2$, —$NO_2$, —SH, optionally substituted alkyl, optionally substituted heteroalkyl, optionally substituted heterocycloalkyl, optionally substituted aryl, optionally substituted heteroaryl, optionally substituted alkoxy, or optionally substituted cycloalkyl.

In some embodiments is a compound of Formula (I), wherein $R^2$ and $R^3$ are hydrogen. In some embodiments is a compound of Formula (I), wherein $R^4$ is hydrogen or halogen. In some embodiments is a compound of Formula (I), wherein $R^4$ is hydrogen. In some embodiments is a compound of Formula (I), wherein $R^6$ and $R^7$ are independently hydrogen or optionally substituted alkyl. In some embodiments is a compound of Formula (I), wherein $R^7$ is hydrogen.

In some embodiments is a compound of Formula (I), wherein the compound of Formula (I) is a compound of Formula (Ia):

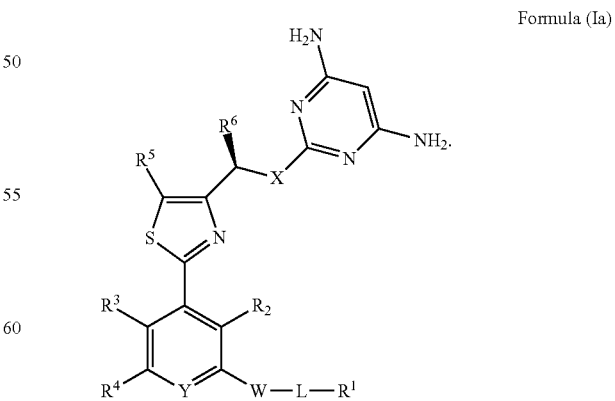

Formula (Ia)

In some embodiments is a compound of Formula (I), wherein the compound of Formula (I) is a compound of Formula (Ib):

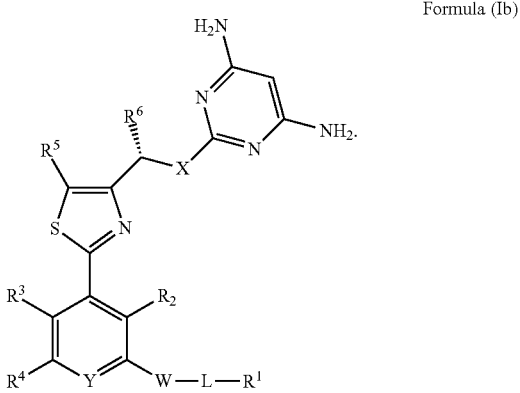

Formula (Ib)

In some embodiments is a compound of Formula (I), wherein $R^6$ is optionally substituted alkyl. In some embodiments is a compound of Formula (I), wherein $R^6$ is methyl, ethyl, or propyl. In some embodiments is a compound of Formula (I), wherein $R^6$ is methyl. In some embodiments is a compound of Formula (I), wherein $R^6$ and $R^7$ are not both hydrogen. In some embodiments is a compound of Formula (I), wherein $R^6$ and $R^7$ are taken together with the carbon to which they are attached to form a cycloalkyl. In some embodiments is a compound of Formula (I), wherein $R^5$ is optionally substituted alkyl. In some embodiments is a compound of Formula (I), wherein $R^5$ is methyl, ethyl, propyl, or butyl. In some embodiments is a compound of Formula (I), wherein $R^5$ is methyl. In some embodiments is a compound of Formula (I), wherein X is —S—. In some embodiments is a compound of Formula (I), wherein X is —CH$_2$—. In some embodiments is a compound of Formula (I), wherein Y is N. In some embodiments is a compound of Formula (I), wherein Y is C($R^9$). In some embodiments is a compound of Formula (I), wherein $R^9$ is hydrogen, optionally substituted alkyl, or optionally substituted alkoxy. In some embodiments is a compound of Formula (I), wherein $R^9$ is optionally substituted alkoxy. In some embodiments is a compound of Formula (I), wherein $R^9$ is methoxy, ethoxy, or propoxy. In some embodiments is a compound of Formula (I), wherein $R^9$ is methoxy. In some embodiments is a compound of Formula (I), wherein W is —O—. In some embodiments is a compound of Formula (I), wherein L is optionally substituted alkylene. In some embodiments is a compound of Formula (I), wherein L is —CH$_2$CH$_2$—. In some embodiments is a compound of Formula (I), wherein $R^1$ is a 5-membered optionally substituted heterocycloalkyl. In some embodiments is a compound of Formula (I), wherein $R^1$ is pyrrolidinyl. In some embodiments is a compound of Formula (I), wherein $R^1$ is a 6-membered optionally substituted heterocycloalkyl. In some embodiments is a compound of Formula (I), wherein $R^1$ is piperidinyl, piperizanyl, or morpholinyl. In some embodiments is a compound of Formula (I), wherein $R^1$ is morpholinyl.

In another aspect, provided herein is a pharmaceutical composition comprising a compound disclosed herein or a pharmaceutically acceptable salt or solvate thereof, and a pharmaceutically acceptable excipient.

In another aspect, provided herein is a method for inhibiting a deoxycytidine kinase (dCK) activity comprising contacting a deoxycytidine kinase with an effective amount of a compound disclosed herein thereby inhibiting said deoxycytidine kinase.

In another aspect, provided herein is a method of treating cancer in a subject in need thereof, comprising administering to the subject an effective amount of a compound disclosed herein.

In another aspect, provided herein is a method of treating cancer in a subject in need thereof, comprising administering to the subject a pharmaceutical composition disclosed herein.

In some embodiments, the cancer is a solid tumor cancer. In some embodiments, the solid tumor cancer is ovarian cancer, pancreatic cancer, lung cancer, glioblastoma, hepatocellular carcinoma, breast cancer, prostate cancer or head and neck cancer. In some embodiments, the cancer is a liquid tumor cancer. In some embodiments, the liquid tumor cancer is a blood cancer. In some embodiments, the cancer is leukemia or lymphoma.

DETAILED DESCRIPTION OF THE INVENTION

Definitions

Figure 1:
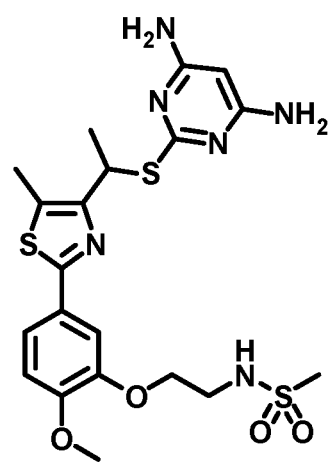
FIG. 1 shows the chemical structures of N-(2-(5-(4-(1-(4,6-diaminopyrimidin-2-ylthio)ethyl)-5-methylthiazol-2-yl)-2-methoxyphenoxy)ethyl)methanesulfonamide (DI-82), (R)—N-(2-(5-(4-(1-(4,6-diaminopyrimidin-2-ylthio)ethyl)-5-methylthiazol-2-yl)-2-methoxyphenoxy)ethyl)methanesulfonamide ((R)-DI-82), and (S)—N-(2-(5-(4-(1-(4,6-diaminopyrimidin-2-ylthio)ethyl)-5-methylthiazol-2-yl)-2-methoxyphenoxy)ethyl)methanesulfonamide ((S)-DI-82).
Figure 1:
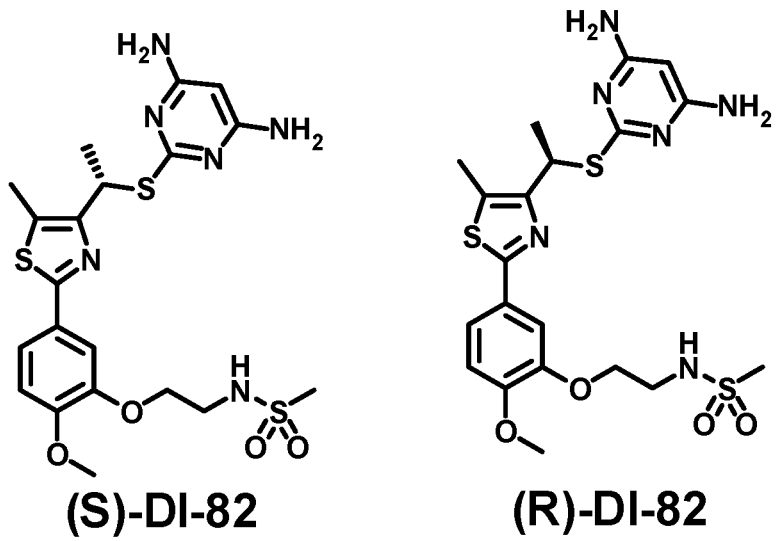

The term "alkyl" refers to and includes linear or branched univalent hydrocarbon structures and combination thereof, which may be fully saturated, mono- or polyunsaturated, having the number of carbon atoms designated (i.e., $C_1$-$C_{10}$ means one to ten carbons). Particular alkyl groups are those having 1 to 20 carbon atoms (a "$C_1$-$C_{20}$ alkyl"). More particular alkyl groups are those having 1 to 8 carbon atoms (a "$C_1$-$C_8$ alkyl"), 3 to 8 carbon atoms (a "$C_3$-$C_8$ alkyl"), 1 to 6 carbon atoms (a "$C_1$-$C_6$ alkyl"), 1 to 5 carbon atoms (a "$C_1$-$C_5$ alkyl"), or 1 to 4 carbon atoms (a "$C_1$-$C_4$ alkyl"). Examples of saturated hydrocarbon radicals include, but are not limited to, groups such as methyl, ethyl, n-propyl, isopropyl, n-butyl, t-butyl, isobutyl, sec-butyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. Examples of saturated $C_1$-$C_4$ alkyl include methyl ($CH_3$), ethyl ($C_2H_5$), propyl ($C_3H_7$) and butyl ($C_4H_9$). Examples of saturated $C_1$-$C_6$ alkyl include methyl ($CH_3$), ethyl ($C_2H_5$), propyl ($C_3H_7$), butyl ($C_4H_9$), pentyl ($C_5H_{11}$) and hexyl ($C_6H_{13}$).

An alkyl group may be substituted (i.e., one or more hydrogen atoms are replaced with univalent or divalent radicals) with one more substituents, such as radicals described herein, for example, fluoro, chloro, bromo, iodo, hydroxyl, alkoxy, thio, amino, acylamino, alkoxycarbonylamido, carboxyl, acyl, alkoxycarbonyl, sulfonyl, cycloalkyl, aryl, heterocyclyl and herteroaryl, and other functional groups known in the art. A "perfluoroalkyl" refers to an alkyl group where every hydrogen atom is replaced with a fluorine atom. Examples of saturated $C_1$-$C_6$ perfluoroalkyl include trifluoromethyl ($CF_3$), pentafluoroethyl ($C_2F_5$), heptafluoropropyl ($C_3F_7$), nonafluorobutyl ($C_4F_9$), undecafluoropentyl ($C_5F_{11}$) and tridecafluorohexyl ($C_6F_{13}$).

The term "alkoxy" refers to a radical bonded through an oxygen atom of the formula —O-alkyl, where alkyl is an alkyl chain as defined above.

The term "alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, n-butylene, and the like. The alkylene chain is attached to the rest of the molecule through a single bond and to the radical group through a single bond. In some embodiments, the points of attachment of the alkylene chain to the rest of the molecule and to the radical group are through one carbon in the alkylene chain or through any two carbons within the chain. In certain embodiments, an alkylene comprises one to eight carbon atoms (e.g., $C_1$-$C_8$ alkylene). In other embodiments, an alkylene comprises one to five carbon atoms (e.g., $C_1$-$C_5$ alkylene). In other embodiments, an alkylene comprises one to four carbon atoms (e.g., $C_1$-$C_4$ alkylene). In other embodiments, an alkylene comprises one to three carbon atoms (e.g., $C_1$-$C_3$ alkylene). In other embodiments, an alkylene comprises one to two carbon atoms (e.g., $C_1$-$C_2$ alkylene). In other embodiments, an alkylene comprises one carbon atom (e.g., alkylene). In other embodiments, an alkylene comprises five to eight carbon atoms (e.g., $C_5$-$C_8$ alkylene). In other embodiments, an alkylene comprises two to five carbon atoms (e.g., $C_2$-$C_5$ alkylene). In other embodiments, an alkylene comprises three to five carbon atoms (e.g., $C_3$-$C_5$ alkylene). The term "alkenylene" refers to an alkylene also having at least one double bond. The term "alkynylene" refers to an alkylene also having at least one triple bond.

An alkylene group may be substituted (i.e., one or more hydrogen atoms are replaced with univalent or divalent radicals) with one more substituents, such as radicals described herein, for example, fluoro, chloro, bromo, iodo, hydroxyl, alkoxy, thio, amino, acylamino, alkoxycarbonylamido, carboxyl, acyl, alkoxycarbonyl, sulfonyl, cycloalkyl, aryl, heterocyclyl and herteroaryl, and other functional groups known in the art.

The term "cycloalkyl" refers to and includes cyclic univalent hydrocarbon structures, which may be fully saturated, mono- or polyunsaturated, having the number of carbon atoms designated (i.e., $C_1$-$C_{10}$ means one to ten carbons). Cycloalkyl can consist of one ring, such as cyclohexyl, or multiple rings, such as adamantly, but excludes aryl groups. A cycloalkyl comprising more than one ring may be fused, spiro or bridged, or combinations thereof. A preferred cycloalkyl is a cyclic hydrocarbon having from 3 to 13 annular carbon atoms. A more preferred cycloalkyl is a cyclic hydrocarbon having from 3 to 8 annular carbon atoms (a "$C_3$-$C_8$ cycloalkyl"). Examples of cycloalkyl include, but are not limited to, cyclopropyl, cyclobutyl, cyclopentyl, cyclohexyl, 1-cyclohexenyl, 3-cyclohexenyl, cycloheptyl, norbornyl, and the like.

The term "heterocycle" or "heterocyclyl" or "heterocycloalkyl" refers to a saturated or an unsaturated non-aromatic group having from 1 to 10 annular carbon atoms and from 1 to 4 annular heteroatoms, such as nitrogen, sulfur or oxygen, and the like, wherein the nitrogen and sulfur atoms are optionally oxidized, and the nitrogen atom(s) are optionally quaternized. A heterocyclyl group may have a single ring or multiple condensed rings, but excludes heteroaryl groups. A heterocycle comprising more than one ring may be fused, spiro or bridged, or any combination thereof. In fused ring systems, one or more of the fused rings can be aryl or heteroaryl. Examples of heterocyclyl groups include, but are not limited to, tetrahydropyranyl, dihydropyranyl, piperidinyl, morpholinyl, piperazinyl, pyrrolidinyl, thiazolinyl, thiazolidinyl, tetrahydrofuranyl, tetrahydrothiophenyl, 2,3-dihydrobenzo[b]thiophen-2-yl, 4-amino-2-oxopyrimidin-1(2H)-yl, and the like.

The term "aryl" refers to and includes polyunsaturated aromatic hydrocarbon substituents. Aryl may contain additional fused rings (e.g., from 1 to 3 rings), including additionally fused aryl, heteroaryl, cycloalkyl, and/or heterocyclyl rings. In one variation, the aryl group contains from 6 to 14 annular carbon atoms. Examples of aryl groups include, but are not limited to, phenyl, naphthyl, biphenyl, and the like.

The term "heteroaryl" refers to and includes unsaturated aromatic cyclic groups having from 1 to 10 annular carbon atoms and at least one annular heteroatom, including but not limited to heteroatoms such as nitrogen, oxygen and sulfur, wherein the nitrogen and sulfur atoms are optionally oxidized, and the nitrogen atom(s) are optionally quaternized. A heteroaryl group can be attached to the remainder of the molecule at an annular carbon or annular heteroatom. Heteroaryl may contain additional fused rings (e.g., from 1 to 3 rings), including additionally fused aryl, heteroaryl, cycloalkyl, and/or heterocyclyl rings. Examples of heteroaryl groups include, but are not limited to, pyridyl, pyrimidyl, thiophenyl, furanyl, thiazolyl, and the like.

Cycloalkyl, aryl, heterocycloalkyl and heteroaryl groups may also be substituted with one or more substituents, such as radicals detailed herein, for example, fluoro, chloro, bromo, iodo, hydroxyl, alkoxy, thio, amino, acylamino, alkoxycarbonylamido, carboxyl, acyl, alkoxycarbonyl, sulfonyl, alkyl, cycloalkyl, aryl, heterocyclyl and herteroaryl, and other functional groups known in the art.

In embodiments, where a moiety is optionally substituted, the moiety is optionally substituted with a substituent group. A "substituent group," as used herein, means a group selected from the following moieties:

(A) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O) NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:

(i) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected from:

(a) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O) NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, or heteroaryl, substituted with at least one substituent selected from: oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O) NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, and unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, and each substituted or unsubstituted heterocycloalkyl is a substituted or unsubstituted 3 to 8 membered heterocycloalkyl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, and each substituted or unsubstituted heterocycloalkyl is a substituted or unsubstituted 3 to 7 membered heterocycloalkyl.

In some embodiments, each substituted group described in the compounds herein is substituted with at least one substituent group. Each substituent groups is optimally different. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, and/or each substituted or unsubstituted heterocycloalkyl is a substituted or unsubstituted 3 to 8 membered heterocycloalkyl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, and/or each substituted or unsubstituted heterocycloalkylene is a substituted or unsubstituted 3 to 8 membered heterocycloalkylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, and/or each substituted or unsubstituted heterocycloalkyl is a substituted or unsubstituted 3 to 7 membered heterocycloalkyl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, and/or each substituted or unsubstituted heterocycloalkylene is a substituted or unsubstituted 3 to 7 membered heterocycloalkylene.

Certain compounds described herein possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the (R) and (S) configurations for each asymmetric center. Therefore, single stereochemical isomers as well as enantiomeric and diastereomeric mixtures of the present compounds, generally recognized as stable by those skilled in the art, are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, replacement of fluoride by $^{18}F$, or the replacement of a carbon by $^{13}C$- or $^{14}C$-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^3H$), fluoride ($^{18}F$), iodine-125 ($^{125}I$), or carbon-14 ($^{14}C$). All isotopic variations of the compounds of the present invention, whether radioactive or not, are encompassed within the scope of the present invention.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative, such as those known in the art, for example, described in Remington's Pharmaceutical Sciences 16th edition, Osol, A. Ed. (1980).

As used herein, "treatment" or "treating" is an approach for obtaining beneficial or desired results including and preferably clinical results. For example, beneficial or desired clinical results include, but are not limited to, one or more of the following: decreasing symptoms resulting from the disease, increasing the quality of life of those suffering from the disease, decreasing the dose of other medications required to treat the disease, delaying the progression of the disease, and/or prolonging survival of individuals.

As used herein, "delaying development of a disease" means to defer, hinder, slow, retard, stabilize, and/or postpone development of the disease (such as cancer). This delay can be of varying lengths of time, depending on the history of the disease and/or individual being treated. As is evident to one skilled in the art, a sufficient or significant delay can, in effect, encompass prevention, in that the individual does not develop the disease. For example, a late stage cancer, such as development of metastasis, may be delayed.

As used herein, an "effective dosage" or "effective amount" of drug, compound, or pharmaceutical composition is an amount sufficient to effect beneficial or desired results. For prophylactic use, beneficial or desired results include results such as eliminating or reducing the risk, lessening the severity, or delaying the onset of the disease, including biochemical, histological and/or behavioral symptoms of the disease, its complications and intermediate pathological phenotypes presenting during development of the disease. For therapeutic use, beneficial or desired results include clinical results such as decreasing one or more symptoms resulting from the disease, increasing the quality of life of those suffering from the disease, decreasing the dose of other medications required to treat the disease, enhancing effect of another medication such as via targeting, delaying the progression of the disease, and/or prolonging survival. In the case of cancer or tumor, an effective amount of the drug may have the effect in reducing the number of cancer cells; reducing the tumor size; inhibiting (i.e., slow to some extent and preferably stop) cancer cell infiltration into peripheral organs; inhibit (i.e., slow to some extent and preferably stop) tumor metastasis; inhibiting, to some extent, tumor growth; and/or relieving to some extent one or more of the symptoms associated with the disorder. An effective dosage can be administered in one or more administrations. For purposes of this invention, an effective dosage of drug, compound, or pharmaceutical composition is an amount sufficient to accomplish prophylactic or therapeutic treatment either directly or indirectly. As is understood in the clinical context, an effective dosage of a drug, compound, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved.

As defined herein, the term "inhibition", "inhibit", "inhibiting" and the like in reference to a protein-inhibitor inter-action means negatively affecting (e.g. decreasing) the activity or function of the protein relative to the activity or function of the protein in the absence of the inhibitor. Inhibition may refer to reduction of a disease or symptoms of disease. Inhibition may refer to a reduction in the activity of a particular protein or nucleic acid target. The protein may be deoxycytidine kinase. Thus, inhibition includes, at least in part, partially or totally blocking stimulation, decreasing, preventing, or delaying activation, or inactivating, desensitizing, or down-regulating signal transduction or enzymatic activity or the amount of a protein.

The term "modulator" refers to a composition that increases or decreases the level of a target molecule or the function of a target molecule or the physical state of the target of the molecule.

The term "modulate" is used in accordance with its plain ordinary meaning and refers to the act of changing or varying one or more properties. "Modulation" refers to the process of changing or varying one or more properties. For example, a modulator of a target protein changes by increasing or decreasing a property or function of the target molecule or the amount of the target molecule. A modulator of a disease decreases a symptom, cause, or characteristic of the targeted disease.

"Selective" or "selectivity" or the like of a compound refers to the compound's ability to discriminate between molecular targets. "Specific", "specifically", "specificity", or the like of a compound refers to the compound's ability to cause a particular action, such as inhibition, to a particular molecular target with minimal or no action to other proteins in the cell.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "administering" means oral administration, administration as a suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

By "co-administer" it is meant that a compound described herein is administered at the same time, just prior to, or just after the administration of one or more additional therapies, for example, an anticancer agent as described herein. The compounds described herein can be administered alone or can be co-administered to the patient. Co-administration is meant to include simultaneous or sequential administration of the compound individually or in combination (more than one compound or agent). Thus, the preparations can also be combined, when desired, with other active substances (e.g. anticancer agents).

Co-administration includes administering one active agent (e.g. a complex described herein) within 0.5, 1, 2, 4, 6, 8, 10, 12, 16, 20, or 24 hours of a second active agent (e.g. anti-cancer agents). Also contemplated herein, are embodiments, where co-administration includes administering one active agent within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. Co-administration can be accomplished by co-formulation, i.e., preparing a single pharmaceutical composition including both active agents. In other embodiments, the active agents can be formulated separately. In some embodiments, the active and/or adjunctive agents are linked or conjugated to one another. In some embodiments, the compounds described herein are combined with treatments for cancer such as chemotherapy or radiation therapy.

The term "associated" or "associated with" in the context of a substance or substance activity or function associated with a disease means that the disease is caused by (in whole or in part), a symptom of the disease is caused by (in whole or in part) the substance or substance activity or function, or a side-effect of the compound (e.g. toxicity) is caused by (in whole or in part) the substance or substance activity or function.

"Patient," "subject," "patient in need thereof," and "subject in need thereof" are herein used interchangeably and refer to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In some embodiments, a patient is human. A "cancer-patient" is a patient suffering from, or prone to developing cancer.

Unless clearly indicated otherwise, the term "individual" as used herein refers to a mammal, including but not limited to, bovine, horse, feline, rabbit, canine, rodent, or primate (e.g., human). In some embodiments, an individual is a human. In some embodiments, an individual is a non-human primate such as chimpanzees and other apes and monkey species. In some embodiments, an individual is a farm animal such as cattle, horses, sheep, goats and swine; pets such as rabbits, dogs and cats; laboratory animals including rodents, such as rats, mice, and guinea pigs; and the like. In some embodiments, the invention find use in both human medicine and in the veterinary context.

"Disease" or "condition" refer to a state of being or health status of a patient or subject capable of being treated with the compounds or methods provided herein. In some embodiments, the disease as used herein refers to cancer.

"Chemotherapeutic" or "chemotherapeutic agent" is used in accordance with its plain ordinary meaning and refers to a chemical composition or compound having antineoplastic properties or the ability to inhibit the growth or proliferation of cells.

"Cancer model organism", as used herein, is an organism exhibiting a phenotype indicative of cancer, or the activity of cancer causing elements, within the organism. The term cancer is defined above. A wide variety of organisms may serve as cancer model organisms, and include for example, cancer cells and mammalian organisms such as rodents (e.g. mouse or rat) and primates (such as humans). Cancer cell lines are widely understood by those skilled in the art as cells exhibiting phenotypes or genotypes similar to in vivo cancers. Cancer cell lines as used herein includes cell lines from animals (e.g. mice) and from humans.

As used herein and in the appended claims, the singular forms "a," "an," and "the" include plural reference unless the context clearly indicates otherwise.

It is understood that aspect and variations of the invention described herein include "consisting" and/or "consisting essentially of" aspects and variations.

Compounds

In one aspect, provided herein are compounds of Formula (I), or a pharmaceutically acceptable salt or solvate thereof:

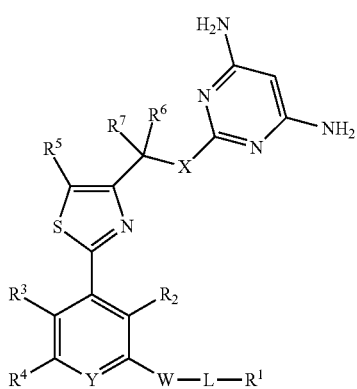

Formula (I)

wherein:
W is —O—, —S—, or —N($R^8$)—;
L is optionally substituted alkylene, optionally substituted alkenylene, or optionally substituted alkynylene;
X is —$CH_2$—, —O—, —N($R^8$)—, —S—, —S(O)—, or —S(O)$_2$—; Y is N or C($R^9$);
$R^1$ is optionally substituted heterocycloalkyl;
$R^2$, $R^3$, $R^4$ are independently hydrogen, halogen, —CN, optionally substituted alkyl, optionally substituted alkoxy, or optionally substituted cycloalkyl;
$R^5$ is hydrogen, halogen, optionally substituted alkyl, optionally substituted alkoxy, optionally substituted cycloalkyl, optionally substituted aryl, or optionally substituted heteroaryl;
$R^6$ and $R^7$ are independently hydrogen, halogen, or optionally substituted alkyl; or
$R^6$ and $R^7$ are taken together with the carbon to which they are attached to form a cycloalkyl;
$R^8$ is hydrogen or optionally substituted alkyl; and $R^9$ is hydrogen, halogen, —CN, optionally substituted alkyl, optionally substituted alkoxy, or optionally substituted cycloalkyl.

In some embodiment is a compound of Formula (I), wherein $R^2$ and $R^3$ are hydrogen. In some embodiments is a compound of Formula (I), wherein $R^2$ and $R^3$ are independently hydrogen or halogen. In some embodiments is a compound of Formula (I), wherein $R^2$ and $R^3$ are independently hydrogen or optionally substituted alkyl. In some embodiments is a compound of Formula (I), wherein $R^2$ and $R^3$ are independently hydrogen or unsubstituted alkyl.

In some embodiments is a compound of Formula (I), wherein $R^4$ is hydrogen or halogen. In some embodiments is a compound of Formula (I), wherein $R^4$ is hydrogen.

In some embodiments is a compound of Formula (I), wherein $R^6$ and $R^7$ are independently hydrogen or optionally substituted alkyl. In some embodiments is a compound of Formula (I), wherein $R^6$ and $R^7$ are independently hydrogen or unsubstituted alkyl. In some embodiments is a compound of Formula (I), wherein $R^7$ is hydrogen.

In some embodiments is a compound of Formula (I), wherein the compound of Formula (I) is a compound of Formula (Ia):

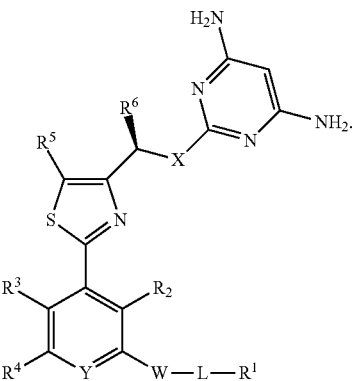

Formula (Ia)

In some embodiments is a compound of Formula (I), wherein the compound of Formula (I) is a compound of Formula (Ib):

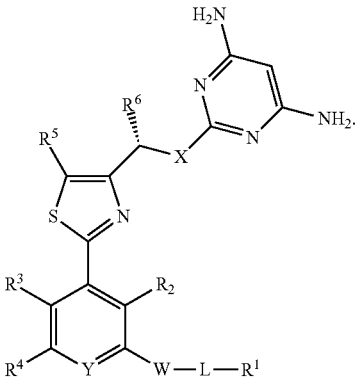

Formula (Ib)

In some embodiments is a compound of Formula (I), wherein $R^6$ is optionally substituted alkyl. In some embodiments is a compound of Formula (I), wherein $R^6$ is unsubstituted alkyl. In some embodiments is a compound of Formula (I), wherein $R^6$ is substituted alkyl. In some embodiments is a compound of Formula (I), wherein $R^6$ is methyl, ethyl, or propyl. In some embodiments is a compound of Formula (I), wherein $R^6$ is methyl. In some embodiments is a compound of Formula (I), wherein $R^6$ and $R^7$ are not both hydrogen. In some embodiments is a compound of Formula (I), wherein $R^6$ and $R^7$ are both optionally substituted alkyl. In some embodiments is a compound of Formula (I), wherein $R^6$ and $R^7$ are both unsubstituted alkyl. In some embodiments is a compound of Formula (I), wherein $R^6$ and $R^7$ are both methyl. In some embodiments is a compound of Formula (I), wherein $R^6$ and $R^7$ are both unsubstituted alkyl. In some embodiments is a compound of Formula (I), wherein $R^6$ and $R^7$ are taken together with the carbon to which they are attached to form a cycloalkyl. In some embodiments is a compound of Formula (I), wherein $R^6$ and $R^7$ are taken together with the carbon to which they are attached to form a cyclopropyl, cyclobutyl, cyclopentyl, or cyclohexyl. In some embodiments is a compound of Formula (I), wherein $R^6$ and $R^7$ are taken together with the carbon to which they are attached to form a cyclopropyl.

In some embodiments is a compound of Formula (I), wherein $R^5$ is optionally substituted alkyl. In some embodiments is a compound of Formula (I), wherein $R^5$ is substituted alkyl. In some embodiments is a compound of Formula (I), wherein $R^5$ is unsubstituted alkyl. In some embodiments is a compound of Formula (I), wherein $R^5$ is methyl, ethyl, propyl, or butyl. In some embodiments is a compound of Formula (I), wherein $R^5$ is methyl. In some embodiments is a compound of Formula (I), wherein $R^5$ is ethyl. In some embodiments is a compound of Formula (I), wherein $R^5$ is propyl.

In some embodiments is a compound of Formula (I), wherein $R^5$ is optionally substituted aryl. In some embodiments is a compound of Formula (I), wherein $R^5$ is substituted aryl. In some embodiments is a compound of Formula (I), wherein $R^5$ is unsubstituted aryl. In some embodiments is a compound of Formula (I), wherein $R^5$ is phenyl.

In some embodiments is a compound of Formula (I), wherein X is —S—. In some embodiments is a compound of Formula (I), wherein X is —CH$_2$—. In some embodiments is a compound of Formula (I), wherein X is —N(R$^8$)—. In some embodiments is a compound of Formula (I), wherein X is —N(R$^8$)— and $R^8$ is hydrogen. In some embodiments is a compound of Formula (I), wherein X is —N(R$^8$)— and $R^8$ is optionally substituted alkyl. In some embodiments is a compound of Formula (I), wherein X is —N(R$^8$)— and $R^8$ is substituted alkyl. In some embodiments is a compound of Formula (I), wherein X is —N(R$^8$)— and $R^8$ is unsubstituted alkyl. In some embodiments is a compound of Formula (I), wherein X is —S(O)—. In some embodiments is a compound of Formula (I), wherein X is —S(O)$_2$—. In some embodiments is a compound of Formula (I), wherein X is —O—.

In some embodiments is a compound of Formula (I), wherein Y is N. In some embodiments is a compound of Formula (I), wherein Y is C(R$^9$). In some embodiments is a compound of Formula (I), wherein Y is C(R$^9$) and $R^9$ is hydrogen, optionally substituted alkyl, or optionally substituted alkoxy. In some embodiments is a compound of Formula (I), wherein Y is C(R$^9$) and $R^9$ is hydrogen. In some embodiments is a compound of Formula (I), wherein Y is C(R$^9$) and $R^9$ is optionally substituted alkyl. In some embodiments is a compound of Formula (I), wherein Y is C(R$^9$) and $R^9$ is substituted alkyl. In some embodiments is a compound of Formula (I), wherein Y is C(R$^9$) and $R^9$ is —CF$_3$. In some embodiments is a compound of Formula (I), wherein Y is C(R$^9$) and $R^9$ is unsubstituted alkyl. In some embodiments is a compound of Formula (I), wherein Y is C(R$^9$) and $R^9$ is methyl, ethyl, or propyl.

In some embodiments is a compound of Formula (I), wherein Y is C(R$^9$) and $R^9$ is optionally substituted alkoxy. In some embodiments is a compound of Formula (I), wherein Y is C(R$^9$) and $R^9$ is substituted alkoxy. In some embodiments is a compound of Formula (I), wherein Y is C(R$^9$) and $R^9$ is —O—(CH$_2$CH$_2$—O)$_n$—CH$_3$ wherein n is an integer between 0 and 6. In some embodiments is a compound of Formula (I), wherein Y is C(R$^9$) and $R^9$ is —O—(CH$_2$CH$_2$—O)$_n$—CH$_3$ wherein n is 2. In some embodiments is a compound of Formula (I), wherein Y is C(R$^9$) and $R^9$ is O—(CH$_2$CH$_2$—O)$_n$—CH$_3$ wherein n is 3. In some embodiments is a compound of Formula (I), wherein Y is C(R$^9$) and $R^9$ is —O—(CH$_2$CH$_2$—O)$_n$—CH$_3$ wherein n is 4. In some embodiments is a compound of Formula (I), wherein Y is C(R$^9$) and $R^9$ is —O—(CH$_2$CH$_2$—O)$_n$—CH$_3$ wherein n is 5. In some embodiments is a compound of Formula (I), wherein Y is C(R$^9$) and $R^9$ is —O—(CH$_2$CH$_2$—O)$_n$—CH$_3$ wherein n is 6.

In some embodiments is a compound of Formula (I), wherein Y is C(R$^9$) and $R^9$ is unsubstituted alkoxy. In some embodiments is a compound of Formula (I), wherein Y is C(R$^9$) and $R^9$ is methoxy, ethoxy, or propoxy. In some embodiments is a compound of Formula (I), wherein Y is C(R$^9$) and $R^9$ is methoxy.

In some embodiments is a compound of Formula (I), wherein W is —O—. In some embodiments is a compound of Formula (I), wherein W is —S—. In some embodiments is a compound of Formula (I), wherein W is —N(R$^8$)—. In some embodiments is a compound of Formula (I), wherein W is —N(R$^8$)— and $R^8$ is hydrogen. In some embodiments is a compound of Formula (I), wherein W is —N(R$^8$)— and $R^8$ is optionally substituted alkyl. In some embodiments is a compound of Formula (I), wherein W is —N(R$^8$)— and $R^8$ is substituted alkyl. In some embodiments is a compound of Formula (I), wherein W is —N(R$^8$)— and $R^8$ is unsubstituted alkyl. In some embodiments is a compound of Formula (I), wherein W is —N(R$^8$)— and $R^8$ is methyl, ethyl or propyl.

In some embodiments is a compound of Formula (I), wherein L is optionally substituted alkylene. In some embodiments is a compound of Formula (I), wherein L is substituted alkylene. In some embodiments is a compound of Formula (I), wherein L is unsubstituted alkylene. In some embodiments is a compound of Formula (I), wherein L is —CH$_2$CH$_2$—. In some embodiments is a compound of Formula (I), wherein L is —CH$_2$CH$_2$CH$_2$—. In some embodiments is a compound of Formula (I), wherein L is —CH$_2$CH$_2$CH$_2$CH$_2$—.

In some embodiments is a compound of Formula (I), wherein L is optionally substituted alkenylene. In some embodiments is a compound of Formula (I), wherein L is substituted alkenylene. In some embodiments is a compound of Formula (I), wherein L is unsubstituted alkenylene. In some embodiments is a compound of Formula (I), wherein L is —CH$_2$=CH$_2$—.

In some embodiments is a compound of Formula (I), wherein L is optionally substituted alkynylene. In some embodiments is a compound of Formula (I), wherein L is substituted alkynylene. In some embodiments is a compound of Formula (I), wherein L is unsubstituted alkynylene. In some embodiments is a compound of Formula (I), wherein L is —CH$_2$=CH$_2$—.

In some embodiments is a compound of Formula (I), wherein R¹ is a 3-membered optionally substituted heterocycloalkyl. In some embodiments is a compound of Formula (I), wherein R¹ is a 3-membered substituted heterocycloalkyl. In some embodiments is a compound of Formula (I), wherein R¹ is a 3-membered unsubstituted heterocycloalkyl. In some embodiments is a compound of Formula (I), wherein R¹ is azyridinyl.

In some embodiments is a compound of Formula (I), wherein R¹ is a 4-membered optionally substituted heterocycloalkyl. In some embodiments is a compound of Formula (I), wherein R¹ is a 4-membered substituted heterocycloalkyl. In some embodiments is a compound of Formula (I), wherein R¹ is a 4-membered unsubstituted heterocycloalkyl. In some embodiments is a compound of Formula (I), wherein R¹ is azetidinyl.

In some embodiments is a compound of Formula (I), wherein R¹ is a 5-membered optionally substituted heterocycloalkyl. In some embodiments is a compound of Formula (I), wherein R¹ is a 5-membered substituted heterocycloalkyl. In some embodiments is a compound of Formula (I), wherein R¹ is a 5-membered unsubstituted heterocycloalkyl. In some embodiments is a compound of Formula (I), wherein R¹ is pyrrolidinyl.

In some embodiments is a compound of Formula (I), wherein R¹ is a 6-membered optionally substituted heterocycloalkyl. In some embodiments is a compound of Formula (I), wherein R¹ is a 6-membered substituted heterocycloalkyl. In some embodiments is a compound of Formula (I), wherein R¹ is a 6-membered unsubstituted heterocycloalkyl. In some embodiments is a compound of Formula (I), wherein R¹ is piperidinyl, piperizanyl, or morpholinyl. In some embodiments is a compound of Formula (I), wherein R¹ is morpholinyl. In some embodiments is a compound of Formula (I), wherein R¹ is piperidinyl. In some embodiments is a compound of Formula (I), wherein R¹ is piperazinyl. In some embodiments is a compound of Formula (I), wherein R¹ is 4-methyl piperazinyl. In some embodiments is a compound of Formula (I), wherein R¹ is thiomorpholinyl.

In some embodiments is a compound of Formula (I), wherein R¹ is a 7-membered optionally substituted heterocycloalkyl. In some embodiments is a compound of Formula (I), wherein R¹ is a 7-membered substituted heterocycloalkyl. In some embodiments is a compound of Formula (I), wherein R¹ is a 7-membered unsubstituted heterocycloalkyl. In some embodiments is a compound of Formula (I), wherein R¹ is azepanyl.

In some embodiments is a compound of Formula (I), wherein the compound of Formula (I) is a compound of Formula (Ic):

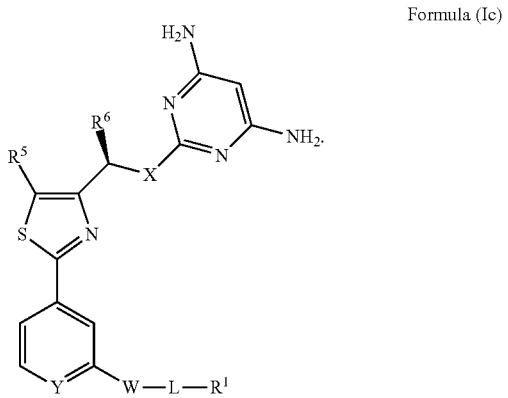

Formula (Ic)

In some embodiments is a compound of Formula (I), wherein the compound of Formula (I) is a compound of Formula (Id):

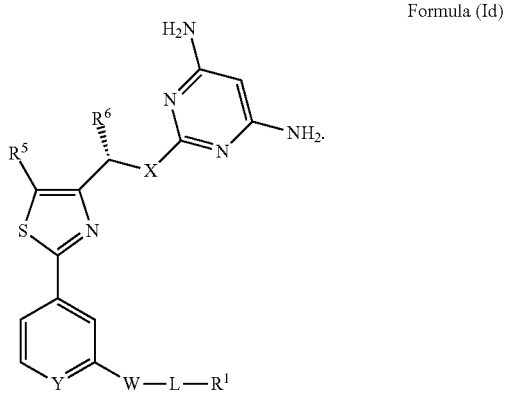

Formula (Id)

In some embodiments is a compound of Formula (Ic) or Formula (Id), wherein R⁵ is alkyl. In some embodiments is a compound of Formula (Ic) or Formula (Id), wherein R⁵ is methyl, ethyl, or propyl. In some embodiments is a compound of Formula (Ic) or Formula (Id), wherein R⁵ is methyl.

In some embodiments is a compound of Formula (Ic) or Formula (Id), wherein R⁶ is alkyl. In some embodiments is a compound of Formula (Ic) or Formula (Id), wherein R⁶ is methyl, ethyl, or propyl. In some embodiments is a compound of Formula (Ic) or Formula (Id), wherein R⁶ is methyl.

In some embodiments is a compound of Formula (Ic) or Formula (Id), wherein X is —S—.

In some embodiments is a compound of Formula (Ic) or Formula (Id), wherein Y is C(R⁹), R⁹ is optionally substituted alkoxy, W is —O—, L is optionally substituted alkylene, and R¹ is optionally substituted heterocycloalkyl. In some embodiments is a compound of Formula (Ic) or Formula (Id), wherein Y is C(R⁹), R⁹ is unsubstituted alkoxy, W is —O—, L is unsubstituted alkylene, and R¹ is optionally substituted heterocycloalkyl. In some embodiments is a compound of Formula (Ic) or Formula (Id), wherein Y is C(R⁹), R⁹ is unsubstituted alkoxy, W is —O—, L is unsubstituted alkylene, and R¹ is unsubstituted heterocycloalkyl. In some embodiments is a compound of Formula (Ic) or Formula (Id), wherein Y is C(R⁹), R⁹ is unsubstituted alkoxy, W is —O—, L is unsubstituted alkylene, and R¹ is piperidinyl, piperizanyl, or morpholinyl. In some embodiments is a compound of Formula (Ic) or Formula (Id), wherein Y is C(R⁹), R⁹ is methoxy, W is —O—, L is unsubstituted alkylene, and R¹ is piperidinyl, piperizanyl, or morpholinyl.

In some embodiments is a compound of Formula (I), wherein the compound of Formula (I) is selected from:

19
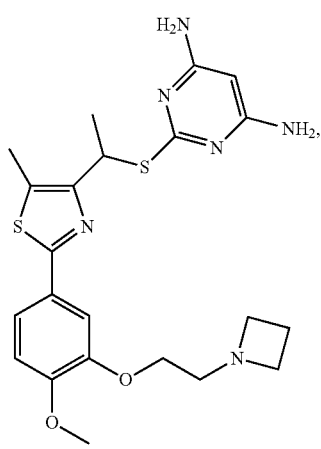
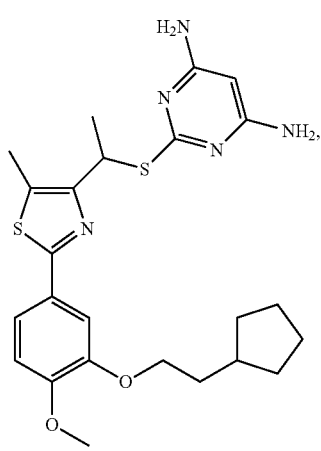
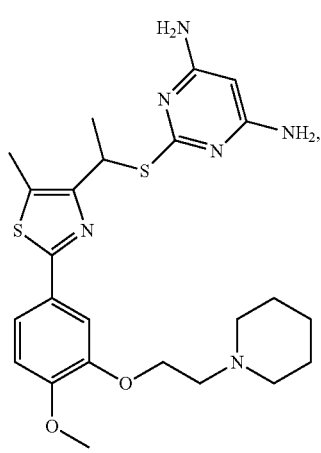
20
-continued
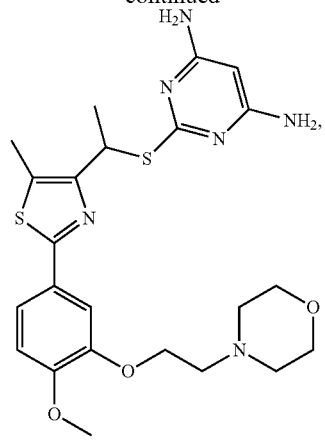
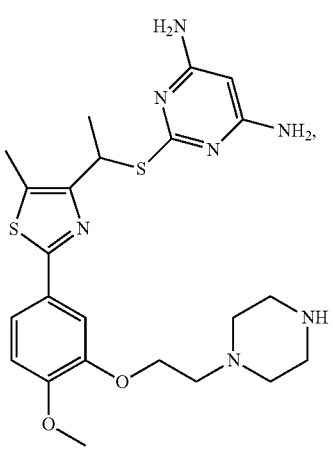
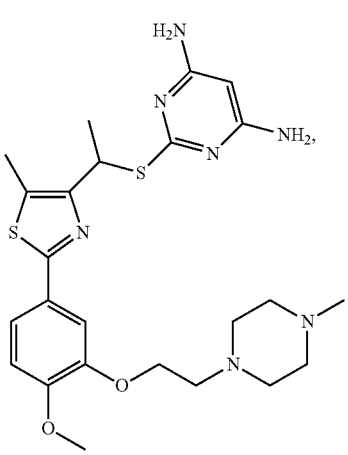

-continued
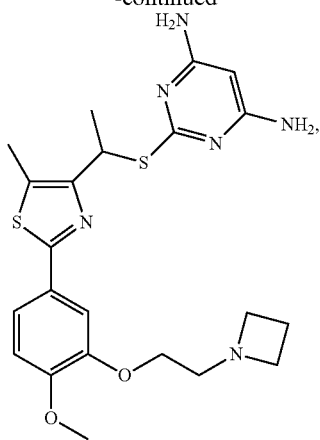
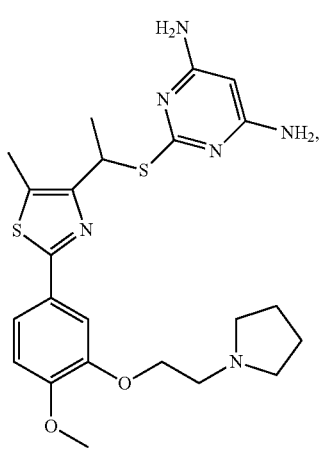
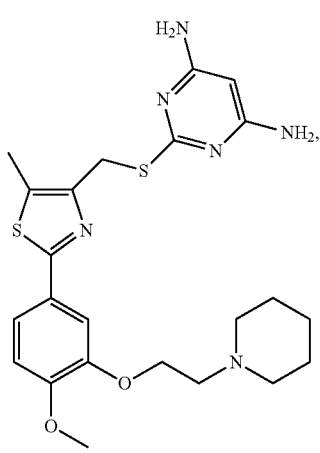
-continued
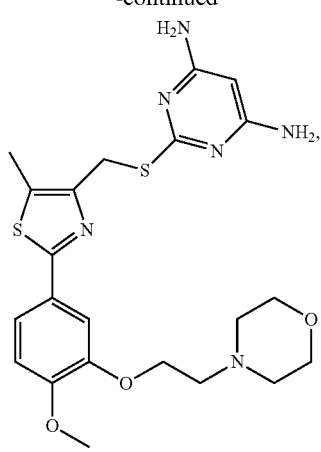
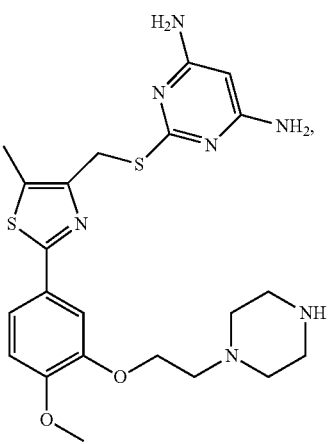
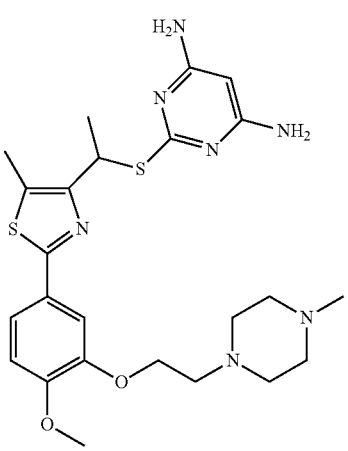

23
-continued
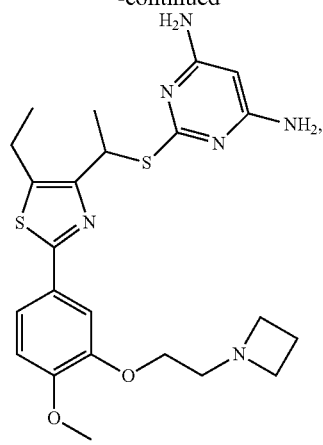
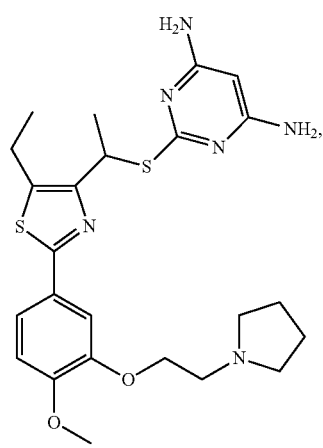
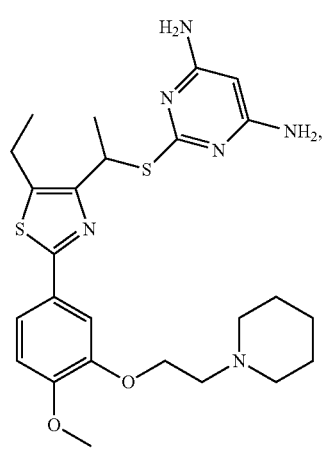
24
-continued
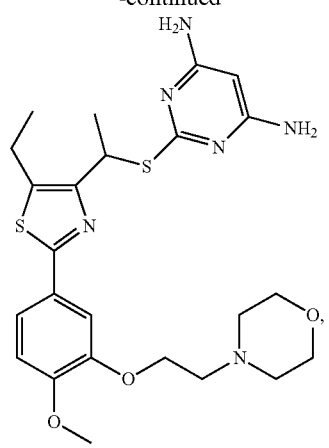
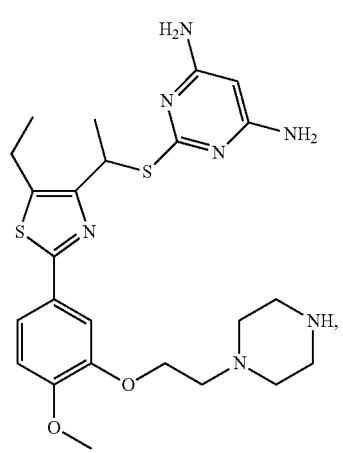
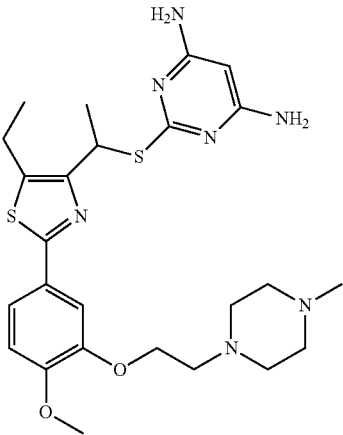

-continued
25
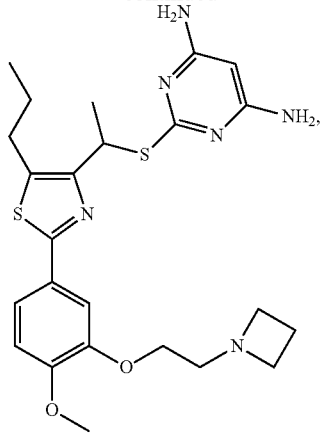
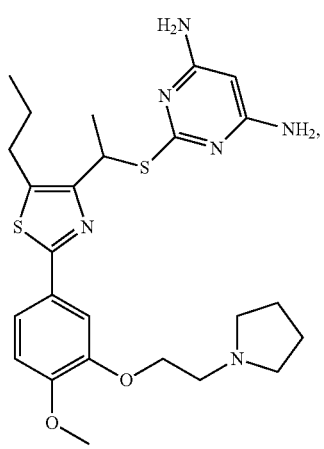
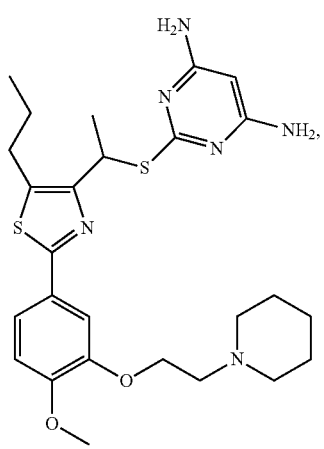
26
-continued
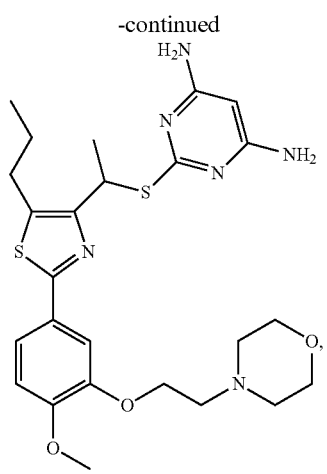
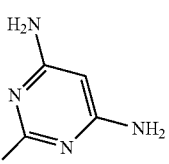
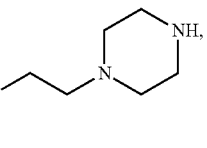
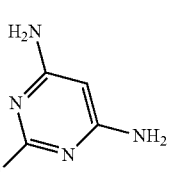
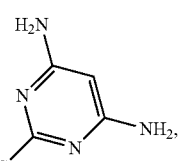
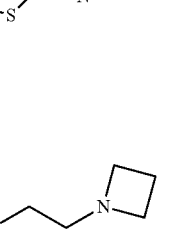

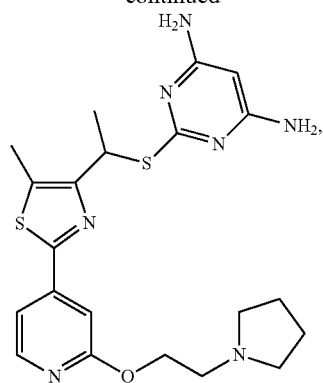
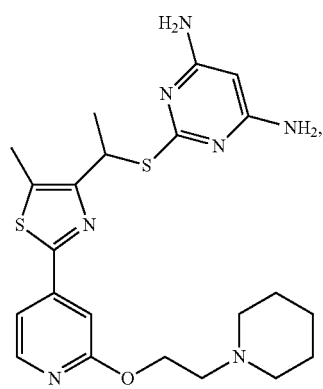
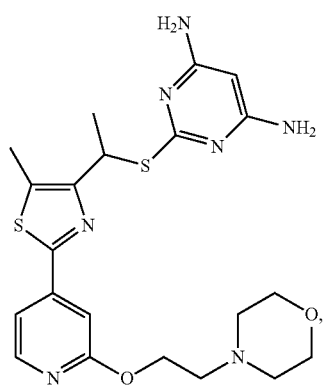
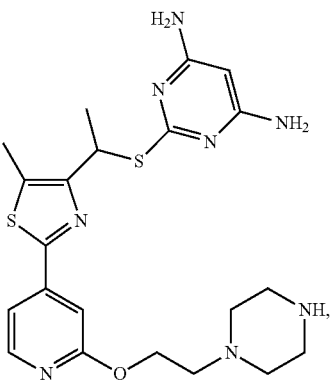
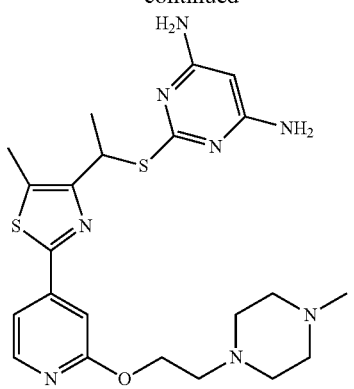
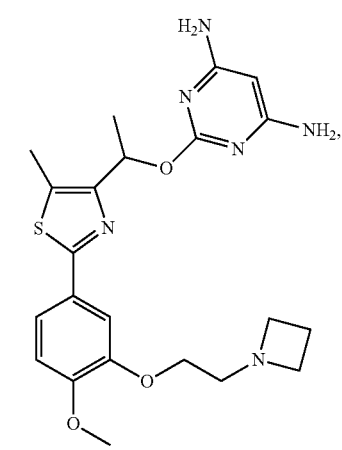
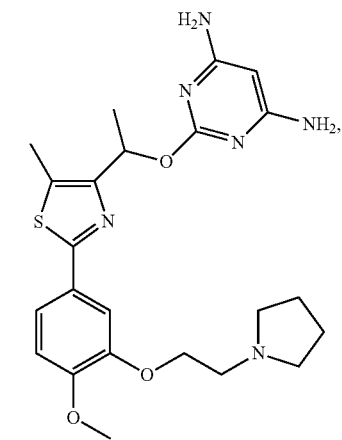
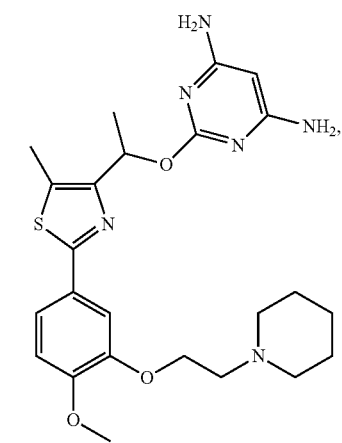

-continued
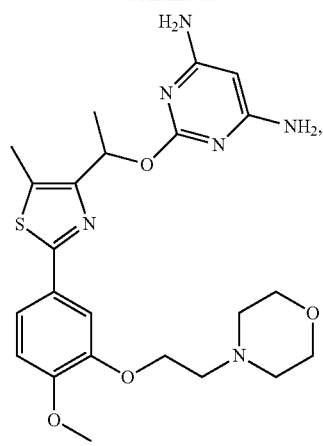
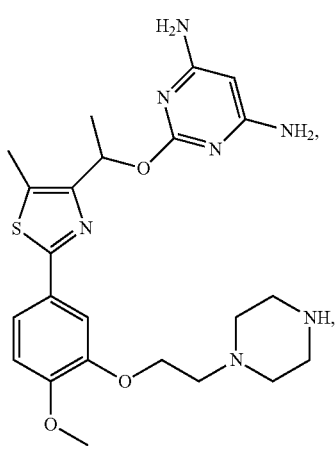
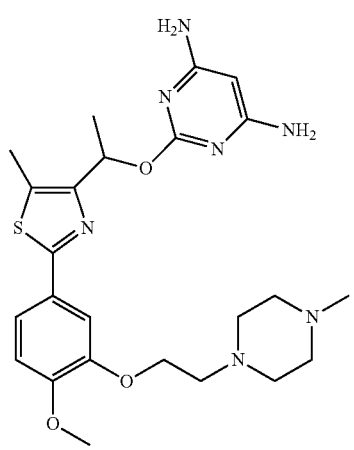
or a pharmaceutically acceptable salt or solvate thereof.
In some embodiments is a compound selected from:
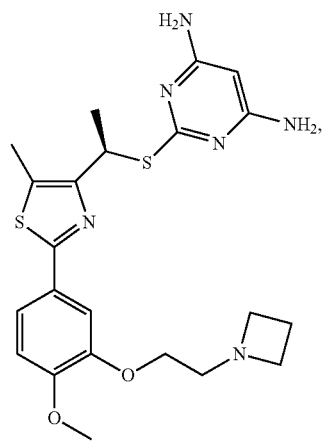
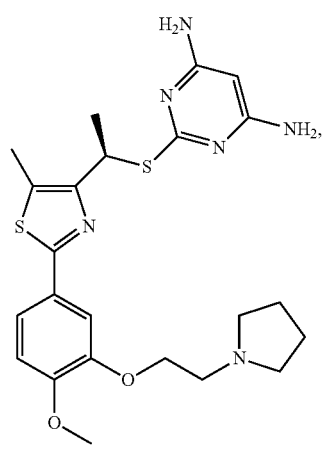

31
-continued
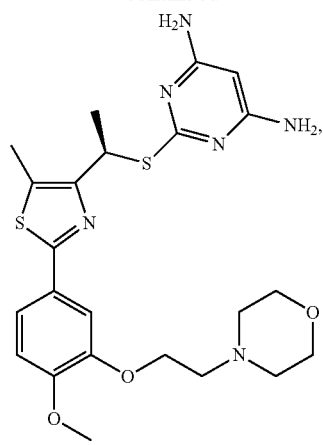
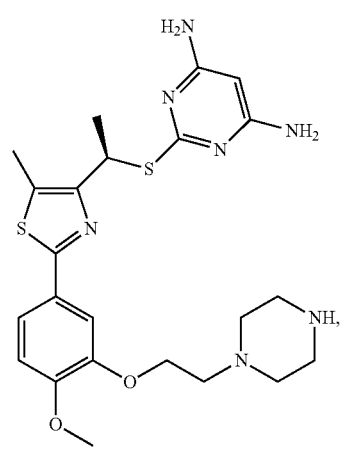
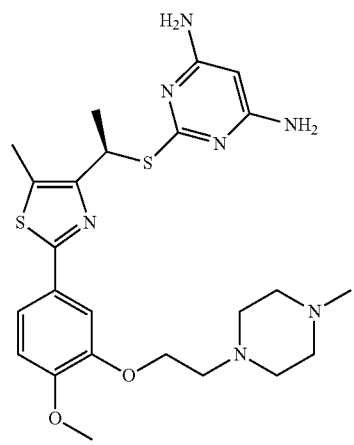
32
-continued
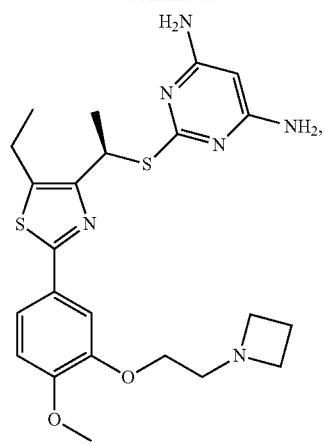
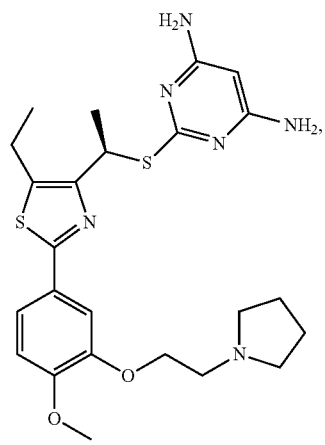
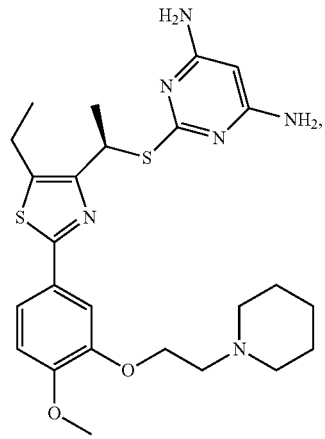

33
-continued
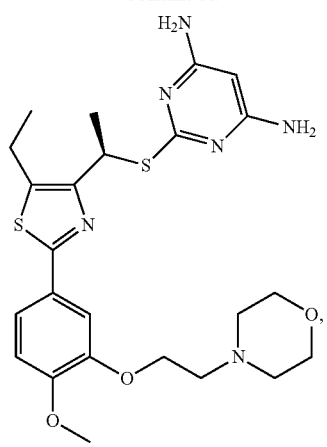
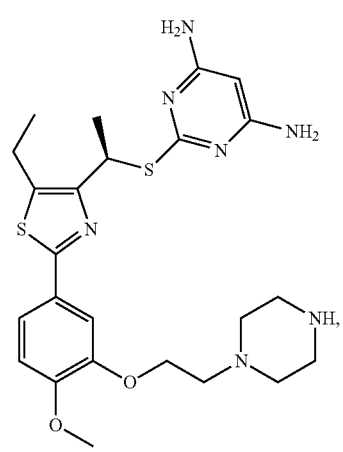
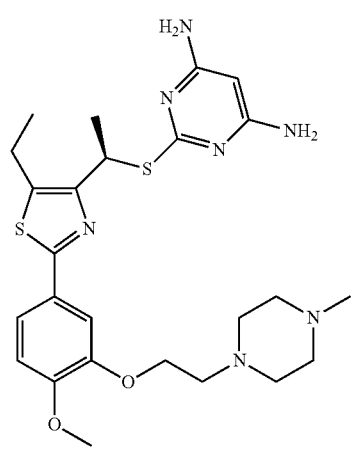
34
-continued
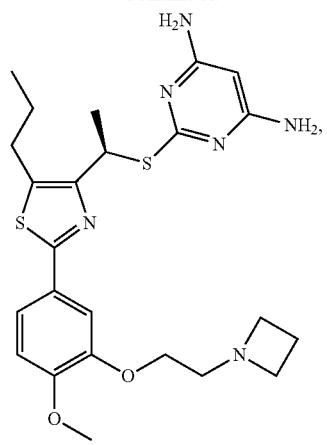
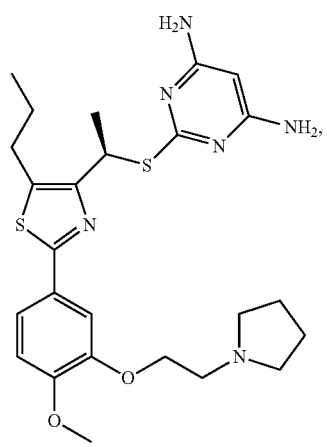
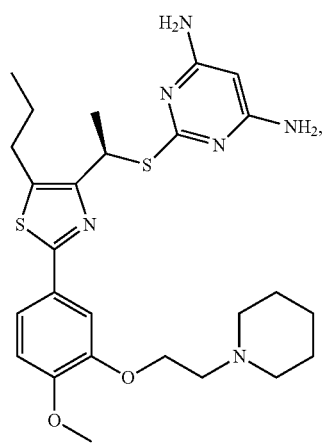

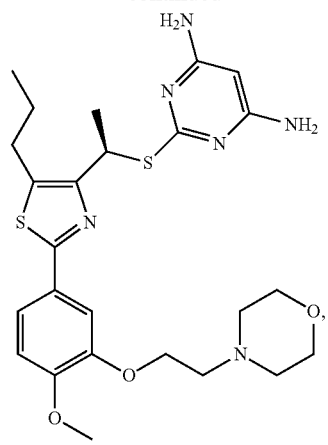
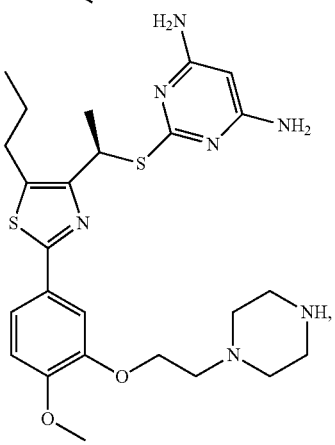
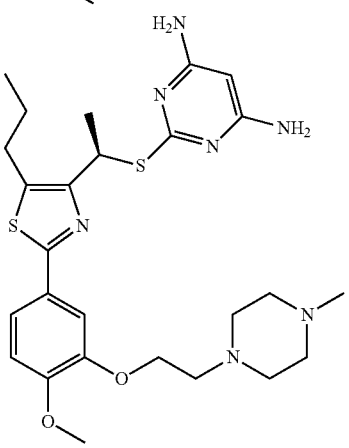
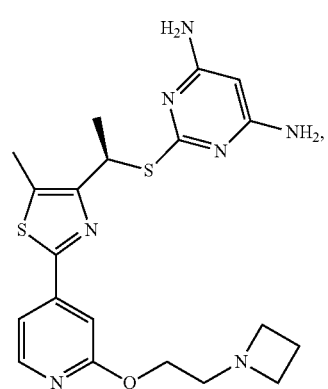
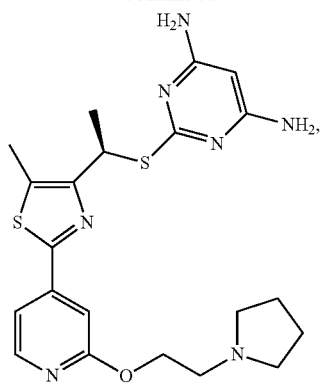
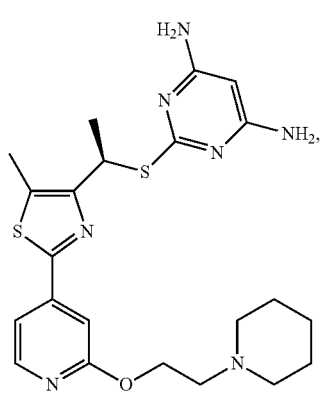
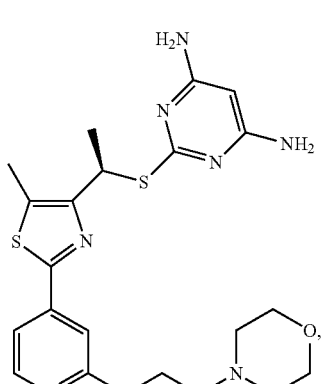
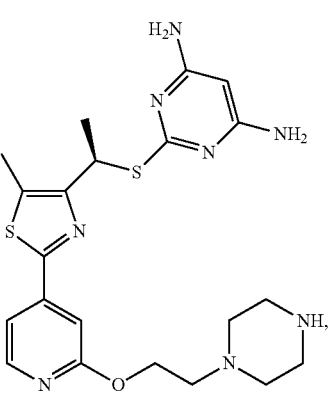

37
-continued
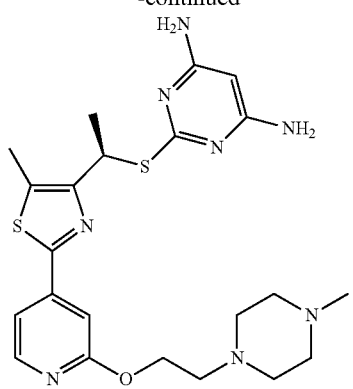
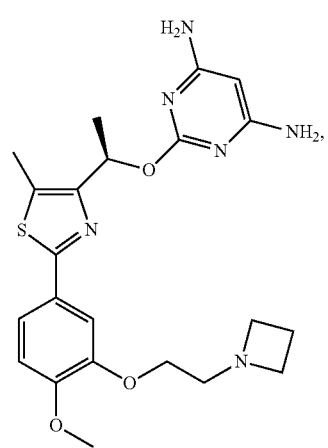
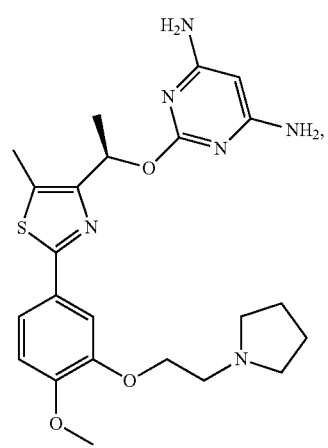
38
-continued
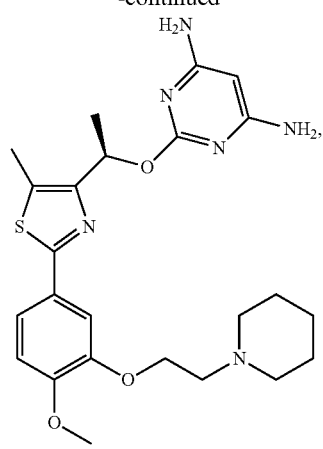
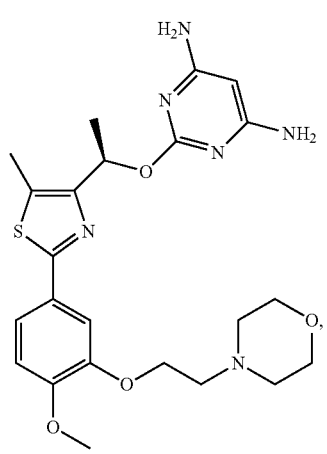
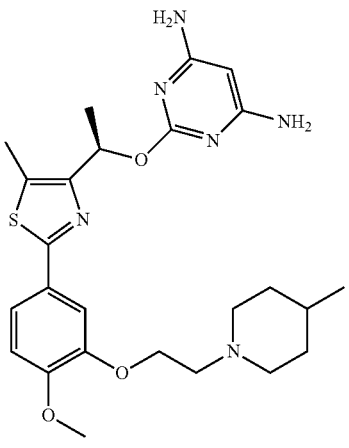

39
-continued
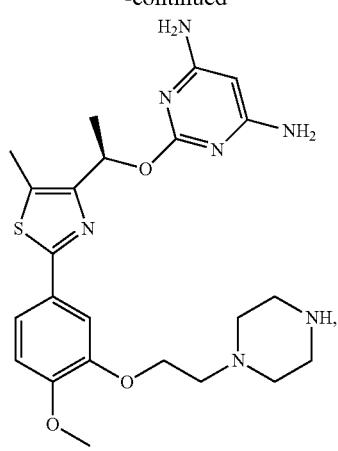
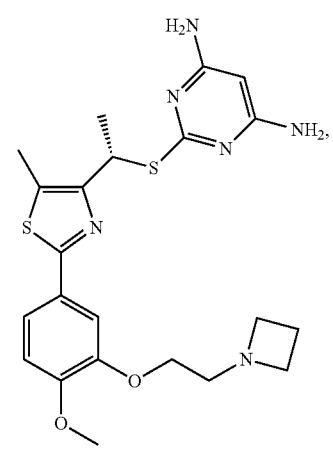
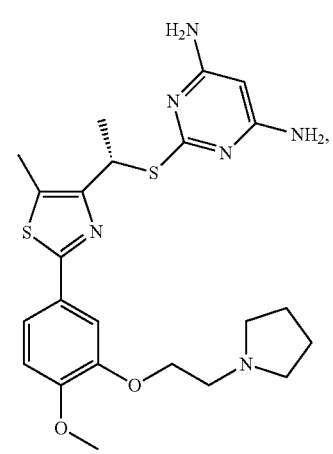
40
-continued
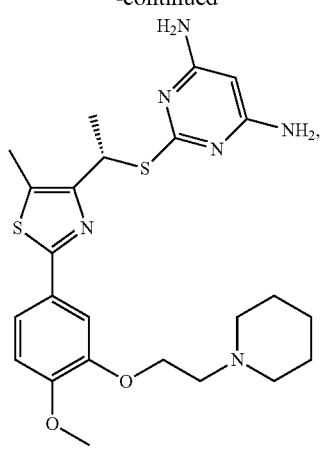
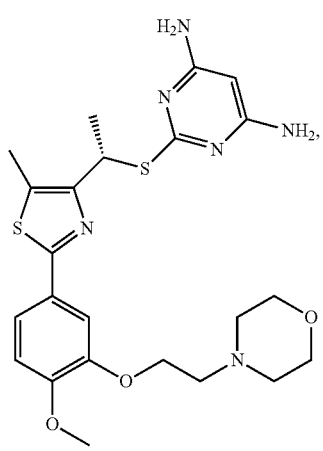
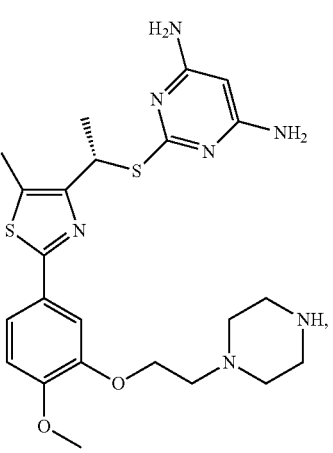

41
-continued
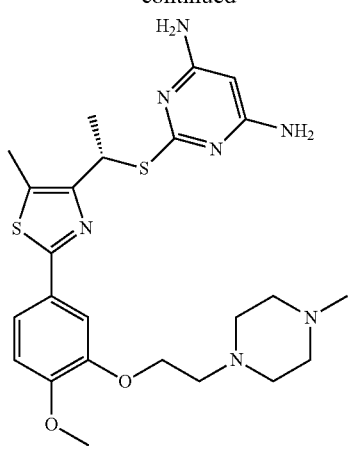
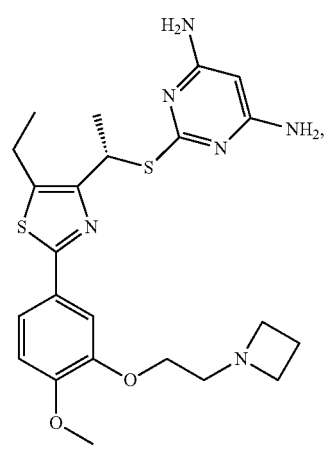
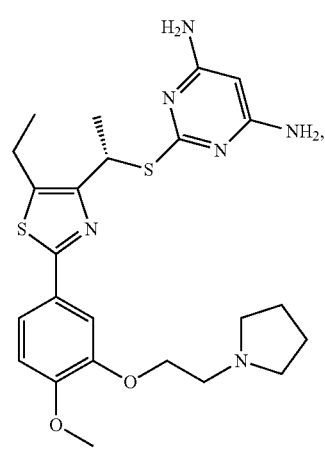
42
-continued
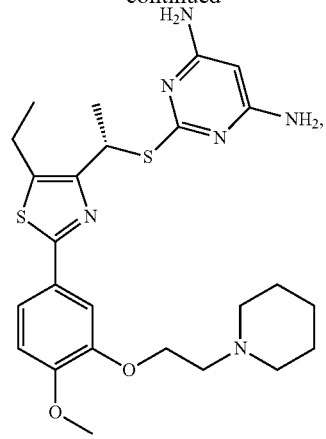
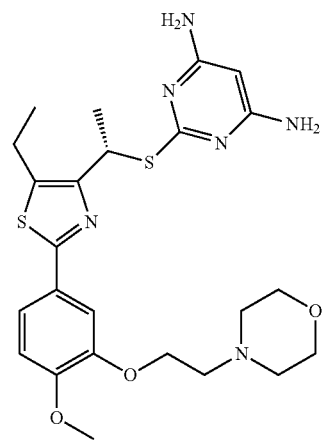
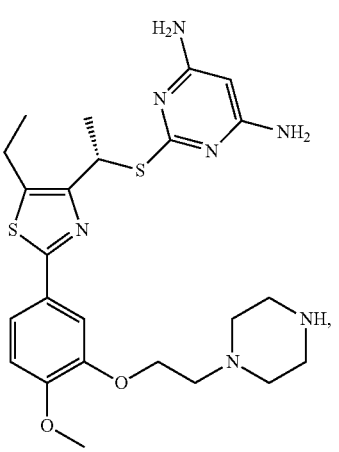

43
-continued
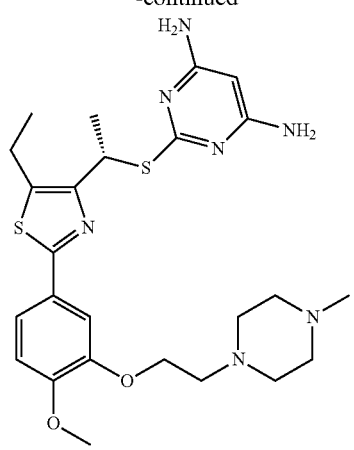
,
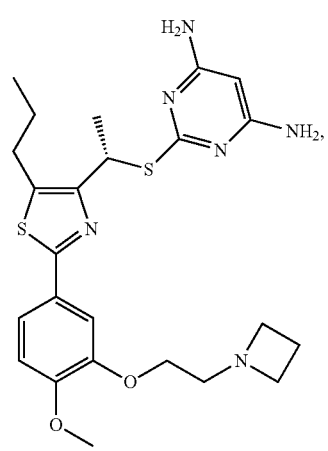
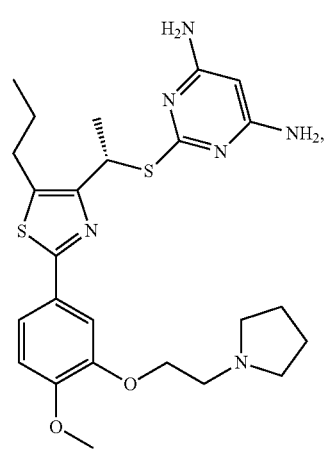
44
-continued
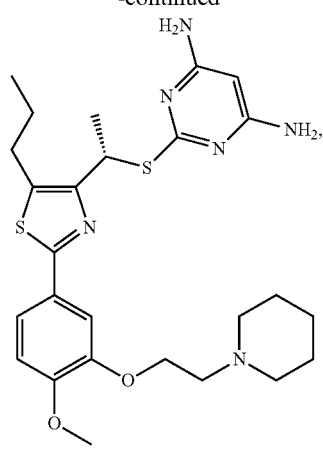
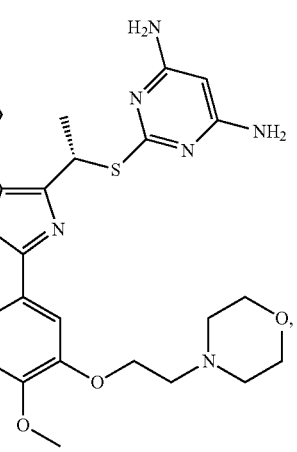
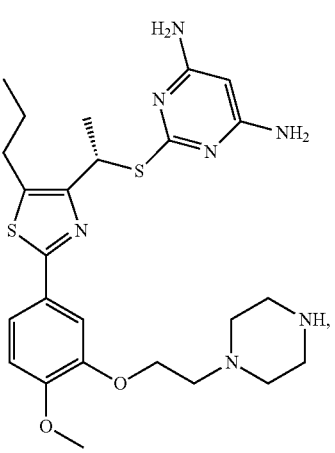

45
-continued
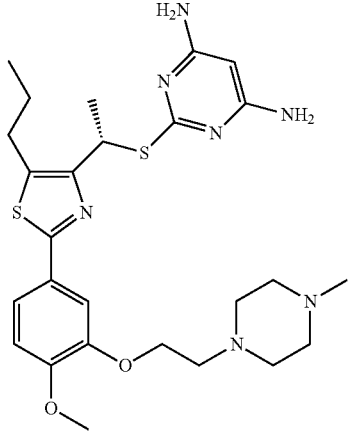
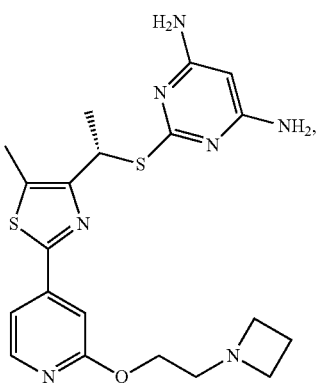
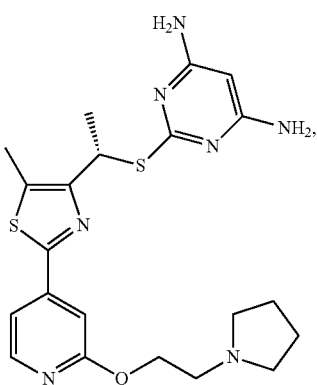
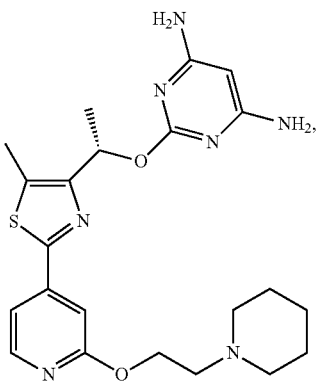
46
-continued
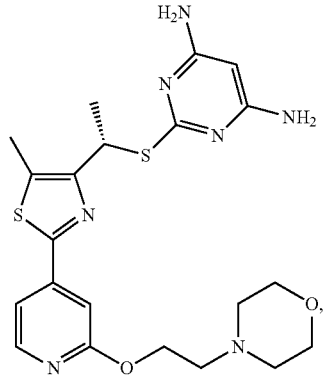
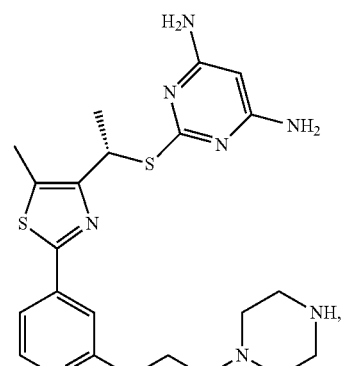
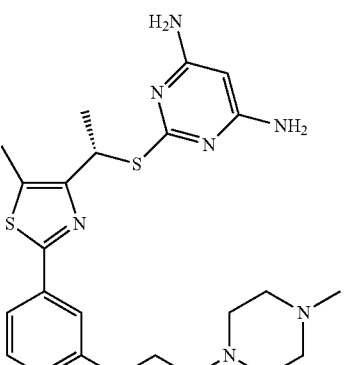
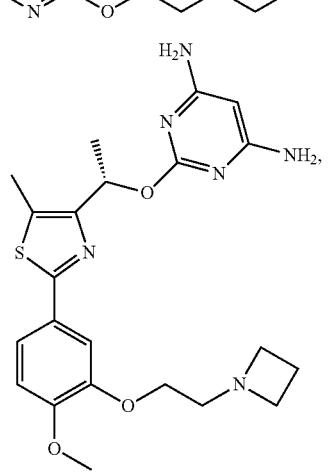

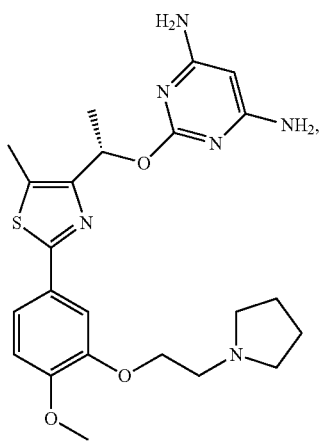

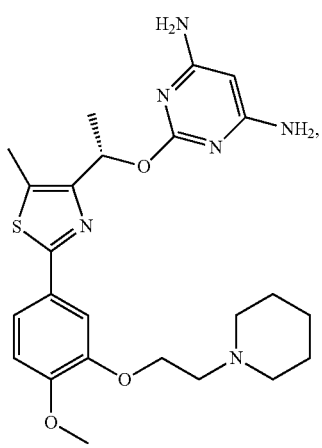

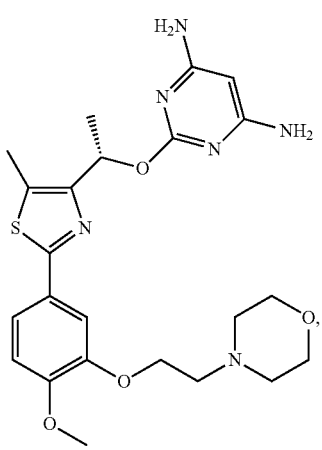

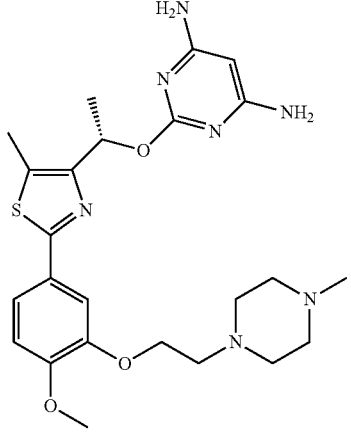

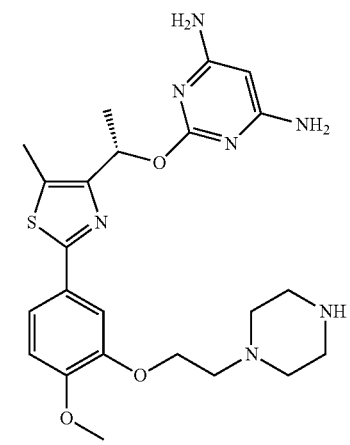

or a pharmaceutically acceptable salt or solvate thereof.

In embodiments, $R^1$ is substituted or unsubstituted heterocycloalkyl.

In embodiments, $R^1$ is unsubstituted heterocycloalkyl.

In embodiments, $R^1$ is substituted heterocycloalkyl/

In embodiments, $R^1$ is substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^1$ is substituted heterocycloalkyl (e.g., 3 to 8 membered heterocycloalkyl, 3 to 6 membered heterocycloalkyl, or 5 to 6 membered heterocycloalkyl) that is substituted with e.g., a "substituent group" as described herein, a "size-limited substituent" as described herein, or "lower substituent group" as described herein. In embodiments, $R^1$ is unsubstituted heterocycloalkyl (e.g., 3 to 8 membered heterocycloalkyl, 3 to 6 membered heterocycloalkyl, or 5 to 6 membered heterocycloalkyl).

In embodiments, $R^2$, $R^3$ and $R^4$ are independently hydrogen, halogen, oxo, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —SH, —S(O)H, —$S(O)_2H$, —$S(O)_3H$, —$S(O)_4H$, —$SONH_2$, —$SO_2NH_2$, —$NHNH_2$, —$ONH_2$, —$NHC(O)NHNH_2$, —$NHC(O)NH_2$, —N(O), —$N(O)_2$, —$NH_2$, —C(O)H, —C(O)OH, —$C(O)NH_2$, —OH, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

In embodiments, $R^2$, $R^3$ and $R^4$ are independently unsubstituted alkyl, unsubstituted heteroalkyl, unsubstituted cycloalkyl, unsubstituted heterocycloalkyl, unsubstituted aryl or unsubstituted heteroaryl.

In embodiments, $R^2$, $R^3$ and $R^4$ are independently substituted alkyl, substituted heteroalkyl, substituted cycloalkyl, substituted heterocycloalkyl, substituted aryl or substituted heteroaryl.

In embodiments, $R^2$, $R^3$ and $R^4$ are independently substituted or unsubstituted alkyl (e.g., $C_1$-$C_8$ alkyl, $C_1$-$C_6$ alkyl, or $C_1$-$C_4$ alkyl). In embodiments, $R^2$, $R^3$ and $R^4$ are independently substituted alkyl (e.g., $C_1$-$C_8$ alkyl, $C_1$-$C_6$ alkyl, or $C_1$-$C_4$ alkyl) that is substituted with e.g., a "substituent group" as described herein, a "size-limited substituent" as described herein, or "lower substituent group" as described herein. In embodiments, $R^2$, $R^3$ and $R^4$ are independently unsubstituted alkyl (e.g., $C_1$-$C_8$ alkyl, $C_1$-$C_6$ alkyl, or $C_1$-$C_4$ alkyl).

In embodiments, $R^2$, $R^3$ and $R^4$ are independently substituted or unsubstituted heteroalkyl (e.g., 2 to 8 membered heteroalkyl, 2 to 6 membered heteroalkyl, or 2 to 4 membered heteroalkyl). In embodiments, $R^2$, $R^3$ and $R^4$ are independently substituted heteroalkyl (e.g., 2 to 8 membered heteroalkyl, 2 to 6 membered heteroalkyl, or 2 to 4 membered heteroalkyl) that is substituted with e.g., a "substituent group" as described herein, a "size-limited substituent" as described herein, or "lower substituent group" as described herein. In embodiments, $R^2$, $R^3$ and $R^4$ are independently an unsubstituted heteroalkyl (e.g., 2 to 8 membered heteroalkyl, 2 to 6 membered heteroalkyl, or 2 to 4 membered heteroalkyl).

In embodiments, $R^2$, $R^3$ and $R^4$ are independently substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^2$, $R^3$ and $R^4$ are independently substituted cycloalkyl (e.g., $C_3$-$C_8$ cycloalkyl, $C_3$-$C_6$ cycloalkyl, or $C_5$-$C_6$ cycloalkyl) that is substituted with e.g., a "substituent group" as described herein, a "size-limited substituent" as described herein, or "lower substituent group" as described herein. In embodiments, $R^2$, $R^3$ and $R^4$ are independently unsubstituted cycloalkyl (e.g., $C_3$-$C_8$ cycloalkyl, $C_3$-$C_6$ cycloalkyl, or $C_5$-$C_6$ cycloalkyl).

In embodiments, $R^2$, $R^3$ and $R^4$ are independently substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^2$, $R^3$ and $R^4$ are independently substituted heterocycloalkyl (e.g., 3 to 8 membered heterocycloalkyl, 3 to 6 membered heterocycloalkyl, or 5 to 6 membered heterocycloalkyl) that is substituted with e.g., a "substituent group" as described herein, a "size-limited substituent" as described herein, or "lower substituent group" as described herein. In embodiments, $R^2$, $R^3$ and $R^4$ are independently unsubstituted heterocycloalkyl (e.g., 3 to 8 membered heterocycloalkyl, 3 to 6 membered heterocycloalkyl, or 5 to 6 membered heterocycloalkyl).

In embodiments, $R^2$, $R^3$ and $R^4$ are independently substituted or unsubstituted aryl (e.g., $C_6$-$C_{10}$ aryl, $C_{10}$ aryl, or phenyl). In embodiments, $R^2$, $R^3$ and $R^4$ are independently substituted aryl (e.g., $C_6$-$C_{10}$ aryl, $C_{10}$ aryl, or phenyl) that is substituted with e.g., a "substituent group" as described herein, a "size-limited substituent" as described herein, or "lower substituent group" as described herein. In embodiments, $R^2$, $R^3$ and $R^4$ are independently an unsubstituted aryl (e.g., $C_6$-$C_{10}$ aryl, $C_{10}$ aryl, or phenyl).

In embodiments, $R^2$, $R^3$ and $R^4$ are independently substituted or unsubstituted heteroaryl (e.g., 5 to 10 membered heteroaryl, 5 to 9 membered heteroaryl, or 5 to 6 membered heteroaryl). In embodiments, $R^2$, $R^3$ and $R^4$ are independently substituted heteroaryl (e.g., 5 to 10 membered heteroaryl, 5 to 9 membered heteroaryl, or 5 to 6 membered heteroaryl) that is substituted with e.g., a "substituent group" as described herein, a "size-limited substituent" as described herein, or "lower substituent group" as described herein. In embodiments, $R^2$, $R^3$ and $R^4$ are independently unsubstituted heteroaryl (e.g., 5 to 10 membered heteroaryl, 5 to 9 membered heteroaryl, or 5 to 6 membered heteroaryl).

In embodiments, $R^5$ is hydrogen, halogen, oxo, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —SH, —S(O)H, —$S(O)_2H$, —$S(O)_3H$, —$S(O)_4H$, —$SONH_2$, —$SO_2NH_2$, —$NHNH_2$, —$ONH_2$, —NHC(O)$NHNH_2$, —NHC(O)$NH_2$, —N(O), —N(O)$_2$, —$NH_2$, —C(O)H, —C(O)OH, —C(O)$NH_2$, —OH, —$NHSO_2H$, —NHC(O)H, —NHC(O)OH, —NHOH, —$OCF_3$, —$OCCl_3$, —$OCBr_3$, —$OCl_3$, —$OCHF_2$, —$OCHCl_2$, —$OCHBr_2$, —$OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

In embodiments, $R^5$ is unsubstituted alkyl, unsubstituted heteroalkyl, unsubstituted cycloalkyl, unsubstituted heterocycloalkyl, unsubstituted aryl or unsubstituted heteroaryl.

In embodiments, $R^5$ is substituted alkyl, substituted heteroalkyl, substituted cycloalkyl, substituted heterocycloalkyl, substituted aryl or substituted heteroaryl.

In embodiments, $R^5$ is substituted or unsubstituted alkyl (e.g., $C_1$-$C_8$ alkyl, $C_1$-$C_6$ alkyl, or $C_1$-$C_4$ alkyl). In embodiments, $R^5$ is substituted alkyl (e.g., $C_1$-$C_8$ alkyl, $C_1$-$C_6$ alkyl, or $C_1$-$C_4$ alkyl) that is substituted with e.g., a "substituent group" as described herein, a "size-limited substituent" as described herein, or "lower substituent group" as described herein. In embodiments, $R^5$ is unsubstituted alkyl (e.g., $C_1$-$C_8$ alkyl, $C_1$-$C_6$ alkyl, or $C_1$-$C_4$ alkyl).

In embodiments, $R^5$ is substituted or unsubstituted heteroalkyl (e.g., 2 to 8 membered heteroalkyl, 2 to 6 membered heteroalkyl, or 2 to 4 membered heteroalkyl). In embodiments, $R^5$ is substituted heteroalkyl (e.g., 2 to 8 membered heteroalkyl, 2 to 6 membered heteroalkyl, or 2 to 4 membered heteroalkyl) that is substituted with e.g., a "substituent group" as described herein, a "size-limited substituent" as described herein, or "lower substituent group" as described herein. In embodiments, $R^5$ is an unsubstituted heteroalkyl (e.g., 2 to 8 membered heteroalkyl, 2 to 6 membered heteroalkyl, or 2 to 4 membered heteroalkyl).

In embodiments, $R^5$ is substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^5$ is substituted cycloalkyl (e.g., $C_3$-$C_8$ cycloalkyl, $C_3$-$C_6$ cycloalkyl, or $C_5$-$C_6$ cycloalkyl) that is substituted with e.g., a "substituent group" as described herein, a "size-limited substituent" as described herein, or "lower substituent group" as described herein. In embodiments, $R^5$ is unsubstituted cycloalkyl (e.g., $C_3$-$C_8$ cycloalkyl, $C_3$-$C_6$ cycloalkyl, or $C_5$-$C_6$ cycloalkyl).

In embodiments, $R^5$ is substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^5$ is substituted heterocycloalkyl (e.g., 3 to 8 membered heterocycloalkyl, 3 to 6 membered heterocycloalkyl, or 5 to 6 membered heterocycloalkyl) that is substituted with e.g., a "substituent group" as described herein, a "size-limited substituent" as described herein, or "lower substituent group" as described herein. In embodiments, $R^5$ is unsubstituted heterocycloalkyl (e.g., 3 to 8 membered heterocycloalkyl, 3 to 6 membered heterocycloalkyl, or 5 to 6 membered heterocycloalkyl).

In embodiments, $R^5$ is substituted or unsubstituted aryl (e.g., $C_6$-$C_{10}$ aryl, $C_{10}$ aryl, or phenyl). In embodiments, $R^5$ is substituted aryl (e.g., $C_6$-$C_{10}$ aryl, $C_{10}$ aryl, or phenyl) that is substituted with e.g., a "substituent group" as described herein, a "size-limited substituent" as described herein, or "lower substituent group" as described herein. In embodiments, $R^5$ is an unsubstituted aryl (e.g., $C_6$-$C_{10}$ aryl, $C_{10}$ aryl, or phenyl).

In embodiments, $R^5$ is substituted or unsubstituted heteroaryl (e.g., 5 to 10 membered heteroaryl, 5 to 9 membered heteroaryl, or 5 to 6 membered heteroaryl). In embodiments, $R^5$ is substituted heteroaryl (e.g., 5 to 10 membered heteroaryl, 5 to 9 membered heteroaryl, or 5 to 6 membered heteroaryl) that is substituted with e.g., a "substituent group" as described herein, a "size-limited substituent" as described herein, or "lower substituent group" as described herein. In embodiments, $R^5$ is unsubstituted heteroaryl (e.g., 5 to 10 membered heteroaryl, 5 to 9 membered heteroaryl, or 5 to 6 membered heteroaryl).

In embodiments, $R^6$ and $R^7$ are independently hydrogen, halogen, or substituted or unsubstituted alkyl.

In embodiments, $R^6$ and $R^7$ are independently unsubstituted alkyl.

In embodiments, $R^6$ and $R^7$ are independently substituted alkyl.

In embodiments, $R^6$ and $R^7$ are independently substituted or unsubstituted alkyl (e.g., $C_1$-$C_8$ alkyl, $C_1$-$C_6$ alkyl, or $C_1$-$C_4$ alkyl). In embodiments, $R^6$ and $R^7$ are independently substituted alkyl (e.g., $C_1$-$C_8$ alkyl, $C_1$-$C_6$ alkyl, or $C_1$-$C_4$ alkyl) that is substituted with e.g., a "substituent group" as described herein, a "size-limited substituent" as described herein, or "lower substituent group" as described herein. In embodiments, $R^6$ and $R^7$ are independently unsubstituted alkyl (e.g., $C_1$-$C_8$ alkyl, $C_1$-$C_6$ alkyl, or $C_1$-$C_4$ alkyl).

In embodiments, $R^6$ and $R^7$ are taken together with the carbon to which they are attached to form a substituted or unsubstituted cycloalkyl.

In embodiments, $R^6$ and $R^7$ are taken together with the carbon to which they are attached to form an unsubstituted cycloalkyl.

In embodiments, $R^6$ and $R^7$ are taken together with the carbon to which they are attached to form a substituted cycloalkyl.

In embodiments, $R^6$ and $R^7$ are taken together with the carbon to which they are attached to form a substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^6$ and $R^7$ are taken together with the carbon to which they are attached to form a substituted cycloalkyl (e.g., $C_3$-$C_8$ cycloalkyl, $C_3$-$C_6$ cycloalkyl, or $C_5$-$C_6$ cycloalkyl) that is substituted with e.g., a "substituent group" as described herein, a "size-limited substituent" as described herein, or "lower substituent group" as described herein. In embodiments, $R^6$ and $R^7$ are taken together with the carbon to which they are attached to form an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^8$ is hydrogen, or substituted or unsubstituted alkyl.

In embodiments, $R^8$ is unsubstituted alkyl, unsubstituted heteroalkyl.

In embodiments, $R^8$ is substituted alkyl.

In embodiments, $R^8$ is substituted or unsubstituted alkyl (e.g., $C_1$-$C_8$ alkyl, $C_1$-$C_6$ alkyl, or $C_1$-$C_4$ alkyl). In embodiments, $R^8$ is substituted alkyl (e.g., $C_1$-$C_8$ alkyl, $C_1$-$C_6$ alkyl, or $C_1$-$C_4$ alkyl) that is substituted with e.g., a "substituent group" as described herein, a "size-limited substituent" as described herein, or "lower substituent group" as described herein. In embodiments, $R^8$ is unsubstituted alkyl (e.g., $C_1$-$C_8$ alkyl, $C_1$-$C_6$ alkyl, or $C_1$-$C_4$ alkyl).

In embodiments, $R^9$ is hydrogen, halogen, oxo, —$CF_3$, —$CCl_3$, —$CBr_3$, —$CI_3$, —$CHF_2$, —$CHCl_2$, —$CHBr_2$, —$CH_2F$, —$CH_2Cl$, —$CH_2Br$, —CN, —SH, —S(O)H, —$S(O)_2H$, —$S(O)_3H$, —$S(O)_4H$, —$SONH_2$, —$SO_2NH_2$, —$NHNH_2$, —$ONH_2$, —$NHC(O)NHNH_2$, —$NHC(O)NH_2$, —N(O), —$N(O)_2$, —$NH_2$, —C(O)H, —C(O)OH, —C(O)NH_2, —OH, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

In embodiments, $R^9$ is unsubstituted alkyl, unsubstituted heteroalkyl, unsubstituted cycloalkyl, unsubstituted heterocycloalkyl, unsubstituted aryl or unsubstituted heteroaryl.

In embodiments, $R^9$ is substituted alkyl, substituted heteroalkyl, substituted cycloalkyl, substituted heterocycloalkyl, substituted aryl or substituted heteroaryl.

In embodiments, $R^9$ is substituted or unsubstituted alkyl (e.g., $C_1$-$C_8$ alkyl, $C_1$-$C_6$ alkyl, or $C_1$-$C_4$ alkyl). In embodiments, $R^9$ is substituted alkyl (e.g., $C_1$-$C_8$ alkyl, $C_1$-$C_6$ alkyl, or $C_1$-$C_4$ alkyl) that is substituted with e.g., a "substituent group" as described herein, a "size-limited substituent" as described herein, or "lower substituent group" as described herein. In embodiments, $R^9$ is unsubstituted alkyl (e.g., $C_1$-$C_8$ alkyl, $C_1$-$C_6$ alkyl, or $C_1$-$C_4$ alkyl).

In embodiments, $R^9$ is substituted or unsubstituted heteroalkyl (e.g., 2 to 8 membered heteroalkyl, 2 to 6 membered heteroalkyl, or 2 to 4 membered heteroalkyl). In embodiments, $R^9$ is substituted heteroalkyl (e.g., 2 to 8 membered heteroalkyl, 2 to 6 membered heteroalkyl, or 2 to 4 membered heteroalkyl) that is substituted with e.g., a "substituent group" as described herein, a "size-limited substituent" as described herein, or "lower substituent group" as described herein. In embodiments, $R^9$ is an unsubstituted heteroalkyl (e.g., 2 to 8 membered heteroalkyl, 2 to 6 membered heteroalkyl, or 2 to 4 membered heteroalkyl).

In embodiments, $R^9$ is substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^9$ is substituted cycloalkyl (e.g., $C_3$-$C_8$ cycloalkyl, $C_3$-$C_6$ cycloalkyl, or $C_5$-$C_6$ cycloalkyl) that is substituted with e.g., a "substituent group" as described herein, a "size-limited substituent" as described herein, or "lower substituent group" as described herein. In embodiments, $R^9$ is unsubstituted cycloalkyl (e.g., $C_3$-$C_8$ cycloalkyl, $C_3$-$C_6$ cycloalkyl, or $C_5$-$C_6$ cycloalkyl).

In embodiments, $R^9$ is substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^9$ is substituted heterocycloalkyl (e.g., 3 to 8 membered heterocycloalkyl, 3 to 6 membered heterocycloalkyl, or 5 to 6 membered heterocycloalkyl) that is substituted with e.g., a "substituent group" as described herein, a "size-limited substituent" as described herein, or "lower substituent group" as described herein. In embodiments, $R^9$ is unsubstituted heterocycloalkyl (e.g., 3 to 8 membered heterocycloalkyl, 3 to 6 membered heterocycloalkyl, or 5 to 6 membered heterocycloalkyl).

In embodiments, $R^9$ is substituted or unsubstituted aryl (e.g., $C_6$-$C_{10}$ aryl, $C_{10}$ aryl, or phenyl). In embodiments, $R^9$ is substituted aryl (e.g., $C_6$-$C_{10}$ aryl, $C_{10}$ aryl, or phenyl) that is substituted with e.g., a "substituent group" as described herein, a "size-limited substituent" as described herein, or "lower substituent group" as described herein. In embodiments, $R^9$ is an unsubstituted aryl (e.g., $C_6$-$C_{10}$ aryl, $C_{10}$ aryl, or phenyl).

In embodiments, $R^9$ is substituted or unsubstituted heteroaryl (e.g., 5 to 10 membered heteroaryl, 5 to 9 membered heteroaryl, or 5 to 6 membered heteroaryl). In embodiments, $R^9$ is substituted heteroaryl (e.g., 5 to 10 membered heteroaryl, 5 to 9 membered heteroaryl, or 5 to 6 membered heteroaryl) that is substituted with e.g., a "substituent group" as described herein, a "size-limited substituent" as described herein, or "lower substituent group" as described herein. In embodiments, $R^9$ is unsubstituted heteroaryl (e.g., 5 to 10 membered heteroaryl, 5 to 9 membered heteroaryl, or 5 to 6 membered heteroaryl).

In embodiments, L is substituted or unsubstituted alkylene, substituted or unsubstituted alkenylene, or substituted or unsubstituted alkynylene.

In embodiments, L is substituted alkylene, substituted alkenylene, or substituted alkynylene.

In embodiments, L is unsubstituted alkylene, unsubstituted alkenylene, or unsubstituted alkynylene.

In embodiments, L is substituted or unsubstituted alkylene (e.g., $C_1$-$C_8$ alkyl, $C_1$-$C_6$ alkylene, or $C_1$-$C_4$ alkylene). In embodiments, L is substituted alkylene (e.g., $C_1$-$C_8$ alkylene, $C_1$-$C_6$ alkylene, or $C_1$-$C_4$ alkylene) that is substituted with e.g., a "substituent group" as described herein, a "size-limited substituent" as described herein, or "lower substituent group" as described herein. In embodiments, L is unsubstituted alkylene (e.g., $C_1$-$C_8$ alkylene, $C_1$-$C_6$ alkylene, or $C_1$-$C_4$ alkylene).

In embodiments, L is substituted or unsubstituted alkenylene (e.g., $C_1$-$C_8$ alkenylene, $C_1$-$C_6$ alkenylene, or $C_1$-$C_4$ alkenylene). In embodiments, L is substituted alkenylene (e.g., $C_1$-$C_8$ alkenylene, $C_1$-$C_6$ alkenylene, or $C_1$-$C_4$ alkenylene) that is substituted with e.g., a "substituent group" as described herein, a "size-limited substituent" as described herein, or "lower substituent group" as described herein. In embodiments, L is unsubstituted alkenylene (e.g., $C_1$-$C_8$ alkenylene, $C_1$-$C_6$ alkenylene, or $C_1$-$C_4$ alkenylene).

In embodiments, L is substituted or unsubstituted alkynylene (e.g., $C_1$-$C_8$ alkynylene, $C_1$-$C_6$ alkynylene, or $C_1$-$C_4$ alkynylene). In embodiments, L is substituted alkynylene (e.g., $C_1$-$C_8$ alkynylene, $C_1$-$C_6$ alkynylene, or $C_1$-$C_4$ alkynylene) that is substituted with e.g., a "substituent group" as described herein, a "size-limited substituent" as described herein, or "lower substituent group" as described herein. In embodiments, L is unsubstituted alkynylene (e.g., $C_1$-$C_8$ alkynylene, $C_1$-$C_6$ alkynylene, or $C_1$-$C_4$ alkynylene).

Further to any aspect disclosed herein, and embodiment thereof, in embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is unsubstituted (e.g., is an unsubstituted alkyl, unsubstituted heteroalkyl, unsubstituted cycloalkyl, unsubstituted heterocycloalkyl, unsubstituted aryl, unsubstituted heteroaryl, unsubstituted alkylene, unsubstituted heteroalkylene, unsubstituted cycloalkylene, unsubstituted heterocycloalkylene, unsubstituted arylene, and/or unsubstituted heteroarylene, respectively). In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is substituted (e.g., is a substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene, respectively).

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, wherein if the substituted moiety is substituted with a plurality of substituent groups, each substituent group may optionally be different. In embodiments, if the substituted moiety is substituted with a plurality of substituent groups, each substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one size-limited substituent group, wherein if the substituted moiety is substituted with a plurality of size-limited substituent groups, each size-limited substituent group may optionally be different. In embodiments, if the substituted moiety is substituted with a plurality of size-limited substituent groups, each size-limited substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one lower substituent group, wherein if the substituted moiety is substituted with a plurality of lower substituent groups, each lower substituent group may optionally be different. In embodiments, if the substituted moiety is substituted with a plurality of lower substituent groups, each lower substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted moiety is substituted with a plurality of groups selected from substituent groups, size-limited substituent groups, and lower substituent groups; each substituent group, size-limited substituent group, and/or lower substituent group may optionally be different. In embodiments, if the substituted moiety is substituted with a plurality of groups selected from substituent groups, size-limited substituent groups, and lower substituent groups; each substituent group, size-limited substituent group, and/or lower substituent group is different.

Preparation of Compounds

The compounds used in the reactions described herein are made according to organic synthesis techniques, starting from commercially available chemicals and/or from compounds described in the chemical literature. "Commercially available chemicals" are obtained from standard commercial sources including Acros Organics (Geel, Belgium), Aldrich Chemical (Milwaukee, Wis., including Sigma Chemical and Fluka), Apin Chemicals Ltd. (Milton Park, UK), Ark Pharm, Inc. (Libertyville, Ill.), Avocado Research (Lancashire, U.K.), BDH Inc. (Toronto, Canada), Bionet (Cornwall, U.K.), Chemservice Inc. (West Chester, Pa.), Combi-blocks (San Diego, Calif.), Crescent Chemical Co. (Hauppauge, N.Y.), eMolecules (San Diego, Calif.), Fisher Scientific Co. (Pittsburgh, Pa.), Fisons Chemicals (Leicestershire, UK), Frontier Scientific (Logan, Utah), ICN Biomedicals, Inc. (Costa Mesa, Calif.), Key Organics (Cornwall, U.K.), Lancaster Synthesis (Windham, N.H.), Matrix Scientific, (Columbia, S.C.), Maybridge Chemical Co. Ltd. (Cornwall, U.K.), Parish Chemical Co. (Orem, Utah), Pfaltz & Bauer, Inc. (Waterbury, Conn.), Polyorganix (Houston, Tex.), Pierce Chemical Co. (Rockford, Ill.), Riedel de Haen AG (Hanover, Germany), Ryan Scientific, Inc. (Mount Pleasant, S.C.), Spectrum Chemicals (Gardena, Calif.), Sundia Meditech, (Shanghai, China), TCI America (Portland, Oreg.), Trans World Chemicals, Inc. (Rockville, Md.), and WuXi (Shanghai, China).

Suitable reference books and treatise that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatise that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Specific and analogous reactants are also identified through the indices of known chemicals prepared by the Chemical Abstract Service of the American Chemical Society, which are available in most public and university libraries, as well as through on-line databases (the American Chemical Society, Washington, D.C.). Chemicals that are known but not commercially available in catalogs are prepared by custom chemical synthesis houses, where many of the standard chemical supply houses (e.g., those listed above) provide custom synthesis services. A reference for the preparation and selection of pharmaceutical salts of the pyrazole compounds described herein is P. H. Stahl & C. G. Wermuth "Handbook of Pharmaceutical Salts", Verlag Helvetica Chimica Acta, Zurich, 2002.

Isomers

Furthermore, in some embodiments, the compounds described herein exist as geometric isomers. In some embodiments, the compounds described herein possess one or more double bonds. The compounds presented herein include all cis, trans, syn, anti, entgegen (E), and zusammen (Z) isomers as well as the corresponding mixtures thereof. In some situations, compounds exist as tautomers. The compounds described herein include all possible tautomers within the formulas described herein. In some situations, the compounds described herein possess one or more chiral centers and each center exists in the R configuration, or S configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion are useful for the applications described herein. In some embodiments, the compounds described herein are prepared as their individual stereoisomers by reacting a racemic mixture of the compound with an optically active resolving agent to form a pair of diastereoisomeric compounds, separating the diastereomers and recovering the optically pure enantiomers. In some embodiments, dissociable complexes are preferred (e.g., crystalline diastereomeric salts). In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent, by any practical means that would not result in racemization.

Labeled Compounds

In some embodiments, the compounds described herein exist in their isotopically-labeled forms. In some embodiments, the methods disclosed herein include methods of treating diseases by administering such isotopically-labeled compounds. In some embodiments, the methods disclosed herein include methods of treating diseases by administering such isotopically-labeled compounds as pharmaceutical compositions. Thus, in some embodiments, the compounds disclosed herein include isotopically-labeled compounds, which are identical to those recited herein, but for the fact that one or more atoms are replaced by an atom having an atomic mass or mass number different from the atomic mass or mass number usually found in nature. Examples of isotopes that are incorporated into compounds of the invention include isotopes of hydrogen, carbon, nitrogen, oxygen, phosphorous, sulfur, fluorine and chloride, such as $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl respectively. Compounds described herein, and the metabolites, pharmaceutically acceptable salts, esters, prodrugs, solvate, hydrates or derivatives thereof which contain the aforementioned isotopes and/or other isotopes of other atoms are within the scope of this invention. Certain isotopically-labeled compounds, for example those into which radioactive isotopes such as $^3$H and $^{14}$C are incorporated, are useful in drug and/or substrate tissue distribution assays. Tritiated, i.e., $^3$H and carbon-14, i.e., $^{14}$C isotopes are particularly preferred for their ease of preparation and detectability. Further, substitution with heavy isotopes such as deuterium, i.e., $^2$H, produces certain therapeutic advantages resulting from greater metabolic stability, for example increased in vivo half-life or reduced dosage requirements. In some embodiments, the isotopically labeled compounds, pharmaceutically acceptable salt, ester, prodrug, solvate, hydrate or derivative thereof is prepared by any suitable method.

In some embodiments, the compounds described herein are labeled by other means, including, but not limited to, the use of chromophores or fluorescent moieties, bioluminescent labels, or chemiluminescent labels.

Pharmaceutically Acceptable Salts

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefore react with any of a number of inorganic or organic bases, and inorganic and organic acids, to form a pharmaceutically acceptable salt. In some embodiments, these salts are prepared in situ during the final isolation and purification of the compounds of the invention, or by separately reacting a purified compound in its free form with a suitable acid or base, and isolating the salt thus formed.

Solvates

In some embodiments, the compounds described herein exist as solvates. The invention provides for methods of treating diseases by administering such solvates. The invention further provides for methods of treating diseases by administering such solvates as pharmaceutical compositions.

Solvates contain either stoichiometric or non-stoichiometric amounts of a solvent, and, in some embodiments, are formed during the process of crystallization with pharmaceutically acceptable solvents such as water, ethanol, and the like. Hydrates are formed when the solvent is water, or alcoholates are formed when the solvent is alcohol. Solvates of the compounds described herein are conveniently prepared or formed during the processes described herein. By way of example only, hydrates of the compounds described herein are conveniently prepared by recrystallization from an aqueous/organic solvent mixture, using organic solvents including, but not limited to, dioxane, tetrahydrofuran or MeOH. In addition, the compounds provided herein exist in unsolvated as well as solvated forms. In general, the solvated forms are considered equivalent to the unsolvated forms for the purposes of the compounds and methods provided herein.

Prodrugs

In some embodiments, the compounds described herein exist in prodrug form. The invention provides for methods of treating diseases by administering such prodrugs. The invention further provides for methods of treating diseases by administering such prodrugs as pharmaceutical compositions.

In some embodiments, prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of the present invention. The amino acid residues include but are not limited to the 20 naturally occurring amino acids and also includes 4-hydroxyproline, hydroxylysine, demosine, isodemosine, 3-methylhistidine, norvaline, beta-alanine, gamma-aminobutyric acid, cirtulline, homocysteine, homoserine, ornithine and methionine sulfone. In other embodiments, prodrugs include compounds wherein a nucleic acid residue, or an oligonucleotide of two or more (e.g., two, three or four) nucleic acid residues is covalently joined to a compound of the present invention.

Pharmaceutically acceptable prodrugs of the compounds described herein also include, but are not limited to, esters, carbonates, thiocarbonates, N-acyl derivatives, N-acyloxyalkyl derivatives, quaternary derivatives of tertiary amines, N-Mannich bases, Schiff bases, amino acid conjugates, phosphate esters, metal salts and sulfonate esters. In some embodiments, compounds having free amino, amido, hydroxy or carboxylic groups are converted into prodrugs. For instance, free carboxyl groups are derivatized as amides or alkyl esters. In certain instances, all of these prodrug moieties incorporate groups including but not limited to ether, amine and carboxylic acid functionalities.

Hydroxy prodrugs include esters, such as though not limited to, acyloxyalkyl (e.g. acyloxymethyl, acyloxyethyl) esters, alkoxycarbonyloxyalkyl esters, alkyl esters, aryl esters, phosphate esters, sulfonate esters, sulfate esters and disulfide containing esters; ethers, amides, carbamates, hemisuccinates, dimethylaminoacetates and phosphoryloxymethyloxycarbonyls, as outlined in *Advanced Drug Delivery Reviews* 1996, 19, 115.

Amine derived prodrugs include, but are not limited to the following groups and combinations of groups:

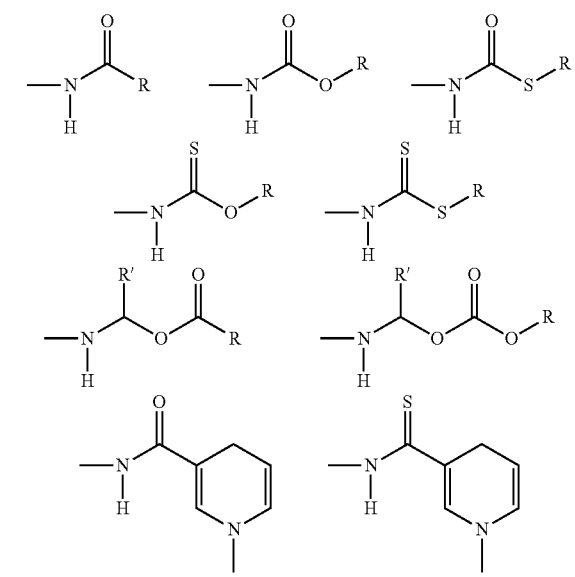

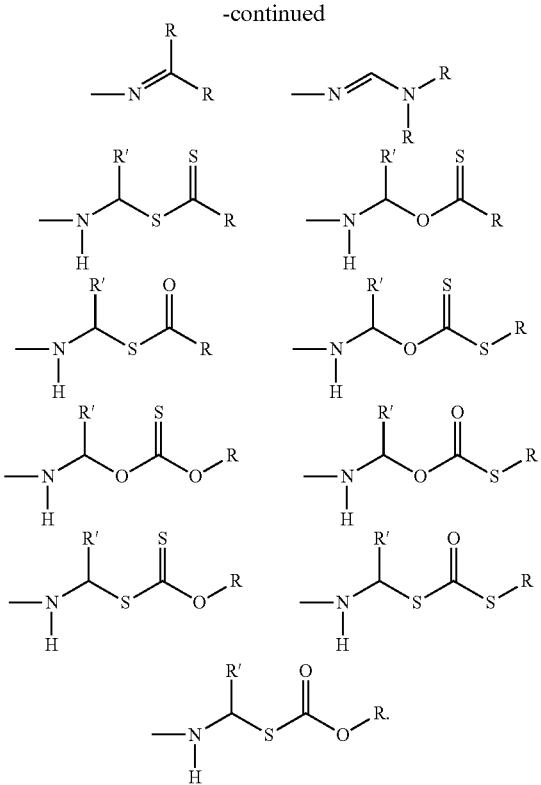

as well as sulfonamides and phosphonamides.

In certain instances, sites on any aromatic ring portions are susceptible to various metabolic reactions, therefore incorporation of appropriate substituents on the aromatic ring structures, reduce, minimize or eliminate this metabolic pathway.

Metabolites

In some embodiments, pyrazole compounds described herein are susceptible to various metabolic reactions. Therefore, in some embodiments, incorporation of appropriate substituents into the structure will reduce, minimize, or eliminate a metabolic pathway. In specific embodiments, the appropriate substituent to decrease or eliminate the susceptibility of an aromatic ring to metabolic reactions is, by way of example only, a halogen, or an alkyl group.

In additional or further embodiments, pyrazole compounds described herein are metabolized upon administration to an organism in need to produce a metabolite that is then used to produce a desired effect, including a desired therapeutic effect.

Pharmaceutical Compositions

In certain embodiments, the compound of Formula (I), (Ia), (Ib), (Ic) or (Id) as described herein is administered as a pure chemical. In some embodiments, the compound of Formula (I), (Ia), (Ib), (Ic) or (Id) described herein is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in Remington: *The Science and Practice of Pharmacy* (Gennaro, 21$^{st}$ Ed. Mack Pub. Co., Easton, Pa. (2005)).

Accordingly, provided herein is a pharmaceutical composition comprising at least one compound of Formula (I), (Ia), (Ib), (Ic) or (Id) described herein, or a stereoisomer, pharmaceutically acceptable salt, hydrate, solvate, or N-oxide thereof, together with one or more pharmaceutically acceptable carriers. The carrier(s) (or excipient(s)) is acceptable or suitable if the carrier is compatible with the other ingredients of the composition and not deleterious to the recipient (i.e., the subject) of the composition.

One embodiment provides a pharmaceutical composition comprising a pharmaceutically acceptable excipient and a compound of Formula (I), or a pharmaceutically acceptable salt thereof. One embodiment provides a pharmaceutical composition comprising a pharmaceutically acceptable excipient and a compound of Formula (Ia), or a pharmaceutically acceptable salt thereof. One embodiment provides a pharmaceutical composition comprising a pharmaceutically acceptable excipient and a compound of Formula (Ib), or a pharmaceutically acceptable salt thereof. One embodiment provides a pharmaceutical composition comprising a pharmaceutically acceptable excipient and a compound of Formula (Ic), or a pharmaceutically acceptable salt thereof. One embodiment provides a pharmaceutical composition comprising a pharmaceutically acceptable excipient and a compound of Formula (Id), or a pharmaceutically acceptable salt thereof.

Another embodiment provides a pharmaceutical composition consisting essentially of a pharmaceutically acceptable excipient and a compound of Formula (I), or a pharmaceutically acceptable salt thereof. Another embodiment provides a pharmaceutical composition consisting essentially of a pharmaceutically acceptable excipient and a compound of Formula (Ia), or a pharmaceutically acceptable salt thereof. Another embodiment provides a pharmaceutical composition consisting essentially of a pharmaceutically acceptable excipient and a compound of Formula (Ib), or a pharmaceutically acceptable salt thereof. Another embodiment provides a pharmaceutical composition consisting essentially of a pharmaceutically acceptable excipient and a compound of Formula (Ic), or a pharmaceutically acceptable salt thereof. Another embodiment provides a pharmaceutical composition consisting essentially of a pharmaceutically acceptable excipient and a compound of Formula (Id), or a pharmaceutically acceptable salt thereof.

In certain embodiments, the compound of Formula (I), (Ia), (Ib), (Ic) or (Id) as described herein is substantially pure, in that it contains less than about 5%, or less than about 1%, or less than about 0.1%, of other organic small molecules, such as contaminating intermediates or by-products that are created, for example, in one or more of the steps of a synthesis method.

These formulations include those suitable for oral, rectal, topical, buccal, parenteral (e.g., subcutaneous, intramuscular, intradermal, or intravenous) rectal, vaginal, or aerosol administration, although the most suitable form of administration in any given case will depend on the degree and severity of the condition being treated and on the nature of the particular compound being used. For example, disclosed compositions are formulated as a unit dose, and/or are formulated for oral or subcutaneous administration.

Exemplary pharmaceutical compositions are used in the form of a pharmaceutical preparation, for example, in solid, semisolid or liquid form, which includes one or more of a disclosed compound, as an active ingredient, in admixture with an organic or inorganic carrier or excipient suitable for external, enteral or parenteral applications. In some embodiments, the active ingredient is compounded, for example, with the usual non-toxic, pharmaceutically acceptable carriers for tablets, pellets, capsules, suppositories, solutions, emulsions, suspensions, and any other form suitable for use. The active object compound is included in the pharmaceutical composition in an amount sufficient to produce the desired effect upon the process or condition of the disease.

In some embodiments for preparing solid compositions such as tablets, the principal active ingredient is mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a disclosed compound or a non-toxic pharmaceutically acceptable salt thereof. When referring to these preformulation compositions as homogeneous, it is meant that the active ingredient is dispersed evenly throughout the composition so that the composition is readily subdivided into equally effective unit dosage forms such as tablets, pills and capsules.

In solid dosage forms for oral administration (capsules, tablets, pills, dragees, powders, granules and the like), the subject composition is mixed with one or more pharmaceutically acceptable carriers, such as sodium citrate or dicalcium phosphate, and/or any of the following: (1) fillers or extenders, such as starches, cellulose, microcrystalline cellulose, silicified microcrystalline cellulose, lactose, sucrose, glucose, mannitol, and/or silicic acid; (2) binders, such as, for example, carboxymethylcellulose, hypromellose, alginates, gelatin, polyvinyl pyrrolidone, sucrose and/or acacia; (3) humectants, such as glycerol; (4) disintegrating agents, such as crospovidone, croscarmellose sodium, sodium starch glycolate, agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, docusate sodium, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, in some embodiments, the compositions comprise buffering agents. In some embodiments, solid compositions of a similar type are also employed as fillers in soft and hard-filled gelatin capsules using such excipients as lactose or milk sugars, as well as high molecular weight polyethylene glycols and the like.

In some embodiments, a tablet is made by compression or molding, optionally with one or more accessory ingredients. In some embodiments, compressed tablets are prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. In some embodiments, molded tablets are made by molding in a suitable machine a mixture of the subject composition moistened with an inert liquid diluent. In some embodiments, tablets, and other solid dosage forms, such as dragees, capsules, pills and granules, are scored or prepared with coatings and shells, such as enteric coatings and other coatings.

Compositions for inhalation or insufflation include solutions and suspensions in pharmaceutically acceptable, aqueous or organic solvents, or mixtures thereof, and powders. Liquid dosage forms for oral administration include pharmaceutically acceptable emulsions, microemulsions, solutions, suspensions, syrups and elixirs. In addition to the subject composition, in some embodiments, the liquid dosage forms contain inert diluents, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, cyclodextrins and mixtures thereof.

In some embodiments, suspensions, in addition to the subject composition, contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

In some embodiments, formulations for rectal or vaginal administration are presented as a suppository, which are prepared by mixing a subject composition with one or more suitable non-irritating excipients or carriers comprising, for example, cocoa butter, polyethylene glycol, a suppository wax or a salicylate, and which is solid at room temperature, but liquid at body temperature and, therefore, will melt in the body cavity and release the active agent.

Dosage forms for transdermal administration of a subject composition include powders, sprays, ointments, pastes, creams, lotions, gels, solutions, patches and inhalants. In some embodiments, the active component is mixed under sterile conditions with a pharmaceutically acceptable carrier, and with any preservatives, buffers, or propellants as required.

In some embodiments, the ointments, pastes, creams and gels contain, in addition to a subject composition, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

In some embodiments, powders and sprays contain, in addition to a subject composition, excipients such as lactose, talc, silicic acid, aluminum hydroxide, calcium silicates and polyamide powder, or mixtures of these substances. In some embodiments, sprays additionally contain customary propellants, such as chlorofluorohydrocarbons and volatile unsubstituted hydrocarbons, such as butane and propane.

Compositions and compounds disclosed herein alternatively are administered by aerosol. This is accomplished by preparing an aqueous aerosol, liposomal preparation or solid particles containing the compound. In some embodiments, a non-aqueous (e.g., fluorocarbon propellant) suspension is used. In some embodiments, sonic nebulizers are used because they minimize exposing the agent to shear, which results in degradation of the compounds contained in the subject compositions. Ordinarily, an aqueous aerosol is made by formulating an aqueous solution or suspension of a subject composition together with conventional pharmaceutically acceptable carriers and stabilizers. The carriers and stabilizers vary with the requirements of the particular subject composition, but typically include non-ionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Pharmaceutical compositions suitable for parenteral administration comprise a subject composition in combination with one or more pharmaceutically-acceptable sterile isotonic aqueous or non-aqueous solutions, dispersions, suspensions or emulsions, or sterile powders which are reconstituted into sterile injectable solutions or dispersions just prior to use, which, in some embodiments, contain antioxidants, buffers, bacteriostats, solutes which render the formulation isotonic with the blood of the intended recipient or suspending or thickening agents.

Examples of suitable aqueous and non-aqueous carriers which are employed in the pharmaceutical compositions include water, ethanol, polyols (such as glycerol, propylene glycol, polyethylene glycol, and the like), and suitable mixtures thereof, vegetable oils, such as olive oil, and injectable organic esters, such as ethyl oleate and cyclodextrins. Proper fluidity is maintained, for example, by the use of coating materials, such as lecithin, by the maintenance of the required particle size in the case of dispersions, and by the use of surfactants Also contemplated are enteral pharmaceutical formulations including a disclosed compound and an enteric material; and a pharmaceutically acceptable carrier or excipient thereof. Enteric materials refer to polymers that are substantially insoluble in the acidic environment of the stomach, and that are predominantly soluble in intestinal fluids at specific pHs. The small intestine is the part of the gastrointestinal tract (gut) between the stomach and the large intestine, and includes the duodenum, jejunum, and ileum. The pH of the duodenum is about 5.5, the pH of the jejunum is about 6.5 and the pH of the distal ileum is about 7.5. Accordingly, enteric materials are not soluble, for example, until a pH of about 5.0, of about 5.2, of about 5.4, of about 5.6, of about 5.8, of about 6.0, of about 6.2, of about 6.4, of about 6.6, of about 6.8, of about 7.0, of about 7.2, of about 7.4, of about 7.6, of about 7.8, of about 8.0, of about 8.2, of about 8.4, of about 8.6, of about 8.8, of about 9.0, of about 9.2, of about 9.4, of about 9.6, of about 9.8, or of about 10.0. Exemplary enteric materials include cellulose acetate phthalate (CAP), hydroxypropyl methylcellulose phthalate (HP-MCP), polyvinyl acetate phthalate (PVAP), hydroxypropyl methylcellulose acetate succinate (HPMCAS), cellulose acetate trimellitate, hydroxypropyl methylcellulose succinate, cellulose acetate succinate, cellulose acetate hexahydrophthalate, cellulose propionate phthalate, cellulose acetate maleate, cellulose acetate butyrate, cellulose acetate propionate, copolymer of methylmethacrylic acid and methyl methacrylate, copolymer of methyl acrylate, methylmethacrylate and methacrylic acid, copolymer of methylvinyl ether and maleic anhydride (Gantrez ES series), ethyl methyacrylate-methylmethacrylate-chlorotrimethylammonium ethyl acrylate copolymer, natural resins such as zein, shellac and copal collophorium, and several commercially available enteric dispersion systems (e.g., Eudragit L30D55, Eudragit FS30D, Eudragit L100, Eudragit 5100, Kollicoat EMM30D, Estacryl 30D, Coateric, and Aquateric). The solubility of each of the above materials is either known or is readily determinable in vitro.

The dose of the composition comprising at least one compound of Formula (I), (Ia), (Ib), (Ic) or (Id) as described herein differs, depending upon the patient's (e.g., human) condition, that is, stage of the disease, general health status, age, and other factors.

Pharmaceutical compositions are administered in a manner appropriate to the disease to be treated (or prevented). An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity. Optimal doses are generally determined using experimental models and/or clinical trials. In some embodiments, the optimal dose depends upon the body mass, weight, or blood volume of the patient.

Oral doses typically range from about 1.0 mg to about 1000 mg, one to four times, or more, per day.

Method of Treatment

Disclosed herein are methods of inhibiting a deoxycytidine kinase (dCK) activity comprising contacting a compound detailed herein with the dexoycytidine kinase, either in vitro (e.g., in an enzymatic or an cell based assay setting) or in vivo (e.g., in animal models or an individual subject in need of treatment). Compounds provided herein bind to a deoxycytidine kinase polypeptide and inhibit its activity. Thus in another aspect, provided are methods for inhibiting dCK activity and treating diseases and disorders where dCK activity is implicated.

In some embodiments, provided is a method for treating cancer in an individual comprising administering to the individual an effective amount of a compound detailed herein, or a pharmaceutically acceptable salt thereof.

As used herein, the term "cancer" refers to all types of cancer, neoplasm, or malignant or benign tumors found in mammals, including leukemia, carcinomas and sarcomas. In some embodiments, cancer is a solid tumor cancer. In some embodiments, the cancer is metastatic. In some embodiments, the cancer is a liquid tumor cancer. In some embodiments, the liquid tumor cancer is a blood cancer. In some embodiments, the cancer is refractory. Exemplary cancers include acute myeloid leukemia ("AML"), chronic myelogenous leukemia ("CML"), and cancer of the brain, breast, pancreas, colon, liver, kidney, lung, non-small cell lung, melanoma, ovary, sarcoma, and prostate. Additional examples include, cervix cancers, stomach cancers, head & neck cancers, uterus cancers, mesothelioma, metastatic bone cancer, Medulloblastoma, Hodgkin's Disease, Non-Hodgkin's Lymphoma, multiple myeloma, neuroblastoma, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, and neoplasms of the endocrine and exocrine pancreas.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). The murine leukemia model is widely accepted as being predictive of in vivo anti-leukemic activity. It is believed that a compound that tests positive in the P388 cell assay will generally exhibit some level of anti-leukemic activity regardless of the type of leukemia being treated. Accordingly, the present invention includes a method of treating leukemia, including treating acute myeloid leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, and undifferentiated cell leukemia.

The term "sarcoma" generally refers to a tumor which is made up of a substance like the embryonic connective tissue and is generally composed of closely packed cells embedded in a fibrillar or homogeneous substance. Sarcomas which can be treated with a combination of antineoplastic thiol-binding mitochondrial oxidant and an anticancer agent include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

The term "melanoma" is taken to mean a tumor arising from the melanocytic system of the skin and other organs. Melanomas which can be treated with a combination of antineoplastic thiol-binding mitochondrial oxidant and an anticancer agent include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, and superficial spreading melanoma.

The term "carcinoma" refers to a malignant new growth made up of epithelial cells tending to infiltrate the surrounding tissues and give rise to metastases. Exemplary carcinomas which can be treated with a combination of antineoplastic thiol-binding mitochondrial oxidant and an anticancer agent include, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, and carcinoma villosum.

In some embodiments, the cancer is a liquid tumor. In some embodiments, the cancer is leukemia. In some embodiments, the cancer is acute lymphoblastic leukemia (ALL). In some embodiments, the cancer is lymphoma. In some embodiments, the cancer is a solid tumor. In some embodiments, the solid tumor is characterized by high levels of replication stress as determined by measuring gamma H2A.X expression. In some embodiments, the cancer is ovarian cancer, pancreatic cancer, lung cancer, glioblastoma, hepatocellular carcinoma, breast cancer, prostate cancer, or head and neck cancer. In some embodiments, the cancer is pancreatic cancer. In some embodiments, the cancer is ovarian cancer. In some embodiments, the cancer is lung cancer. In some embodiments, the cancer is glioblastoma. In some embodiments, the cancer is hepatocellular carcinoma. In some embodiments, the cancer is prostate cancer. In some embodiments, the cancer is head or neck cancer.

In some embodiments of this section, provided is a method for treating an immune disorder in an individual in need thereof comprising administering to the individual an effective amount of a compound detailed herein, or a pharmaceutically acceptable salt thereof. In some embodiments, the immune disorder is an autoimmune disorder or transplant rejection. In some embodiments, the autoimmune disorder is a T cell mediated autoimmune disorder. In some embodiments, the autoimmune disorder is selected from the group consisting of multiple sclerosis, lupus (including systemic lupus erythematosus), inflammatory bowel disease, rheumatoid arthritis and type 1 diabetes.

Combination Therapy

In some embodiments, provided is a method for treating cancer in an individual comprising administering to the individual an effective amount of a compound detailed herein, or a pharmaceutically acceptable salt thereof, and thymidine. In some embodiments, the compound is co-administered with thymidine. In some embodiments, the compound is administered before, during or after administration of thymidine. Examples of cancer treated include, but is not limited to leukemia, lymphoma, breast cancer, ovarian cancer, lung cancer, pancreatic cancer, hepatocellular carcinoma, melanoma, sarcoma, head and neck cancer, glioma, glioblastoma, and a cancer independent of tissue of origin that are characterized by genomic instability and/or activation of the DNA damage response. Inhibition of dCK by a compound detailed herein, or a pharmaceutically acceptable salt thereof, synergizes with thymidine to induce cell cycle arrest in tumors.

In some embodiments, the compounds described herein are used in combination with one another, with other active drugs known to be useful in treating a disease (e.g. anti-cancer agents) or with adjunctive agents that may not be effective alone, but may contribute to the efficacy of the active agent. In some embodiments, the compounds described herein are co-administered with one another or with other active drugs known to be useful in treating a disease.

"Anti-cancer agent" is used in accordance with its plain and ordinary meaning and refers to a composition (e.g. compound, drug, antagonist, inhibitor, modulator) having antineoplastic properties or the ability to inhibit the growth or proliferation of cells. In some embodiments, an anti-cancer agent is a chemotherapeutic. In some embodiments, an anti-cancer agent is an agent approved by the FDA or similar regulatory agency of a country other than the USA, for treating cancer.

Examples of anti-cancer agents include, but are not limited to, MEK (e.g. MEK1, MEK2, or MEK1 and MEK2) inhibitors (e.g. XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethylmelamine, thiotepa), alkyl sulfonates (e.g., busulfan), nitrosoureas (e.g., carmustine, lomusitne, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), or pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002, Syk inhibitors, mTOR inhibitors, antibodies (e.g., rituxan), gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (GLEEVEC®), geldanamycin, 17-N-Allylamino-17-Demethoxygeldanamycin (17-AAG), flavopiridol, LY294002, bortezomib, trastuzumab, BAY 11-7082, PKC412, PD184352, 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterium cell wall extract;

myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; iimofosine; interleukin I1 (including recombinant interleukin II, or rIL.sub.2), interferon alfa-2a; interferon alfa-2b; interferon alfa-n1; interferon alfa-n3; interferon beta-1a; interferon gamma-1b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, agents that arrest cells in the G2-M phases and/or modulate the formation or stability of microtubules, (e.g. Taxol™ (i.e. paclitaxel), Taxotere™, compounds comprising the taxane skeleton, Erbulozole (i.e. R-55104), Dolastatin 10 (i.e. DLS-10 and NSC-376128), Mivobulin isethionate (i.e. as CI-980), Vincristine, NSC-639829, Discodermolide (i.e. as NVP-XX-A-296), ABT-751 (Abbott, i.e. E-7010), Altorhyrtins (e.g. Altorhyrtin A and Altorhyrtin C), Spongistatins (e.g. Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (i.e. LU-103793 and NSC-D-669356), Epothilones (e.g. Epothilone A, Epothilone B, Epothilone C (i.e. desoxyepothilone A or dEpoA), Epothilone D (i.e. KOS-862, dEpoB, and desoxyepothilone B), Epothilone E, Epothilone F, Epothilone B N-oxide, Epothilone A N-oxide, 16-azaepothilone B, 21-aminoepothilone B (i.e. BMS-310705), 21-hydroxyepothilone D (i.e. Desoxyepothilone F and dEpoF), 26-fluoroepothilone, Auristatin PE (i.e. NSC-654663), Soblidotin (i.e. TZT-1027), LS-4559-P (Pharmacia, i.e. LS-4577), LS-4578 (Pharmacia, i.e. LS-477-P), LS-4477 (Pharmacia), LS-4559 (Pharmacia), RPR-112378 (Aventis), Vincristine sulfate, DZ-3358 (Daiichi), FR-182877 (Fujisawa, i.e. WS-9885B), GS-164 (Takeda), GS-198 (Takeda), KAR-2 (Hungarian Academy of Sciences), BSF-223651 (BASF, i.e. ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (i.e. LY-355703), AC-7739 (Ajinomoto, i.e. AVE-8063A and CS-39.HCl), AC-7700 (Ajinomoto, i.e. AVE-8062, AVE-8062A, CS-39-L-Ser.HCl, and RPR-258062A), Vitilevuamide, Tubulysin A, Canadensol, Centaureidin (i.e. NSC-106969), T-138067 (Tularik, i.e. T-67, TL-138067 and TI-138067), COBRA-1 (Parker Hughes Institute, i.e. DDE-261 and WHI-261), H10 (Kansas State University), H16 (Kansas State University), Oncocidin A1 (i.e. BTO-956 and DIME), DDE-313 (Parker Hughes Institute), Fijianolide B, Laulimalide, SPA-2 (Parker Hughes Institute), SPA-1 (Parker Hughes Institute, i.e. SPIKET-P), 3-IAABU (Cytoskeleton/Mt. Sinai School of Medicine, i.e. MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, i.e. MF-191), TMPN (Arizona State University), Vanadocene acetylacetonate, T-138026 (Tularik), Monsatrol, lnanocine (i.e. NSC-698666), 3-IAABE (Cytoskeleton/Mt. Sinai School of Medicine), A-204197 (Abbott), T-607 (Tuiarik, i.e. T-900607), RPR-115781 (Aventis), Eleutherobins (such as Desmethyleleutherobin, Desaetyleleutherobin, lsoeleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (−)-Phenylahistin (i.e. NSCL-96F037), D-68838 (Asta Medica), D-68836 (Asta Medica), Myoseverin B, D-43411 (Zentaris, i.e. D-81862), A-289099 (Abbott), A-318315 (Abbott), HTI-286 (i.e. SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi)), steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), immunostimulants (e.g., Bacillus Calmette-Guérin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-pseudomonas exotoxin conjugate, etc.), radioimmunotherapy (e.g., anti-CD20 monoclonal antibody conjugated to $^{111}$In, $^{90}$Y, or $^{131}$I, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (Iressa™), erlotinib (Tarceva™), cetuximab (Erbitux™), lapatinib (Tykerb™), panitumumab (Vectibix™) vandetanib (Caprelsa™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, or the like.

Positron Emission Tomography (PET) Probe and Imaging

Some PET probes have been previously disclosed, for example, the [$^{18}$F]L-FAC and [$^{18}$F]L-FMAC PET probes, which binds dCK, were described in U.S. Pat. No. 8,101,740, the contents of which are incorporated herein by reference.

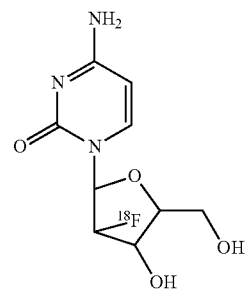

[$^{18}$F]L-FAC

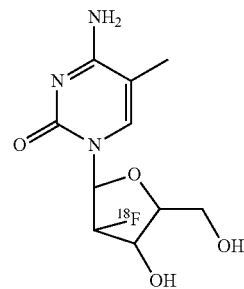

[$^{18}$F]L-FMAC

Also provided is a method of imaging, comprising: contacting a PET probe detailed herein with a biological material; using PET imaging to determine a local concentration of the compound in the biological material; and correlating the local concentration of the compound with a local immune response or the presence of neoplastic tissue. In some embodiments, contacting the compound with a biological material comprises administering a quantity of the compound to an animal or human; and correlating the local concentration of the compound in the animal or human with a local immune response or neoplastic tissue in the animal or human. In some embodiments, the method further comprising using the local concentration of the compound to diagnose cancer and/or monitor cancer treatment. In some embodiments, the animal or human has a condition selected from the group consisting of cancer, an autoimmune disorder, a development disorder, viral infection, bacterial infection, parasitical infection, infection, a metabolic disease, and inflammation. In some embodiments, the animal or human has a condition selected from the group consisting of lymphadenopathy, melanoma, leukemia, and glioma. In some embodiments, the animal or human has a condition selected from the group consisting of rheumatoid arthritis, inflammatory bowel disease, Experimental Autoimmune Encephalomyelitis (EAE), multiple sclerosis, type 1 diabetes, and atherosclerosis. In some embodiments, the animal or human is undergoing a therapy selected from the group consisting of cancer immunotherapy, immunotherapy, interferon therapy, vaccination, radiation therapy, chemotherapy, and antibiotic therapy. In some embodiments, contacting the compound with a biological material comprises administering a quantity of the compound to an animal or human; and correlating the local concentration of the compound in the animal or human with abnormal activity in an organ or portion of the lymphatic system, for example, a lymph node or the spleen. In one variation, the method further comprises correlating the local concentration of the compound with a lymphoma lesion or a malignant lymphoid disease. In some embodiments, the local immune response is the accumulation of activated T lymphocytes. In one variation, the activated T lymphocytes take up more compound per cell than non-activated T lymphocytes.

Also provided is a method of predicting resistance to an oncolytic agent, comprising: contacting a PET probe detailed herein with a neoplasm; using PET imaging to determine a local concentration of the compound in the neoplasm; comparing the local concentration of the compound with a baseline level; correlating a local concentration of the compound substantially lower than the baseline level with low dCK expression of the neoplasm; correlating low dCK expression of the neoplasm with oncolytic nucleoside analog resistance, wherein the baseline level corresponds to a measured concentration of the compound in representative neoplastic cells that express dCK, concentration of the compound in representative neoplastic cells that do not express dCK, or a weighted average. In some embodiments, the neoplasm is of the T lymphocyte lineage. In some embodiments, the neoplasm is selected from the group consisting of leukemia, acute non-lymphocytic leukemia, acute lymphocytic leukemia, blast phase of chronic myelocytic leukemia, meningeal leukemia, pancreatic cancer, ovarian cancer, breast cancer, non-small cell lung cancer, B-cell chronic lymphocytic leukemia, hairy cell leukemia, relapsed acute lymphoblastic leukemia, and refractory acute lymphoblastic leukemia cells.

Also provided is a method for evaluating efficacy of a dCK inhibitor compound, comprising: administering a dCK inhibitor compound to an individual; providing an $^{18}$F-FAC PET probe to the individual; imaging to determine a local concentration of the $^{18}$F-FAC PET probe; and correlating the local concentration of the $^{18}$F-FAC PET probe with efficacy of the dCK inhibitor compound. In some embodiments, the individual is a mammal, such as an experimental mouse used in an animal model for testing dCK inhibition. The method provides an efficient way of screening for in vivo efficacy of compounds in animal models. IN some embodiments, the method is applied to any dCK inhibitors such as the dCK inhibitor compounds detailed herein, or a pharmaceutically acceptable salt thereof.

EMBODIMENTS

Embodiments contemplated herein include embodiments P1 to P43 following.

Embodiment P1

A compound of Formula (I), or a pharmaceutically acceptable salt or solvate thereof:

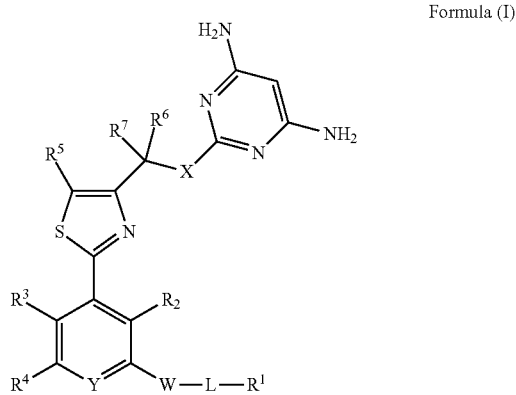

Formula (I)

wherein: W is —O—, —S—, or —N(R$^8$)—; L is optionally substituted alkylene, optionally substituted alkenylene, or optionally substituted alkynylene; X is —CH$_2$—, —O—, —N(R$^8$)—, —S—, —S(O)—, or —S(O)$_2$—; Y is N or C(R$^9$); R$^1$ is optionally substituted heterocycloalkyl; R$^2$, R$^3$, R$^4$ are independently hydrogen, halogen, —CN, —N$_3$, —CF$_3$, —CCl$_3$, —CBr$_3$, —CI$_3$, —CN, —C(O)H, —OH, —NH$_2$, —C(O)OH, —C(O)NH$_2$, —NO$_2$, —SH, optionally substituted alkyl, optionally substituted heteroalkyl, optionally substituted heterocycloalkyl, optionally substituted aryl, optionally substituted heteroaryl, optionally substituted alkoxy, or optionally substituted cycloalkyl; R$^5$ is hydrogen, halogen, —CN, —N$_3$, —CF$_3$, —CCl$_3$, —CBr$_3$, —CI$_3$, —CN, —C(O)H, —OH, —NH$_2$, —C(O)OH, —C(O)NH$_2$, —NO$_2$, —SH, optionally substituted alkyl, optionally substituted heteroalkyl, optionally substituted heterocycloalkyl, optionally substituted alkoxy, optionally substituted cycloalkyl, optionally substituted aryl, or optionally substituted heteroaryl; R$^6$ and R$^7$ are independently hydrogen, halogen, or optionally substituted alkyl; or R$^6$ and R$^7$ are taken together with the carbon to which they are attached to form a cycloalkyl; R$^8$ is hydrogen or optionally substituted alkyl; and R$^9$ is hydrogen, halogen, —CN, —N$_3$, —CF$_3$, —CCl$_3$, —CBr$_3$, —CI$_3$, —CN, —C(O)H, —OH, —NH$_2$, —C(O)OH, —C(O)NH$_2$, —NO$_2$, —SH, optionally substituted alkyl, optionally substituted heteroalkyl, optionally substituted heterocycloalkyl, optionally substituted aryl, optionally substituted heteroaryl, optionally substituted alkoxy, or optionally substituted cycloalkyl.

Embodiment P2

The compound of embodiment P1, wherein R$^2$ and R$^3$ are hydrogen.

Embodiment P3

The compound of any one of embodiments P1 to P2, wherein R$^4$ is hydrogen or halogen.

Embodiment P4

The compound of any one of embodiments P1 to P3, wherein R$^4$ is hydrogen.

Embodiment P5

The compound of any one of embodiments P1 to P4, wherein R$^6$ and R$^7$ are independently hydrogen or optionally substituted alkyl.

Embodiment P6

The compound of any one of embodiments P1 to P5, wherein R$^7$ is hydrogen.

Embodiment P7

The compound of embodiment P6, wherein the compound of Formula (I) is a compound of Formula (Ia):

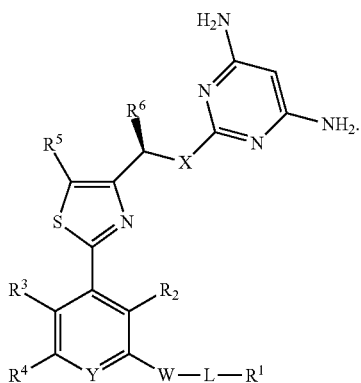

Formula (Ia)

Embodiment P8

The compound of embodiment P6, wherein the compound of Formula (I) is a compound of Formula (Ib):

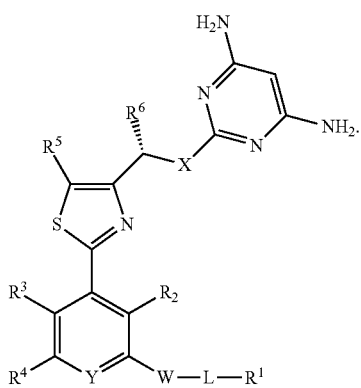

Formula (Ib)

Embodiment P9

The compound of any one of embodiments P1 to P8, wherein $R^6$ is optionally substituted alkyl.

Embodiment P10

The compound of embodiment P1 to P9, wherein $R^6$ is methyl, ethyl, or propyl.

Embodiment P11

The compound of embodiment P1 to P10, wherein $R^6$ is methyl.

Embodiment P12

The compound of any one of embodiments P1 to P4, wherein $R^6$ and $R^7$ are not both hydrogen.

Embodiment P13

The compound of any one of embodiments P1 to P4, wherein $R^6$ and $R^7$ are taken together with the carbon to which they are attached to form a cycloalkyl.

Embodiment P14

The compound of any one of embodiments P1 to P13, wherein $R^5$ is optionally substituted alkyl.

Embodiment P15

The compound of any one of embodiments P1 to P14, wherein $R^5$ is methyl, ethyl, propyl, or butyl.

Embodiment P16

The compound of any one of embodiments P1 to P15, wherein $R^5$ is methyl.

Embodiment P17

The compound of any one of embodiments P1 to P16, wherein X is —S—.

Embodiment P18

The compound of any one of embodiments P1 to P16, wherein X is —CH$_2$—.

Embodiment P19

The compound of any one of embodiments P1 to P18, wherein Y is N.

Embodiment P20

The compound of any one of embodiments P1 to P18, wherein Y is C($R^9$).

Embodiment P21

The compound of embodiment P19, wherein $R^9$ is hydrogen, optionally substituted alkyl, or optionally substituted alkoxy.

Embodiment P22

The compound of any one of embodiments P19 to P21, wherein $R^9$ is optionally substituted alkoxy.

Embodiment P23

The compound of any one of embodiments P19 to P22, wherein $R^9$ is methoxy, ethoxy, or propoxy.

Embodiment P24

The compound of any one of embodiments P19 to P23, wherein $R^9$ is methoxy.

Embodiment P25

The compound of any one of embodiments P1 to P24, wherein W is —O—.

Embodiment P26

The compound of any one of embodiments P1 to P25, wherein L is optionally substituted alkylene.

Embodiment P27

The compound of any one of embodiments P1 to P26, wherein L is —CH$_2$CH$_2$—.

Embodiment P28

The compound of any one of embodiments P1 to P27, wherein R$^1$ is a 5-membered optionally substituted heterocycloalkyl.

Embodiment P29

The compound of any one of embodiments P1 to P28, wherein R$^1$ is pyrrolidinyl.

Embodiment P30

The compound of any one of embodiments P1 to P27, wherein R$^1$ is a 6-membered optionally substituted heterocycloalkyl.

Embodiment P31

The compound of any one of embodiments P1 to P27 or P30, wherein R$^1$ is piperidinyl, piperizanyl, or morpholinyl.

Embodiment P32

The compound of any one of embodiments P1 to P27 or P30 to P31, wherein R$^1$ is morpholinyl.

Embodiment P33

The compound of any one of embodiments P1 to P32, wherein the compound of Formula (I) is selected from:

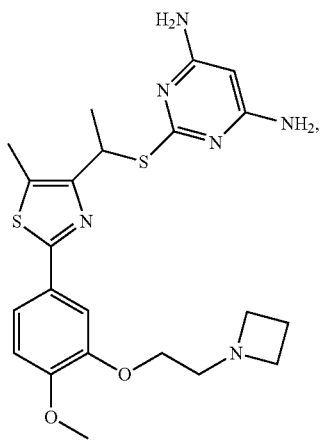

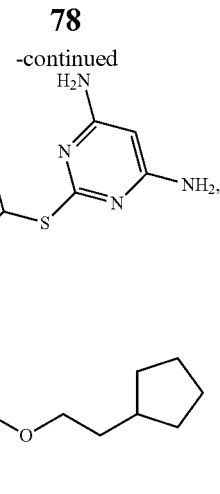

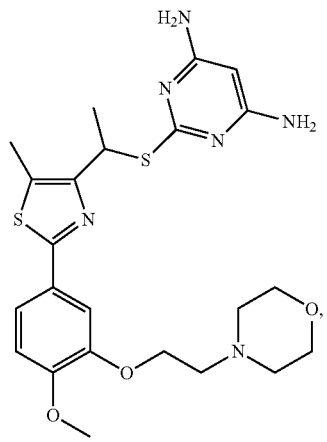

79
-continued
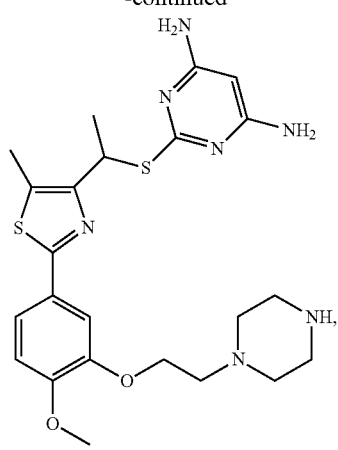
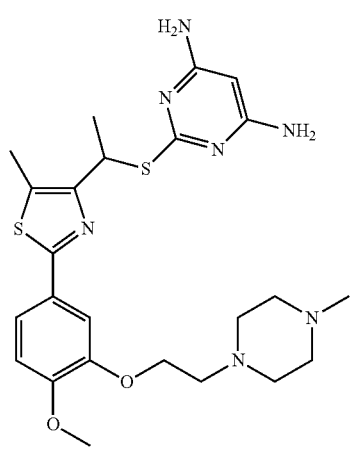
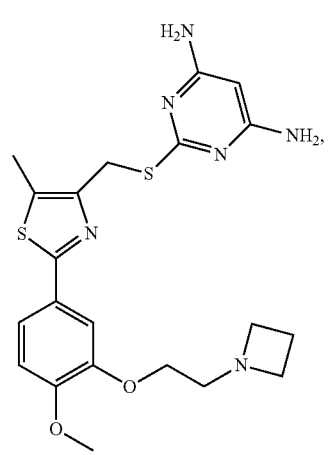
80
-continued
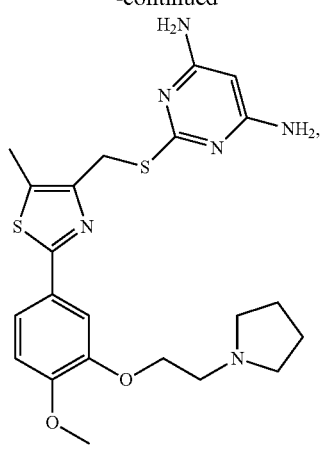
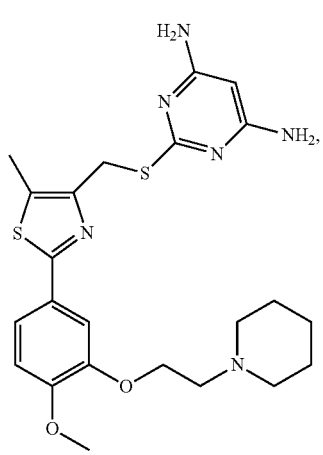
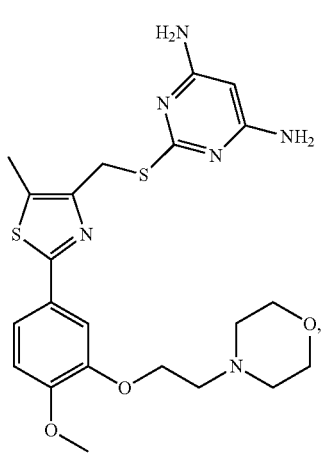

81
-continued
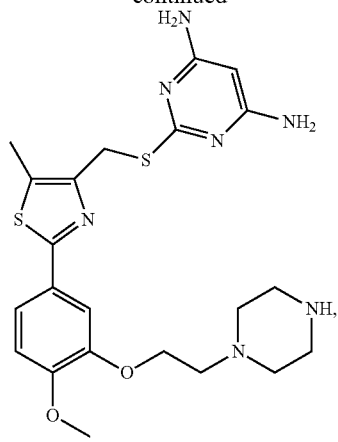
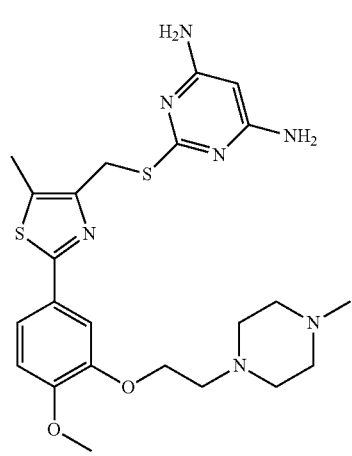
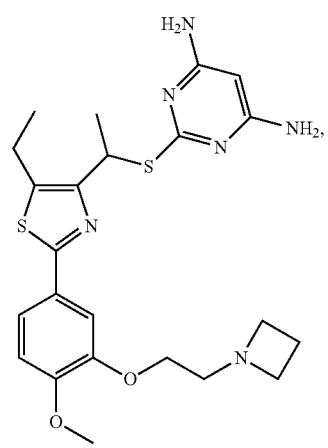
82
-continued
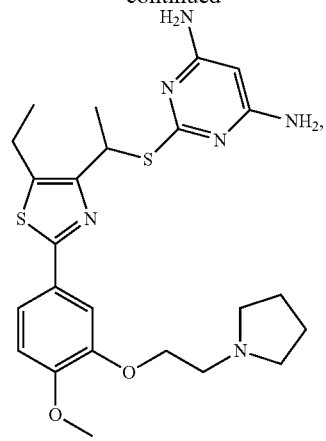
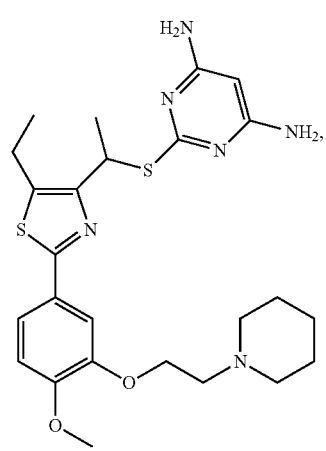
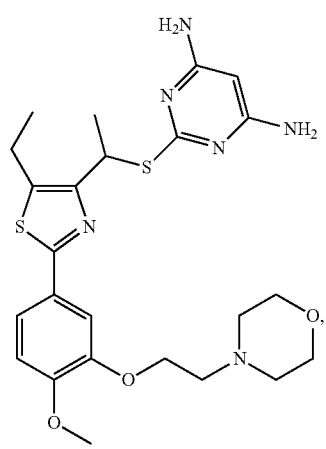

83
-continued
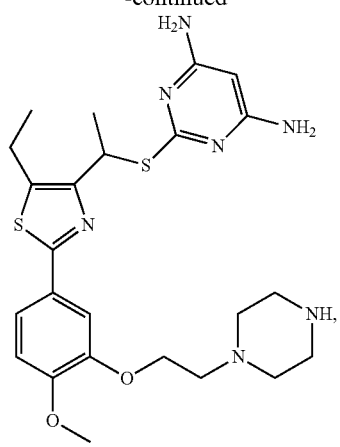
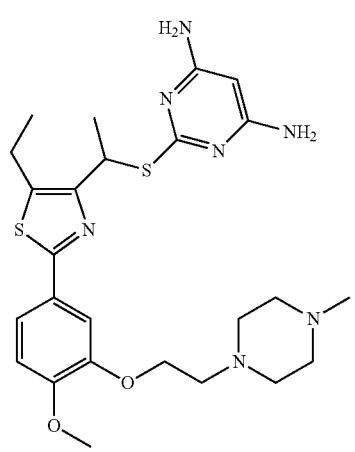
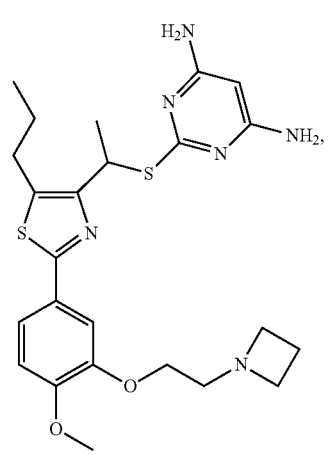
84
-continued
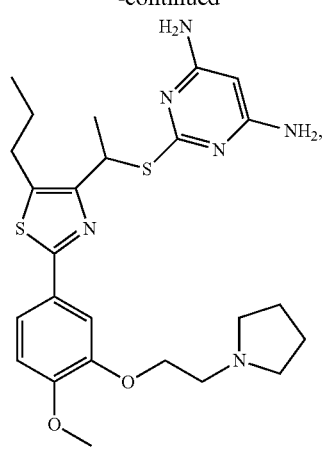
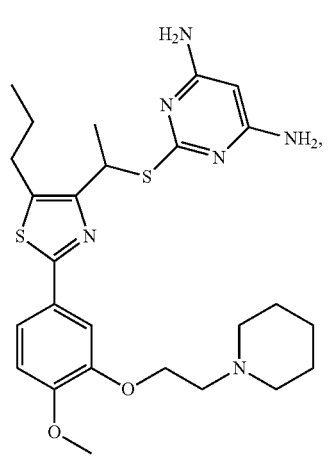
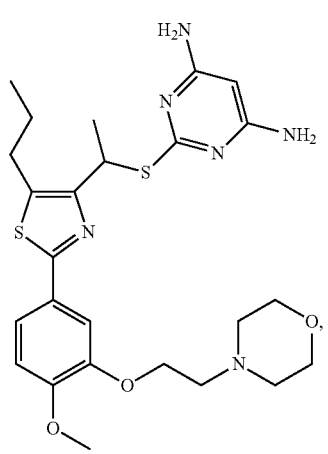

85
-continued
86
-continued
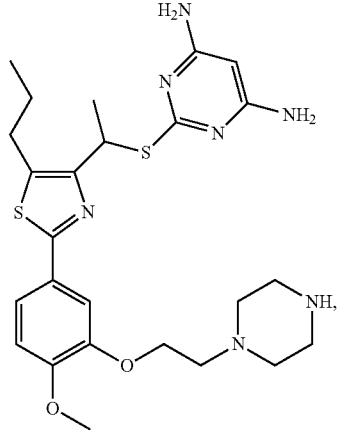
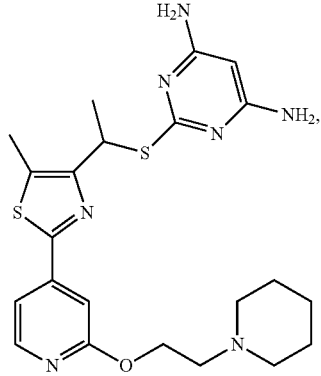

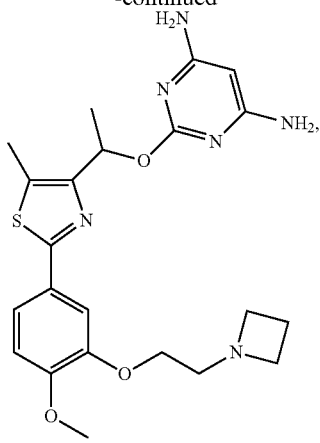

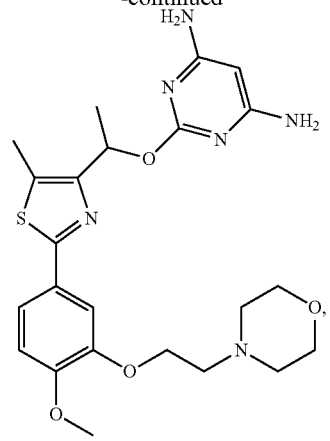

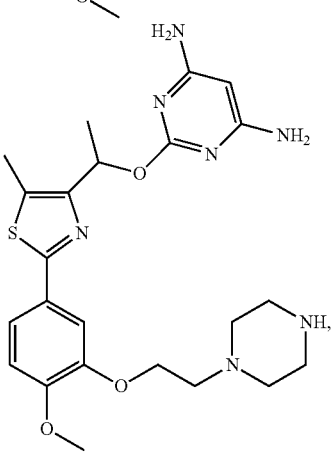

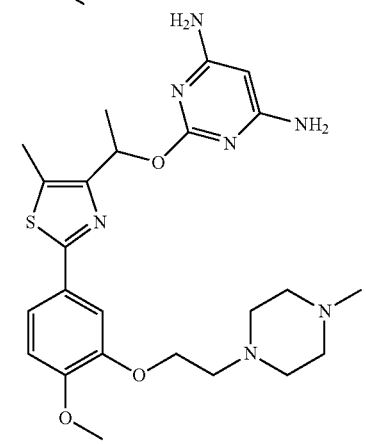

Embodiment P34

The compound of embodiment P1, wherein W is —O—, —S—, or —N(R$^8$)—; L is optionally substituted alkylene, optionally substituted alkenylene, or optionally substituted alkynylene; X is —CH$_2$—, —O—, —N(R$^8$)—, —S—, —S(O)—, or —S(O)$_2$—; Y is N or C(R$^9$); R$^1$ is optionally substituted heterocycloalkyl; R$^2$, R$^3$, R$^4$ are independently hydrogen, halogen, —CN, optionally substituted alkyl, optionally substituted alkoxy, or optionally substituted cycloalkyl; R$^5$ is hydrogen, halogen, optionally substituted alkyl, optionally substituted alkoxy, optionally substituted cycloalkyl, optionally substituted aryl, or optionally substituted heteroaryl; $R^6$ and $R^7$ are independently hydrogen, halogen, or optionally substituted alkyl; or $R^6$ and $R^7$ are taken together with the carbon to which they are attached to form a cycloalkyl; $R^8$ is hydrogen or optionally substituted alkyl; and $R^9$ is hydrogen, halogen, —CN, optionally substituted alkyl, optionally substituted alkoxy, or optionally substituted cycloalkyl.

Embodiment P35

A pharmaceutical composition, comprising a compound of any one of embodiments P1 to P34 or a pharmaceutically acceptable salt or solvate thereof, and a pharmaceutically acceptable excipient.

Embodiment P36

A method for inhibiting a deoxycytidine kinase (dCK) activity, comprising contacting a deoxycytidine kinase with an effective amount of a compound of any one of embodiments P1 to P34 thereby inhibiting said deoxycytidine kinase.

Embodiment P37

A method of treating cancer in a subject in need thereof, comprising administering to the subject an effective amount of the compound of any one of embodiments P1 to P34.

Embodiment P38

A method of treating cancer in a subject in need thereof, comprising administering to the subject a pharmaceutical composition of embodiment P35.

Embodiment P39

The method of any one of embodiments P37 to P38, wherein the cancer is a solid tumor cancer.

Embodiment P40

The method of embodiment P39, wherein the solid tumor cancer is ovarian cancer, pancreatic cancer, lung cancer, glioblastoma, hepatocellular carcinoma, breast cancer, prostate cancer or head and neck cancer.

Embodiment P41

The method of any one of embodiments P37 to P38, wherein the cancer is a liquid tumor cancer.

Embodiment P42

The method of embodiment P41, wherein the liquid tumor cancer is a blood cancer.

Embodiment P43

The method of any one of embodiments P41 to P42, wherein the cancer is leukemia or lymphoma.

Further embodiments contemplated herein include embodiments 1 to 43 following.

Further embodiments contemplated herein include embodiments 1 to 43 following.

Embodiment 1

A compound of Formula (I), or a pharmaceutically acceptable salt or solvate thereof:

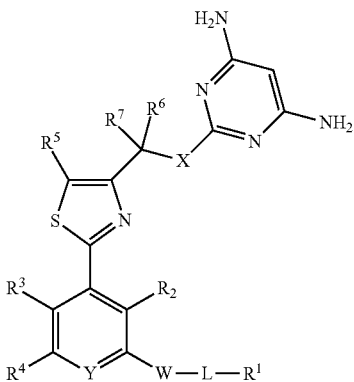

Formula (I)

wherein: W is —O—, —S—, or —N($R^8$)—; L is optionally substituted alkylene, optionally substituted alkenylene, or optionally substituted alkynylene; X is —$CH_2$—, —O—, —N($R^8$)—, —S—, —S(O)—, or —S(O)$_2$—; Y is N or C($R^9$); $R^1$ is optionally substituted heterocycloalkyl; $R^2$, $R^3$, $R^4$ are independently hydrogen, halogen, —CN, —$N_3$, —$CF_3$, —$CCl_3$, —$CBr_3$, —$CI_3$, —CN, —C(O)H, —OH, —$NH_2$, —C(O)OH, —C(O)$NH_2$, —$NO_2$, —SH, optionally substituted alkyl, optionally substituted heteroalkyl, optionally substituted heterocycloalkyl, optionally substituted aryl, optionally substituted heteroaryl, optionally substituted alkoxy, or optionally substituted cycloalkyl; $R^5$ is hydrogen, halogen, —CN, —$N_3$, —$CF_3$, —$CCl_3$, —$CBr_3$, —$CI_3$, —CN, —C(O)H, —OH, —$NH_2$, —C(O)OH, —C(O)$NH_2$, —$NO_2$, —SH, optionally substituted alkyl, optionally substituted heteroalkyl, optionally substituted heterocycloalkyl, optionally substituted alkoxy, optionally substituted cycloalkyl, optionally substituted aryl, or optionally substituted heteroaryl; $R^6$ and $R^7$ are independently hydrogen, halogen, or optionally substituted alkyl; or $R^6$ and $R^7$ are taken together with the carbon to which they are attached to form a cycloalkyl; $R^8$ is hydrogen or optionally substituted alkyl; and $R^9$ is hydrogen, halogen, —CN, —$N_3$, —$CF_3$, —$CCl_3$, —$CBr_3$, —$CI_3$, —CN, —C(O)H, —OH, —$NH_2$, —C(O)OH, —C(O)$NH_2$, —$NO_2$, —SH, optionally substituted alkyl, optionally substituted heteroalkyl, optionally substituted heterocycloalkyl, optionally substituted aryl, optionally substituted heteroaryl, optionally substituted alkoxy, or optionally substituted cycloalkyl.

Embodiment 2

The compound of embodiment 1, wherein $R^2$ and $R^3$ are hydrogen.

Embodiment 3

The compound of any one of embodiments 1 to 2, wherein $R^4$ is hydrogen or halogen.

Embodiment 4

The compound of any one of embodiments 1 to 3, wherein $R^4$ is hydrogen.

Embodiment 5

The compound of any one of embodiments 1 to 4, wherein $R^6$ and $R^7$ are independently hydrogen or optionally substituted alkyl.

Embodiment 6

The compound of any one of embodiments 1 to 5, wherein $R^7$ is hydrogen.

Embodiment 7

The compound of embodiment 6, wherein the compound of Formula (I) is a compound of Formula (Ia):

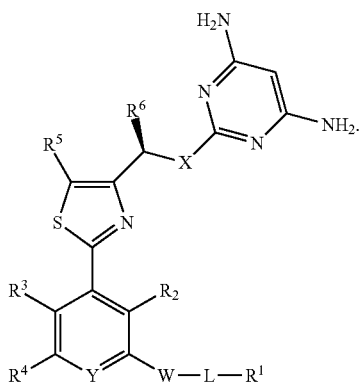

Formula (Ia)

Embodiment 8

The compound of embodiment 6, wherein the compound of Formula (I) is a compound of Formula (Ib):

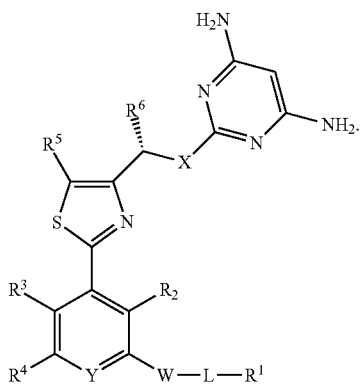

Formula (Ib)

Embodiment 9

The compound of any one of embodiments 1 to 8, wherein $R^6$ is optionally substituted alkyl.

Embodiment 10

The compound of embodiment 1 to 9, wherein $R^6$ is methyl, ethyl, or propyl.

Embodiment 11

The compound of embodiment 1 to 10, wherein $R^6$ is methyl.

Embodiment 12

The compound of any one of embodiments 1 to 4, wherein $R^6$ and $R^7$ are not both hydrogen.

Embodiment 13

The compound of any one of embodiments 1 to 4, wherein $R^6$ and $R^7$ are taken together with the carbon to which they are attached to form a cycloalkyl.

Embodiment 14

The compound of any one of embodiments 1 to 13, wherein $R^5$ is optionally substituted alkyl.

Embodiment 15

The compound of any one of embodiments 1 to 14, wherein $R^5$ is methyl, ethyl, propyl, or butyl.

Embodiment 16

The compound of any one of embodiments 1 to 15, wherein $R^5$ is methyl.

Embodiment 17

The compound of any one of embodiments 1 to 16, wherein X is —S—.

Embodiment 18

The compound of any one of embodiments 1 to 16, wherein X is —$CH_2$—.

Embodiment 19

The compound of any one of embodiments 1 to 18, wherein Y is N.

Embodiment 20

The compound of any one of embodiments 1 to 18, wherein Y is $C(R^9)$.

Embodiment 21

The compound of embodiment 19, wherein $R^9$ is hydrogen, optionally substituted alkyl, or optionally substituted alkoxy.

Embodiment 22

The compound of any one of embodiments 19 to 21, wherein $R^9$ is optionally substituted alkoxy.

Embodiment 23

The compound of any one of embodiments 19 to 22, wherein $R^9$ is methoxy, ethoxy, or propoxy.

Embodiment 24

The compound of any one of embodiments 19 to 23, wherein $R^9$ is methoxy.

Embodiment 25

The compound of any one of embodiments 1 to 24, wherein W is —O—.

Embodiment 26

The compound of any one of embodiments 1 to 25, wherein L is optionally substituted alkylene.

Embodiment 27

The compound of any one of embodiments 1 to 26, wherein L is —CH$_2$CH$_2$—.

Embodiment 28

The compound of any one of embodiments 1 to 27, wherein $R^1$ is a 5-membered optionally substituted heterocycloalkyl.

Embodiment 29

The compound of any one of embodiments 1 to 28, wherein $R^1$ is pyrrolidinyl.

Embodiment 30

The compound of any one of embodiments 1 to 27, wherein $R^1$ is a 6-membered optionally substituted heterocycloalkyl.

Embodiment 31

The compound of any one of embodiments 1 to 27 or 30, wherein $R^1$ is piperidinyl, piperizanyl, or morpholinyl.

Embodiment 32

The compound of any one of embodiments 1 to 27 or 30 to 31, wherein $R^1$ is morpholinyl.

Embodiment 33

The compound of any one of embodiments 1 to 32, wherein the compound of Formula (I) is selected from:

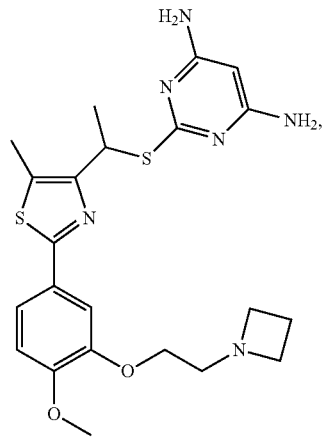

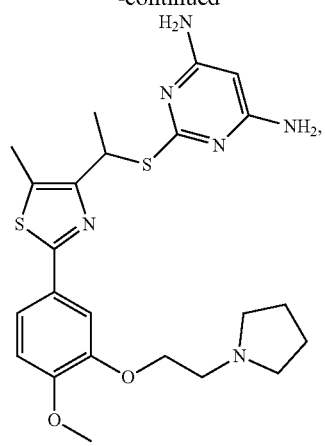

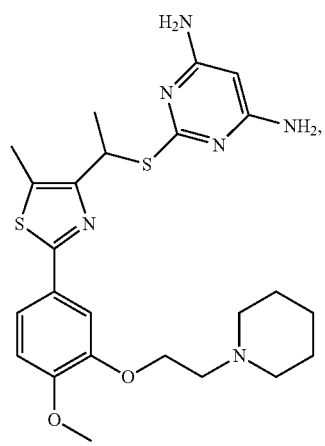

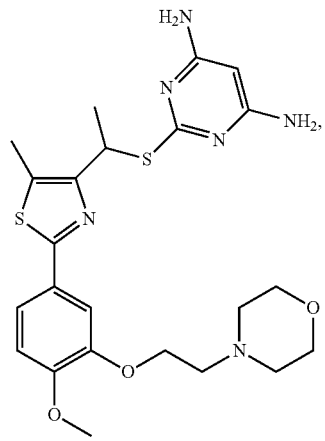

95
-continued
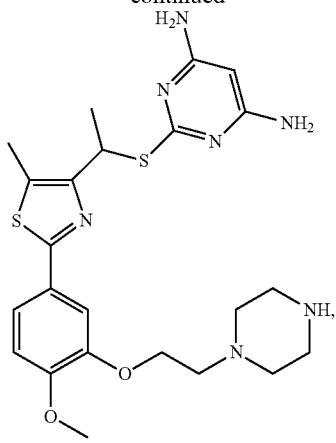
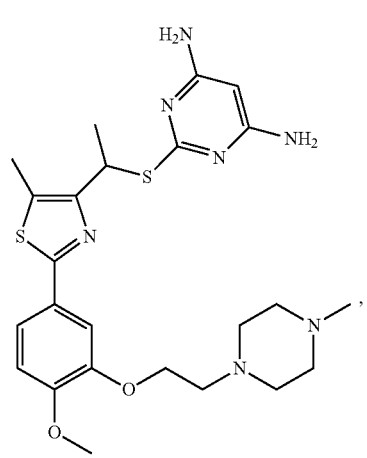
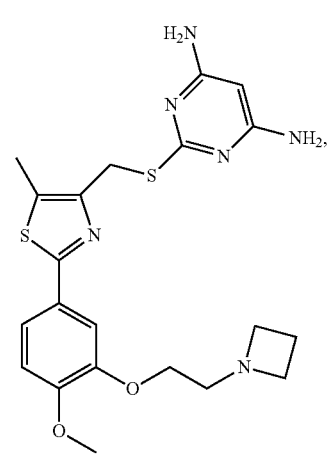
96
-continued
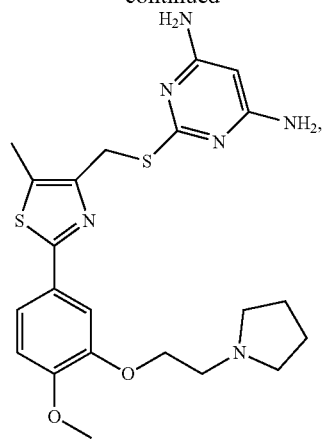
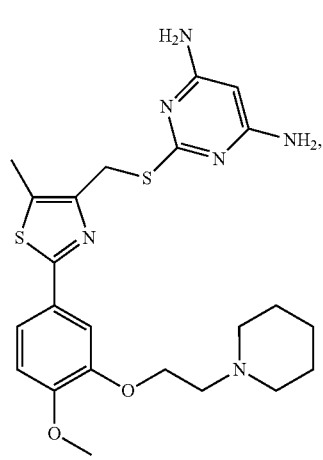
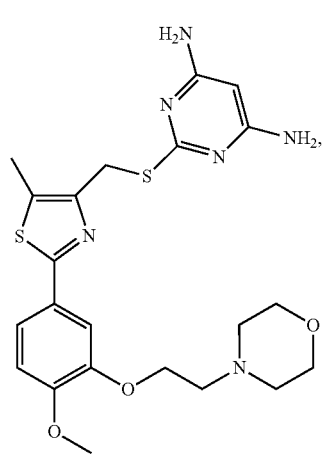

97 -continued
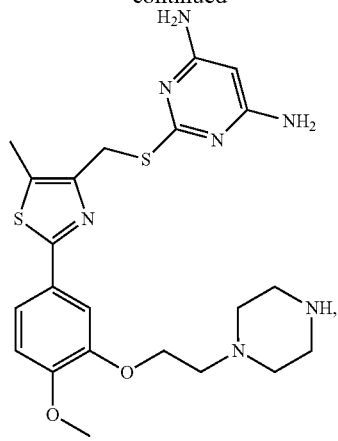
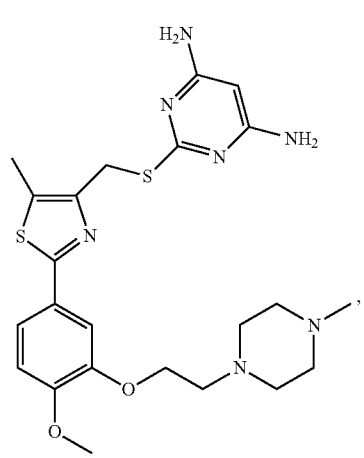
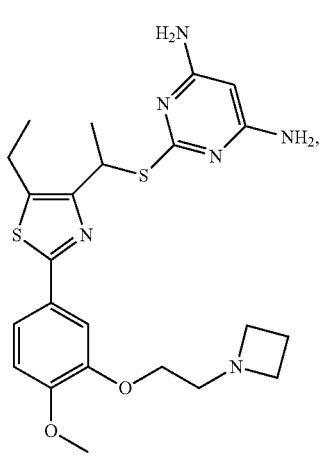
98 -continued
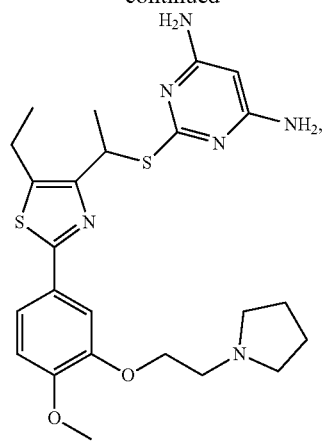
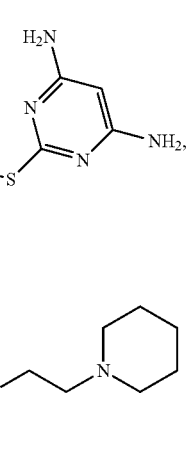
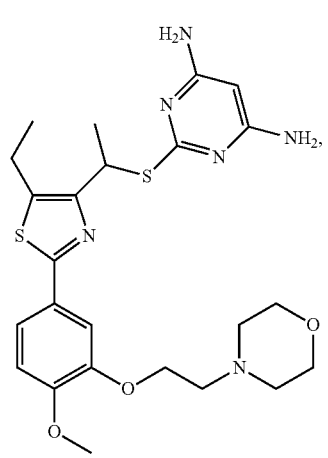

-continued
99
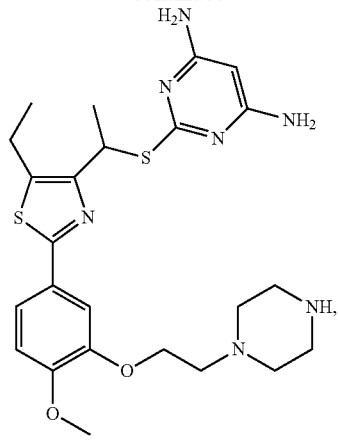
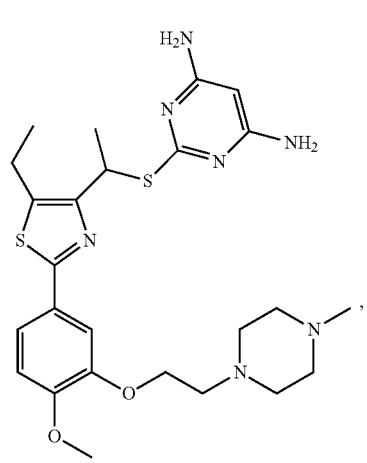
100
-continued
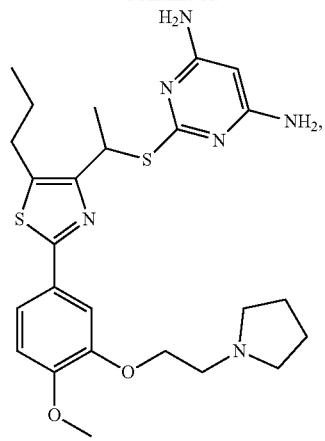
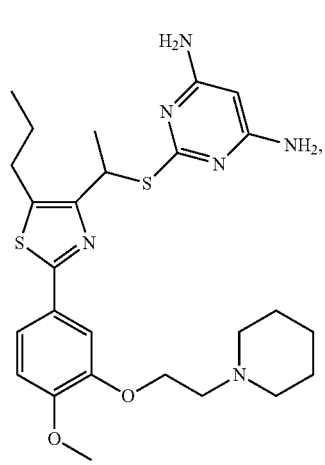
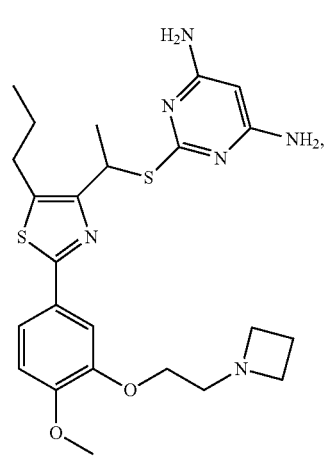
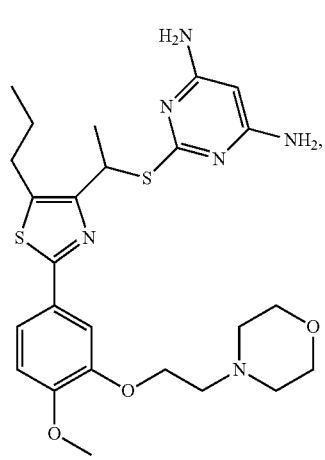

-continued
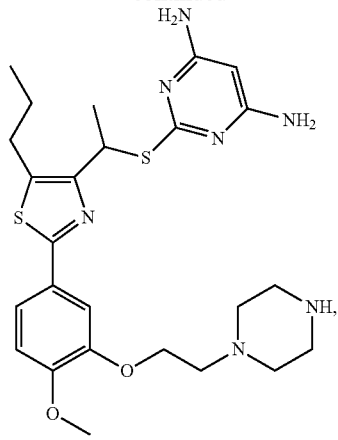
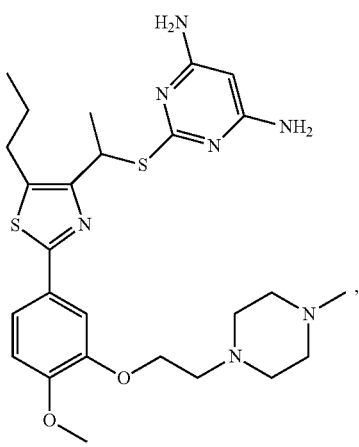
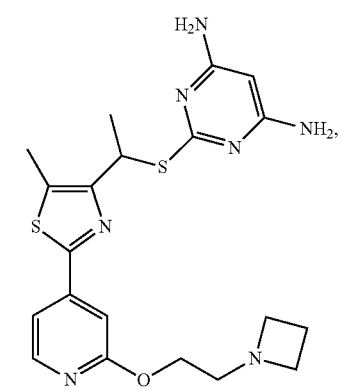
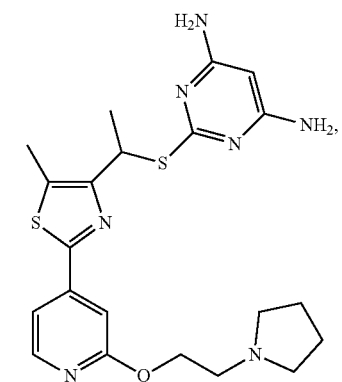
-continued
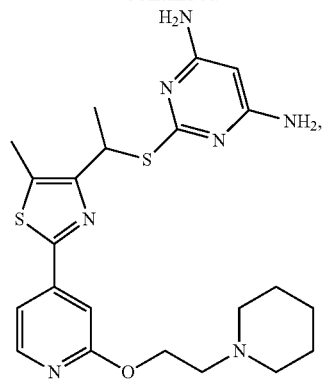
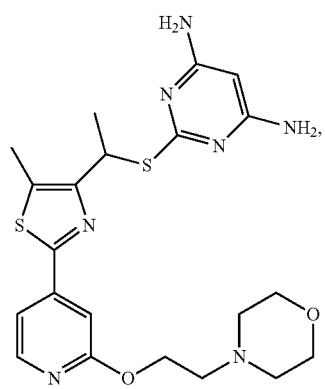
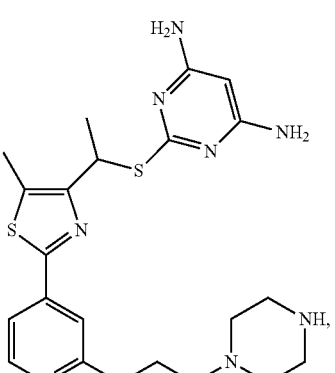
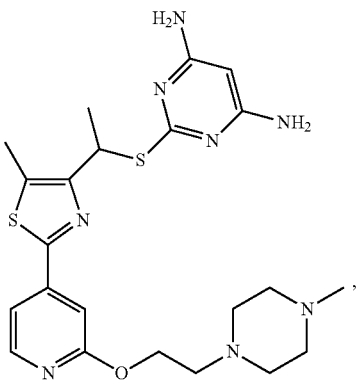

-continued

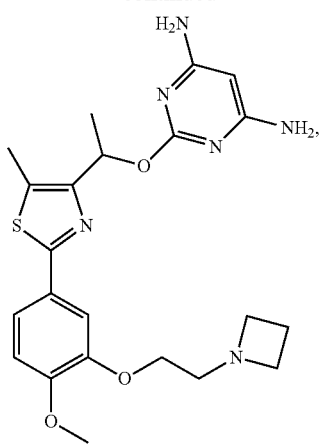

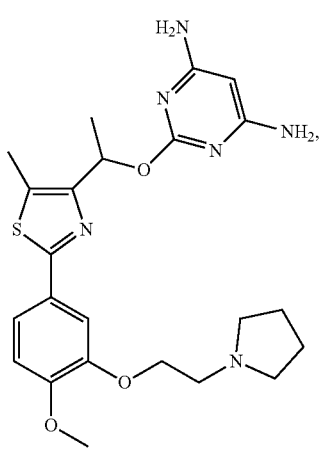

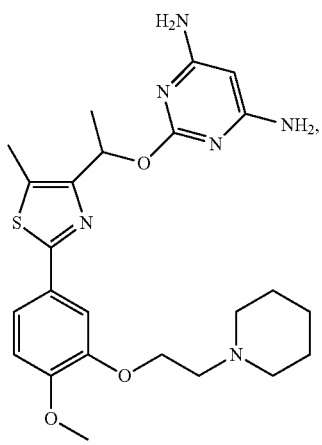

-continued

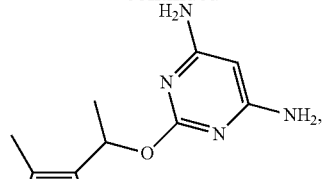

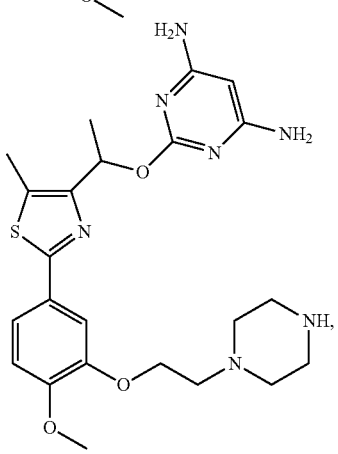

and

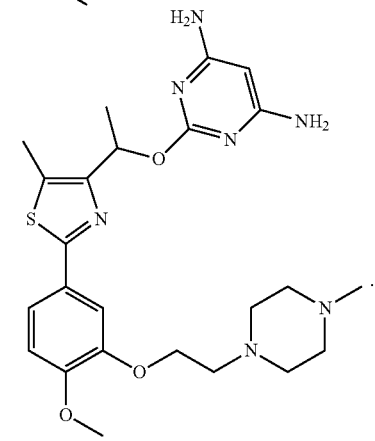

Embodiment 34

The compound of embodiment 1, wherein W is —O—, —S—, or —N(R$^8$)—; L is optionally substituted alkylene, optionally substituted alkenylene, or optionally substituted alkynylene; X is —CH$_2$—, —O—, —N(R$^8$)—, —S—, —S(O)—, or —S(O)$_2$—; Y is N or C(R$^9$); R$^1$ is optionally substituted heterocycloalkyl; R$^2$, R$^3$, R$^4$ are independently hydrogen, halogen, —CN, optionally substituted alkyl, optionally substituted alkoxy, or optionally substituted cycloalkyl; R$^5$ is hydrogen, halogen, optionally substituted alkyl, optionally substituted alkoxy, optionally substituted cycloalkyl, optionally substituted aryl, or optionally substituted heteroaryl; R$^6$ and R$^7$ are independently hydrogen, halogen, or optionally substituted alkyl; or R$^6$ and R$^7$ are taken together with the carbon to which they are attached to form a cycloalkyl; R⁸ is hydrogen or optionally substituted alkyl; and R⁹ is hydrogen, halogen, —CN, optionally substituted alkyl, optionally substituted alkoxy, or optionally substituted cycloalkyl.

Embodiment 35

A pharmaceutical composition, comprising a compound of any one of embodiments 1 to 34 or a pharmaceutically acceptable salt or solvate thereof, and a pharmaceutically acceptable excipient.

Embodiment 36

A method for inhibiting a deoxycytidine kinase (dCK) activity, comprising contacting a deoxycytidine kinase with an effective amount of a compound of any one of embodiments 1 to 34 thereby inhibiting said deoxycytidine kinase.

Embodiment 37

A method of treating cancer in a subject in need thereof, comprising administering to the subject an effective amount of the compound of any one of embodiments 1 to 34.

Embodiment 38

A method of treating cancer in a subject in need thereof, comprising administering to the subject a pharmaceutical composition of embodiment 35.

Embodiment 39

The method of any one of embodiments 37 to 38, wherein the cancer is a solid tumor cancer.

Embodiment 40

The method of embodiment 39, wherein the solid tumor cancer is ovarian cancer, pancreatic cancer, lung cancer, glioblastoma, hepatocellular carcinoma, breast cancer, prostate cancer or head and neck cancer.

Embodiment 41

The method of any one of embodiments 37 to 38, wherein the cancer is a liquid tumor cancer.

Embodiment 42

The method of embodiment 41, wherein the liquid tumor cancer is a blood cancer.

Embodiment 43

The method of any one of embodiments 41 to 42, wherein the cancer is leukemia or lymphoma.

EXAMPLES

The following examples illustrate certain specific embodiments of the invention and are not meant to limit the scope of the invention.

Embodiments herein are further illustrated by the following examples and detailed protocols. However, the examples are merely intended to illustrate embodiments and are not to be construed to limit the scope herein. The contents of all references and published patents and patent applications cited throughout this application are hereby incorporated by reference.

EXAMPLES

General Synthetic Methods

Unless otherwise noted, reagents and solvents were used as received from commercial suppliers. Anhydrous solvents and oven-dried glassware were used for synthetic transformations sensitive to moisture and/or oxygen. Yields were not optimized. Reaction times are approximate and were not optimized. Column chromatography and thin layer chromatography (TLC) were performed on silica gel unless otherwise noted. In some instances, compounds were purified using preparative HPLC. Spectra are given in ppm (δ) and coupling constants, J are reported in Hertz. For proton spectra the solvent peak was used as the reference peak.

Example 1: 2-(1-(2-(4-methoxy-3-(2-morpholinoethoxy)phenyl)-5-methylthiazol-4-yl)ethylthio)pyrimidine-4,6-diamine (6)

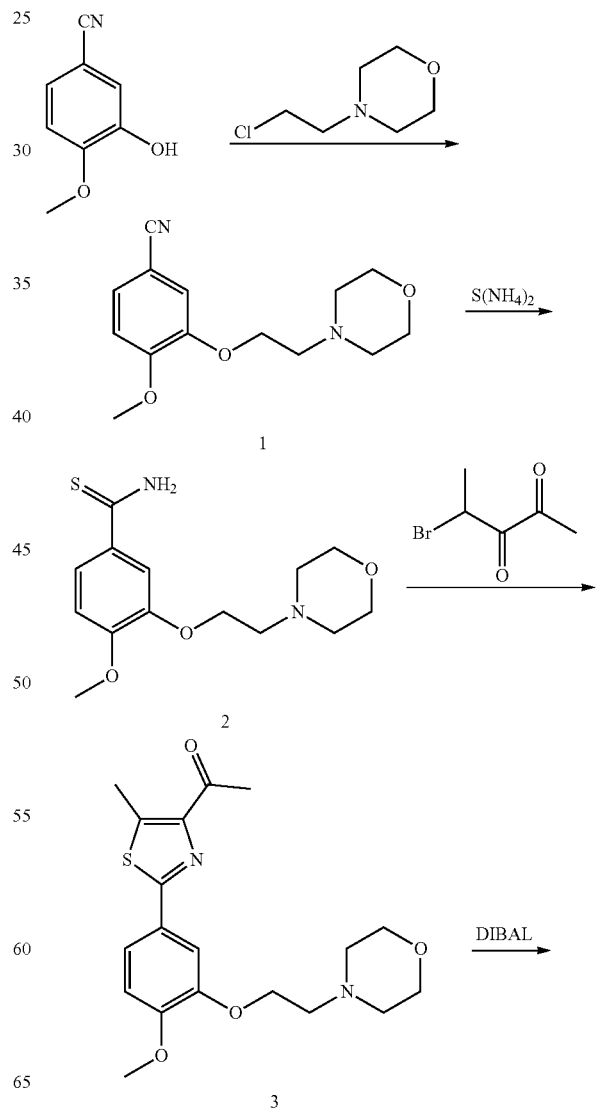

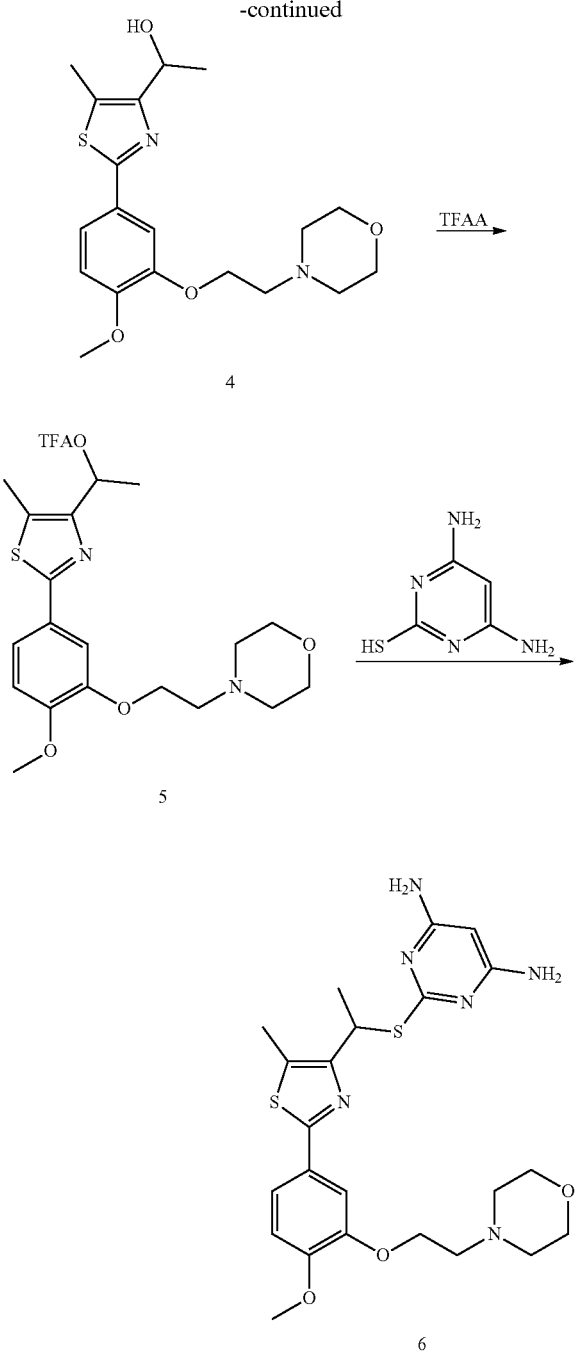

Step 2: Synthesis of 4-methoxy-3-(2-morpholinoethoxy)benzothioamide (2). Compound 1 (2.46 g, 9.4 mmol) was dissolved in pyridine (5 mL, 61.8 mmol) and $Et_3N$ (1.44 ml, 10.3 mmol) were added, followed by aq. ammonium sulfide (20%, 12 mL, 35.2 mmol). The reaction mixture is stirred and heated to 60° C. overnight. After cooling to rt, solvents were removed under reduced pressure and mixed with EtOAc (50 mL) and sat. aq. $NH_4Cl$ (200 mL). The mixture was extracted with EtOAc (2×20 mL). The combined organic solvents were removed under reduced pressure and the residue dried to give the desired product 2 as a yellow solid in a yield of 79%. HRMS calcd for $C_{14}H_{20}N_2O_3S$ 297.1267, found 297.1266.

Step 3: Synthesis of 1-(2-(4-methoxy-3-(2-morpholinoethoxy)phenyl)-5-methylthiazol-4-yl)ethan-1-one (3). To a solution of compound 2 (1.40 g, 4.7 mmol) in EtOH (30 mL) was added 4-bromopentane-2,3-dione (0.84 g, 4.7 mmol). The reaction mixture was heated to 80° C. for 3 hours. After cooling to rt, the solvents were removed under reduced pressure and the residue mixed with $CH_2Cl_2$ (20 mL) and water (100 mL). The mixture was extracted with $CH_2Cl_2$ (2×10 mL) and the combined organic solvents removed under reduced pressure. The product 3 was obtained as a brown solid without further purification in a yield of 76%. HRMS calcd for $C_{19}H_{24}N_2O_4S$ 377.1530, found 377.1526.

Step 4: Synthesis of 1-(2-(4-methoxy-3-(2-morpholinoethoxy)phenyl)-5-methylthiazol-4-yl)ethan-1-ol (4). A solution of 3 (1.35 g, 3.6 mmol) in $CH_2Cl_2$ (40 mL) was cooled to −78° C. and DIBAL-H (1M in $CH_2Cl_2$, 14.3 mL, 14.3 mmol) was slowly added. The reaction mixture was allowed to warm to rt and stirred for 30 min. The solution was cooled to 0° C. and add sat. aq. potassium sodium tartrate (10 mL) was added and the mixture was stirred for 1 hour. The solution was extracted with $CH_2Cl_2$ (3×10 mL) and the combined organic solvents were removed under reduced pressure. The crude residue was purified over silica gel using 5-10% MeOH in $CH_2Cl_2$. The pure product 4 was obtained in a yield of 40% as a yellow oil. HRMS calcd for $C_{19}H_{26}N_2O_4S$ 379.1686, found 379.1684.

Step 5: Synthesis of 1-(2-(4-methoxy-3-(2-morpholinoethoxy)phenyl)-5-methylthiazol-4-yl)ethyl 2,2,2-trifluoroacetate (5). A solution of compound 4 (47 mg, 0.12 mmol) in $CH_2Cl_2$ (5 mL) was cooled to 0° C. and trifluoroacetic anhydride (70 μL, 0.5 mmol) was added dropwise. The reaction mixture was allowed to warm to rt and stirred for 1 hour. The mixture was cooled to 0° C. and ice-cooled water (20 mL) was added. The mixture was extracted with $CH_2Cl_2$ (2×5 mL) and the combined organic layers were removed under reduced pressure to give the desired compound 5 in quantitative yields.

Step 1: Synthesis of 4-methoxy-3-(2-morpholinoethoxy)benzonitrile (1). A mixture of potassium carbonate (4.52 g, 32.7 mmol), 3-hydroxy-4-methoxybenzonitrile (2.44 g, 16.4 mmol) and 4-(2-chloroethyl)morpholine (2.45 g, 16.4 mmol) was heated in a solvent mixture of DMF (40 mL) and acetone (25 mL) to 100° C. for 8 hours. After cooling to rt, the reaction mixture was diluted with aq HCl (0.1M, 150 mL) and extracted with $CH_2Cl_2$ (3×15 mL). The combined organic layers were removed under reduced pressure and the crude residue purified over silica gel using $CH_2Cl_2$:MeOH (40:1) as the eluent. The desired product 1 was obtained in a yield of 85% as a yellow oil. HRMS calcd for $C_{14}H_{18}N_2O_3$ 263.1390, found 263.1386.

Step 6: Synthesis of 2-((1-(2-(4-methoxy-3-(2-morpholinoethoxy)phenyl)-5-methylthiazol-4-yl)ethyl)thio)pyrimidine-4,6-diamine (6). To a solution of 4,6-diaminopyrimidine-2-thiol (45 mg, 0.31 mmol) in DMF (1.5 mL) was added potassium carbonate (87 mg, 0.63 mmol), followed by 5 (75 mg, 0.16 mmol). The solution was stirred and heated to 80° C. overnight. After cooling to rt, the reaction mixture was diluted with water (20 mL) and extracted with $CH_2Cl_2$ (3×5 mL). The organic layers were combined and solvents removed under reduced pressure. The crude residue was purified over silica gel using 5-10% MeOH in $CH_2Cl_2$ to give the desired final compound 6 in a yield of 25%. HRMS calcd for $C_{23}H_{30}N_6O_3S_2$ 503.1894, found 503.1876.

Example 2: (R)-2-(1-(2-(4-methoxy-3-(2-morpholinoethoxy)phenyl)-5-methylthiazol-4-yl)ethylthio)pyrimidine-4,6-diamine (9R)

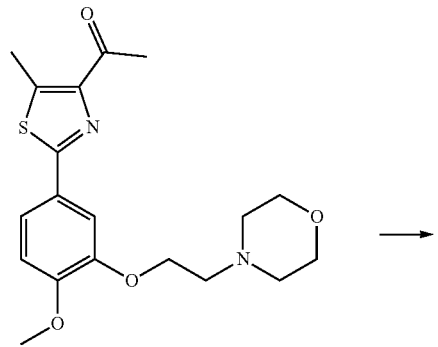

3

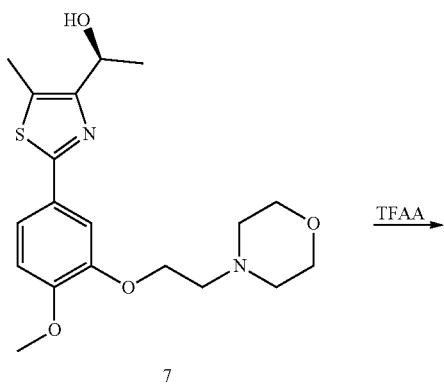

7

TFAA →

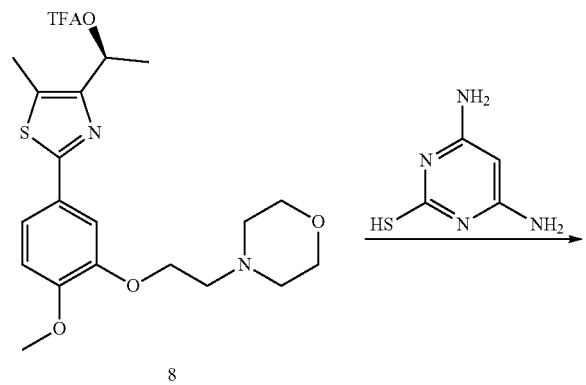

8

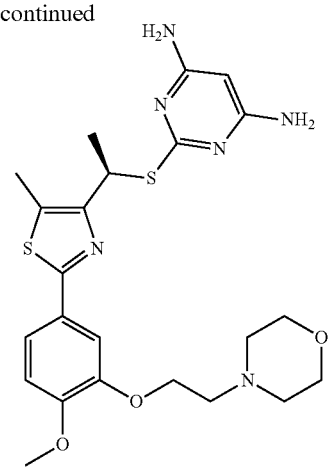

9R

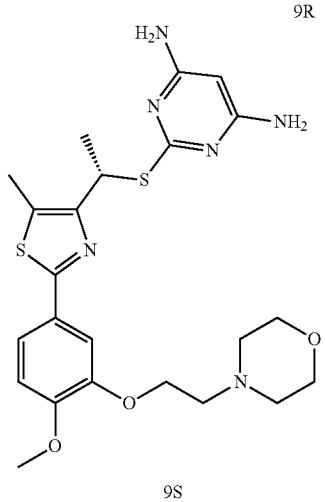

9S

Step 1: Synthesis of (S)-1-(2-(4-methoxy-3-(2-morpholinoethoxy)phenyl)-5-methylthiazol-4-yl)ethanol (7). To a stirred solution of (R)-(+)-2-Methyl-CBS-oxazaborolidine 1.0 M solution in toluene) in THF at −78° C. under Ar was added borane-tetrahydrofuran complex (1.0 M solution in THF) followed by a solution of 3 in THF. After finish adding the 3 solution with syringe pump for 6 h, the reaction mixture was stirred for another 20 min at −78° C. $H_2O$ and MeOH were added and the mixture was allowed to warm to room temperature. After concentration to remove residual solvent, the resulting residue was washed with brine and extracted with ethyl acetate. The organic layer was washed with water three times, dried over anhydrous $Na_2SO_4$ and concentrated in vacuo, and the crude residue was purified by flash column chromatography over silica gel to yield alcohol 7 as a white solid. HRMS calcd for $C_{19}H_{26}N_2O_4S$ 379.1686, found 379.1684.

Step 2: Synthesis of (S)-1-(2-(4-methoxy-3-(2-morpholinoethoxy)phenyl)-5-methylthiazol-4-yl)ethyl 2,2,2-trifluoroacetate (8). A solution of compound 7 (47 mg, 0.12 mmol) in $CH_2Cl_2$ (5 mL) was cooled to 0° C. and trifluoroacetic anhydride (70 μL, 0.5 mmol) was added dropwise. The reaction mixture was allowed to warm to rt and stirred for 1 hour. The mixture was cooled to 0° C. and ice-cooled water (20 mL) was added. The mixture was extracted with $CH_2Cl_2$ (2×5 mL) and the combined organic layers were removed under reduced pressure to give the desired compound 8 in quantitative yields.

Step 3: Synthesis of (R)-2-(1-(2-(4-methoxy-3-(2-morpholinoethoxy)phenyl)-5-methylthiazol-4-yl)ethylthio)pyrimidine-4,6-diamine (9R) and (S)-2-(1-(2-(4-methoxy-3-(2-morpholinoethoxy)phenyl)-5-methylthiazol-4-yl)ethylthio)pyrimidine-4,6-diamine (9S). To a solution of 4,6-diaminopyrimidine-2-thiol (45 mg, 0.31 mmol) in DMF (1.5 mL) was added potassium carbonate (87 mg, 0.63 mmol), followed by 8 (75 mg, 0.16 mmol). The solution was stirred and heated to 80° C. overnight. After cooling to rt, the reaction mixture was diluted with water (20 mL) and extracted with $CH_2Cl_2$ (3×5 mL). The organic layers were combined and solvents removed under reduced pressure. The crude residue was purified over silica gel using 5-10% MeOH in $CH_2Cl_2$ to afford the couple of enantiomers 9R and 9S as a white solid. Recrystallization of the enantiomers with MeOH/acetone solvent system gave 9R with 93% ee. HRMS calcd for $C_{23}H_{30}N_6O_3S_2$ 503.1894, found 503.1876.

Example 3: The Following Compounds were Prepared According to the Procedures Described in Example 1 (Table 1)

TABLE 1

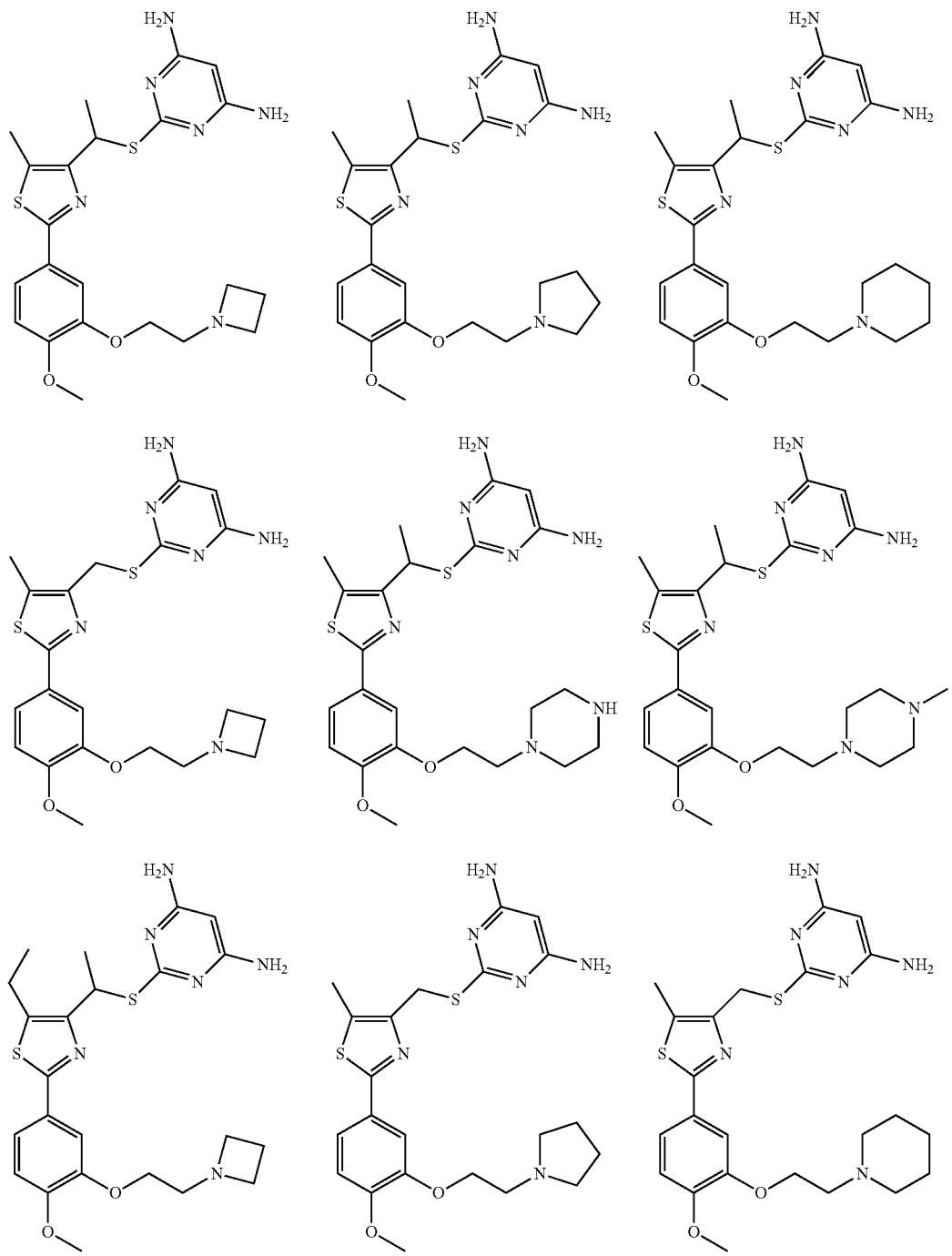

TABLE 1-continued
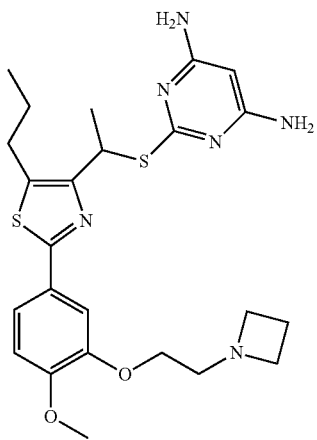 [SMILES: CCCc1sc(-c2ccc(OC)c(OCCN3CCC3)c2)nc1C(C)Sc1nc(N)cc(N)n1] 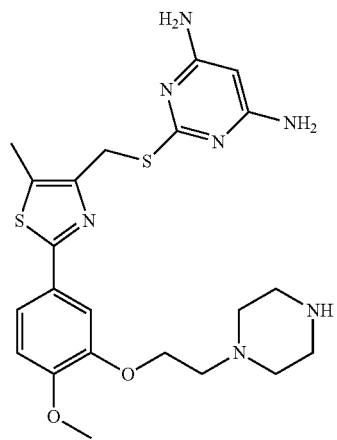 [SMILES: COc1ccc(-c2nc(CSc3nc(N)cc(N)n3)c(C)s2)cc1OCCN1CCNCC1] 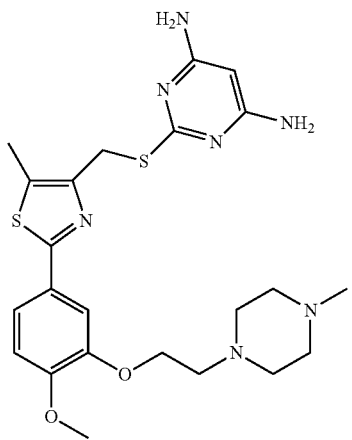
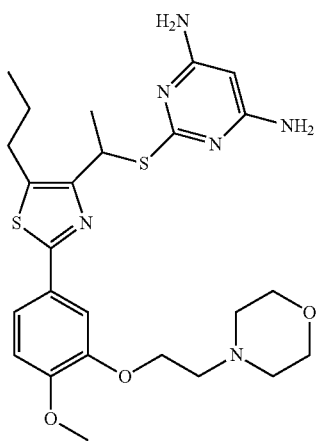 [SMILES: CCCc1sc(-c2ccc(OC)c(OCCN3CCOCC3)c2)nc1C(C)Sc1nc(N)cc(N)n1] 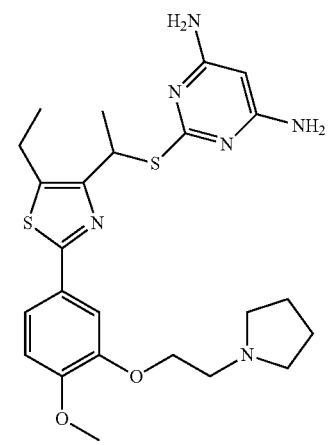 [SMILES: CCc1sc(-c2ccc(OC)c(OCCN3CCCC3)c2)nc1C(C)Sc1nc(N)cc(N)n1] 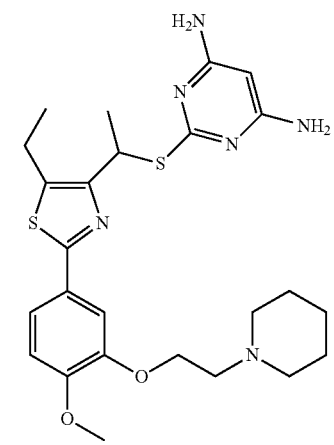 [SMILES: CCc1sc(-c2ccc(OC)c(OCCN3CCCCC3)c2)nc1C(C)Sc1nc(N)cc(N)n1]
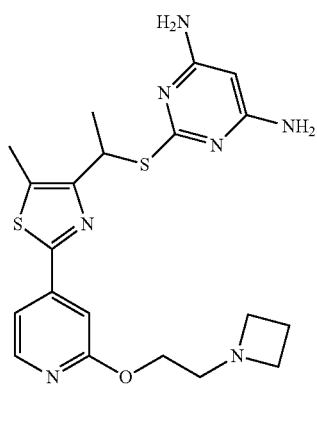 [SMILES: Cc1sc(-c2ccnc(OCCN3CCC3)c2)nc1C(C)Sc1nc(N)cc(N)n1] 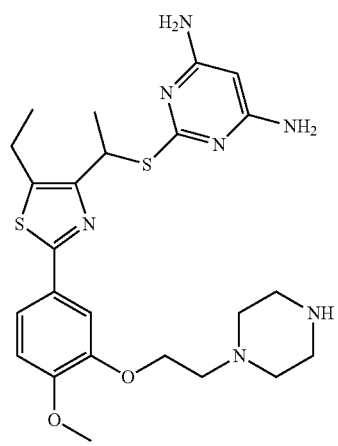 [SMILES: CCc1sc(-c2ccc(OC)c(OCCN3CCNCC3)c2)nc1C(C)Sc1nc(N)cc(N)n1] 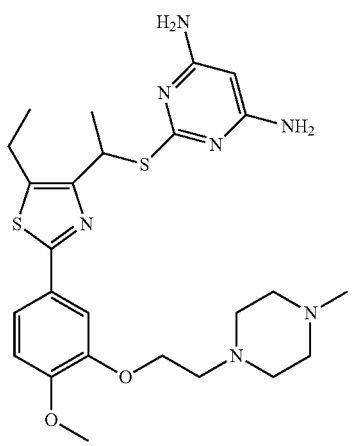 [SMILES: CCc1sc(-c2ccc(OC)c(OCCN3CCN(C)CC3)c2)nc1C(C)Sc1nc(N)cc(N)n1]

TABLE 1-continued
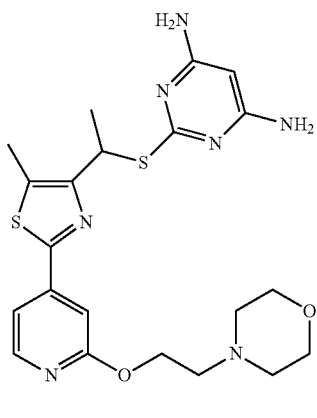 [SMILES: Cc1sc(-c2ccnc(OCCN3CCOCC3)c2)nc1C(C)Sc1nc(N)cc(N)n1] 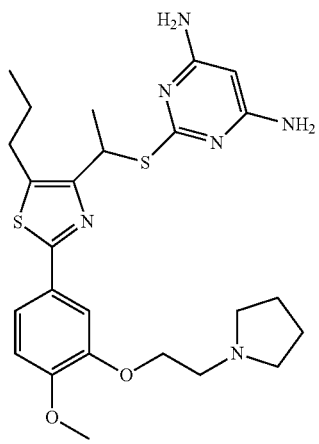 [SMILES: CCCc1sc(-c2ccc(OC)c(OCCN3CCCC3)c2)nc1C(C)Sc1nc(N)cc(N)n1] 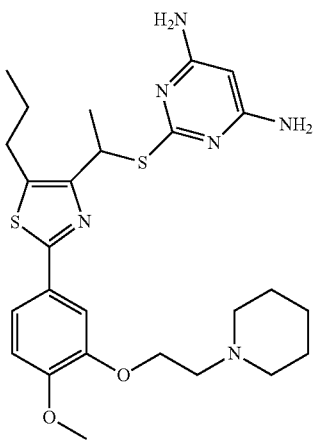 [SMILES: CCCc1sc(-c2ccc(OC)c(OCCN3CCCCC3)c2)nc1C(C)Sc1nc(N)cc(N)n1]
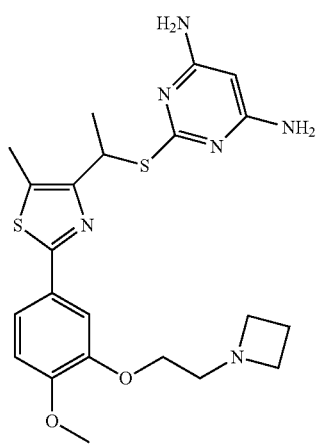 [SMILES: COc1ccc(-c2nc(C(C)Sc3nc(N)cc(N)n3)c(C)s2)cc1OCCN1CCC1] 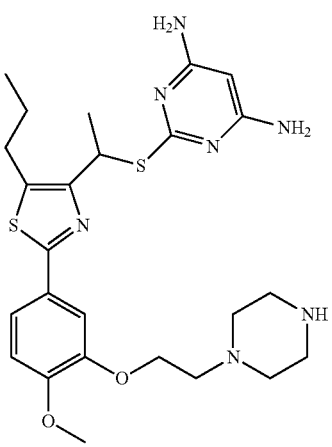 [SMILES: CCCc1sc(-c2ccc(OC)c(OCCN3CCNCC3)c2)nc1C(C)Sc1nc(N)cc(N)n1] 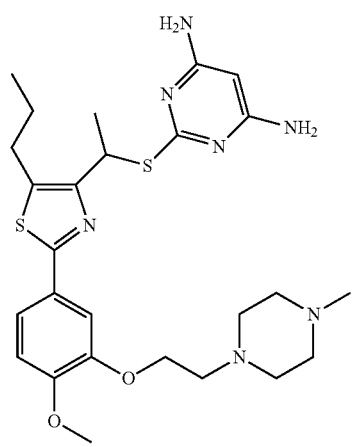 [SMILES: CCCc1sc(-c2ccc(OC)c(OCCN3CCN(C)CC3)c2)nc1C(C)Sc1nc(N)cc(N)n1]
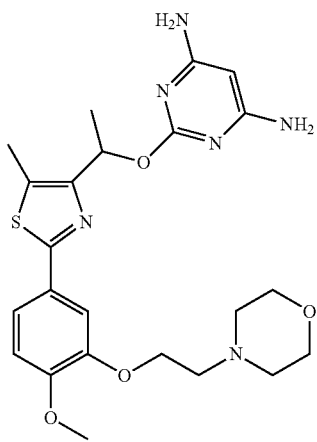 [SMILES: COc1ccc(-c2nc(C(C)Oc3nc(N)cc(N)n3)c(C)s2)cc1OCCN1CCOCC1] 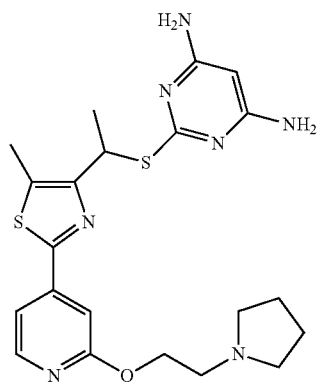 [SMILES: Cc1sc(-c2ccnc(OCCN3CCCC3)c2)nc1C(C)Sc1nc(N)cc(N)n1] 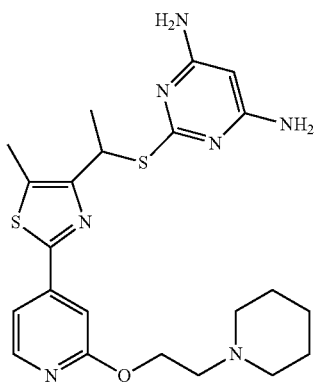 [SMILES: Cc1sc(-c2ccnc(OCCN3CCCCC3)c2)nc1C(C)Sc1nc(N)cc(N)n1]

TABLE 1-continued
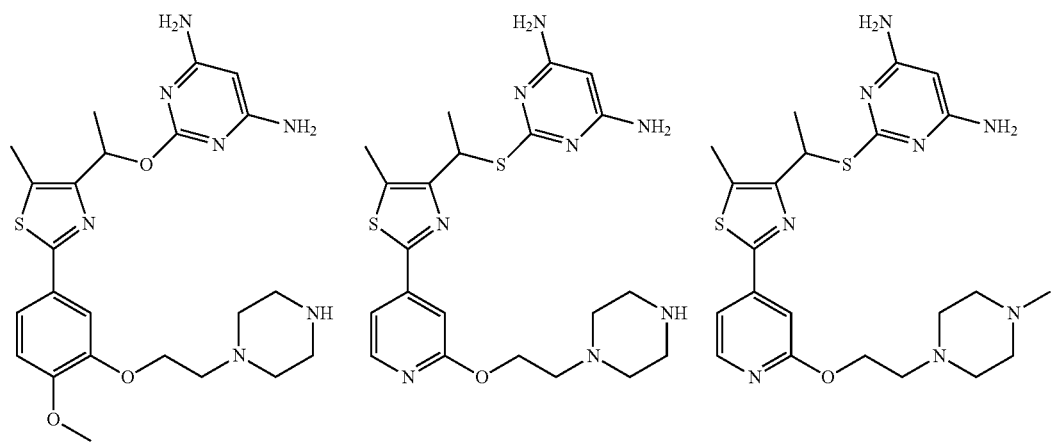
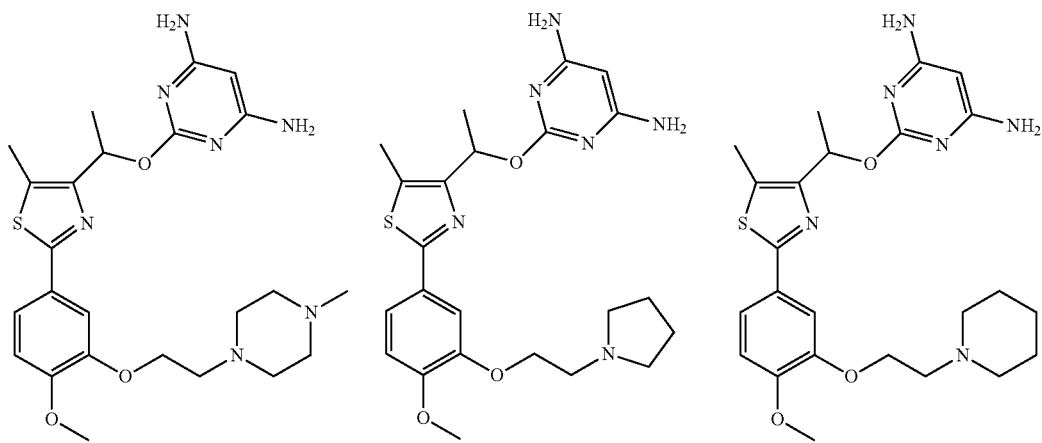
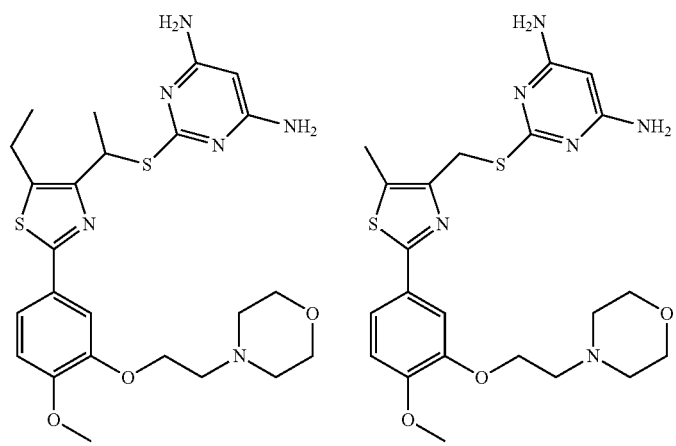

Example 4: The Following Compounds were Prepared According to the Procedures Described in Example 2 (Table 2)
TABLE 2
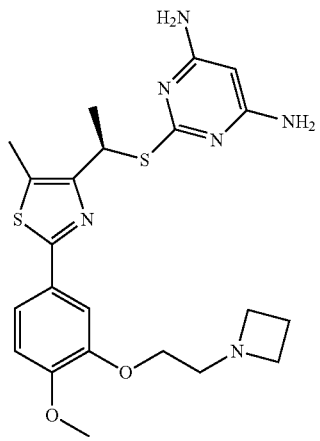 [SMILES: COc1ccc(-c2nc([C@@H](C)Sc3nc(N)cc(N)n3)c(C)s2)cc1OCCN1CCC1] 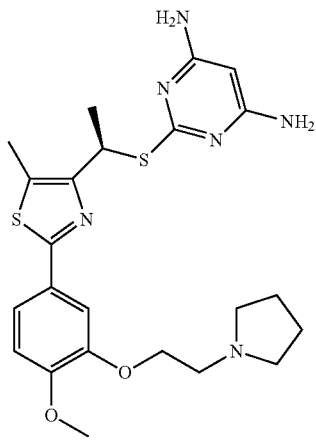 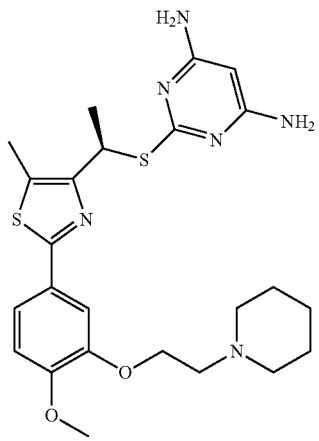
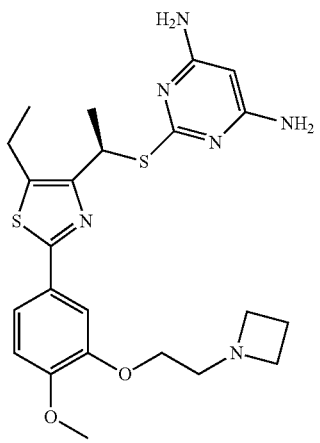 [SMILES: CCc1sc(-c2ccc(OC)c(OCCN3CCC3)c2)nc1[C@@H](C)Sc1nc(N)cc(N)n1] 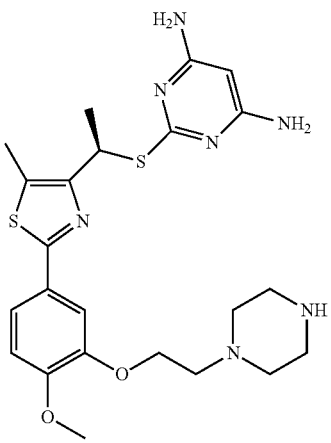 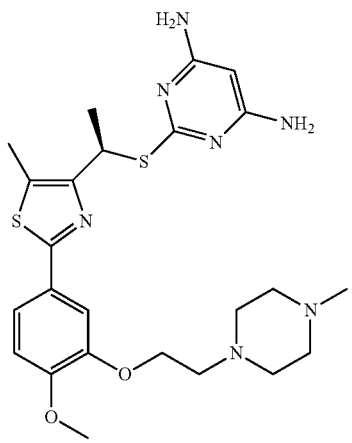
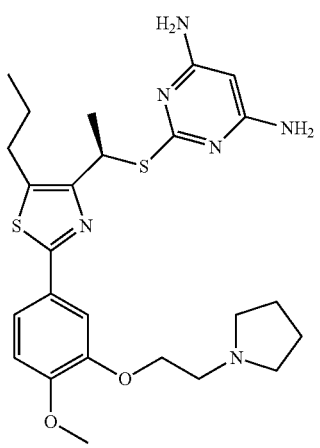 [SMILES: CCCc1sc(-c2ccc(OC)c(OCCN3CCCC3)c2)nc1[C@@H](C)Sc1nc(N)cc(N)n1] 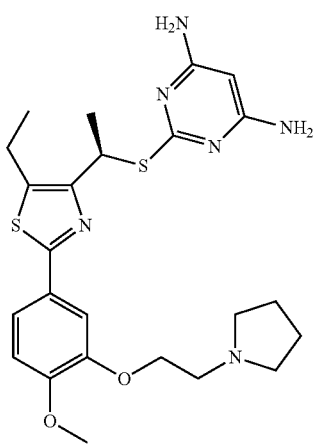 [SMILES: CCc1sc(-c2ccc(OC)c(OCCN3CCCC3)c2)nc1[C@@H](C)Sc1nc(N)cc(N)n1] 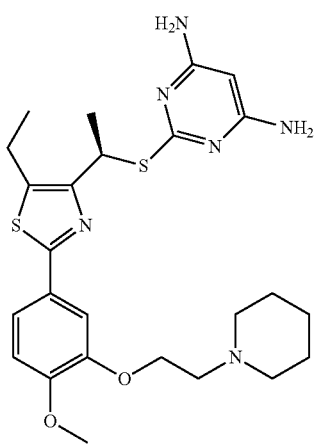 [SMILES: CCc1sc(-c2ccc(OC)c(OCCN3CCCCC3)c2)nc1[C@@H](C)Sc1nc(N)cc(N)n1]

TABLE 2-continued
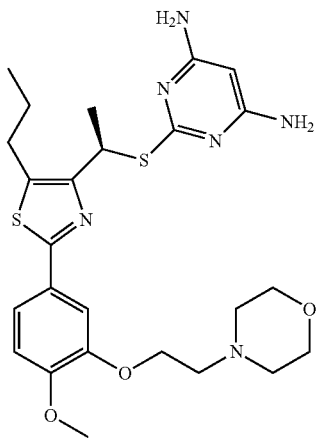 [SMILES: CCCc1sc(-c2ccc(OC)c(OCCN3CCOCC3)c2)nc1[C@@H](C)Sc1nc(N)cc(N)n1] 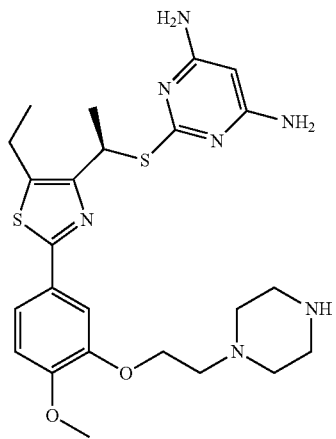 [SMILES: CCc1sc(-c2ccc(OC)c(OCCN3CCNCC3)c2)nc1[C@@H](C)Sc1nc(N)cc(N)n1] 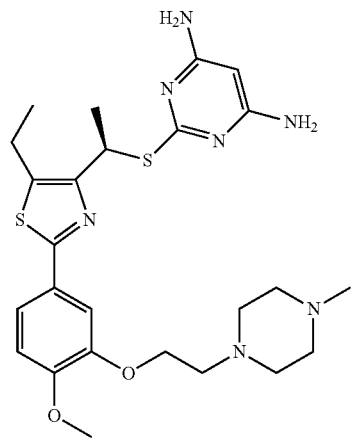 [SMILES: CCc1sc(-c2ccc(OC)c(OCCN3CCN(C)CC3)c2)nc1[C@@H](C)Sc1nc(N)cc(N)n1]
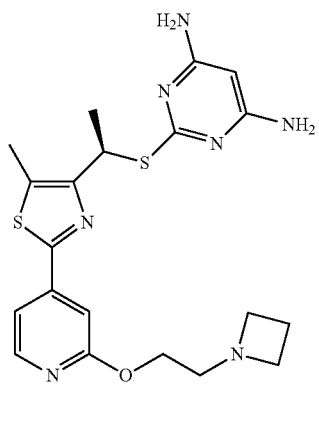 [SMILES: Cc1sc(-c2ccnc(OCCN3CCC3)c2)nc1[C@@H](C)Sc1nc(N)cc(N)n1] 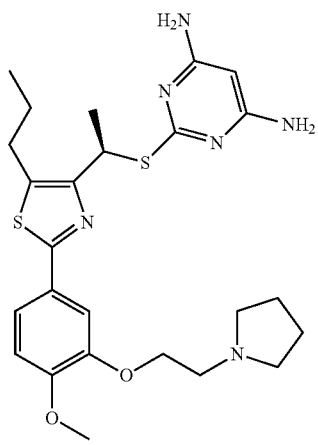 [SMILES: CCCc1sc(-c2ccc(OC)c(OCCN3CCCC3)c2)nc1[C@@H](C)Sc1nc(N)cc(N)n1] 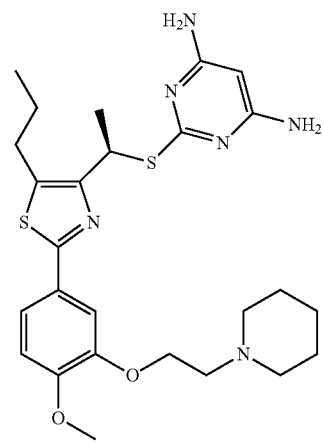 [SMILES: CCCc1sc(-c2ccc(OC)c(OCCN3CCCCC3)c2)nc1[C@@H](C)Sc1nc(N)cc(N)n1]
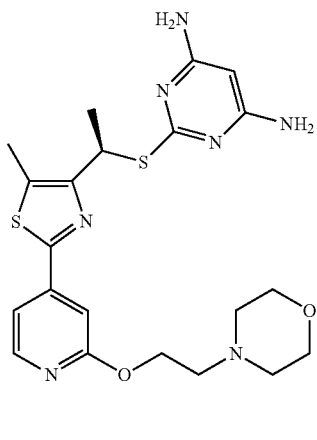 [SMILES: Cc1sc(-c2ccnc(OCCN3CCOCC3)c2)nc1[C@@H](C)Sc1nc(N)cc(N)n1] 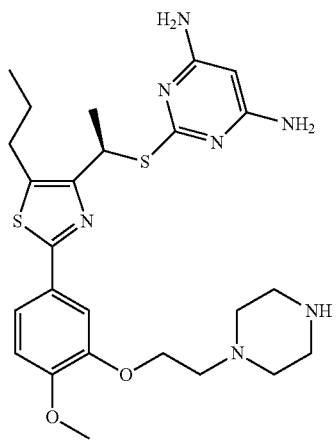 [SMILES: CCCc1sc(-c2ccc(OC)c(OCCN3CCNCC3)c2)nc1[C@@H](C)Sc1nc(N)cc(N)n1] 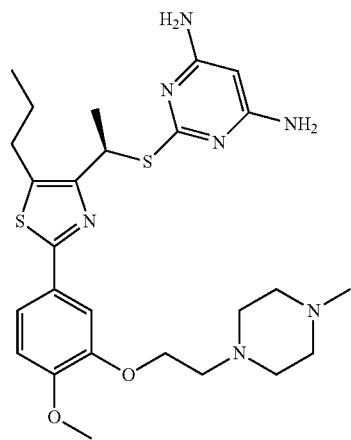 [SMILES: CCCc1sc(-c2ccc(OC)c(OCCN3CCN(C)CC3)c2)nc1[C@@H](C)Sc1nc(N)cc(N)n1]

TABLE 2-continued
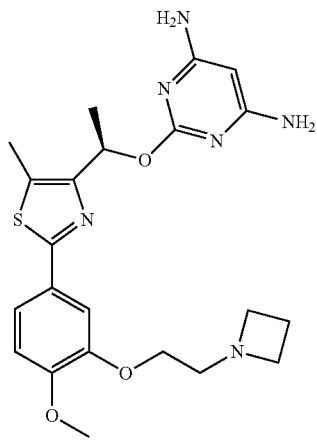 [SMILES: COc1ccc(-c2nc([C@@H](C)Oc3nc(N)cc(N)n3)c(C)s2)cc1OCCN1CCC1] 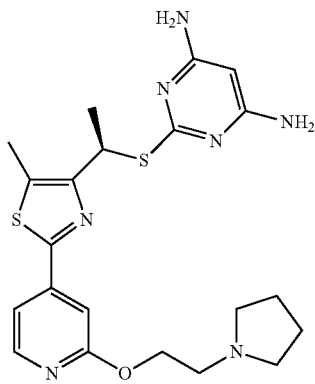 [SMILES: Cc1sc(-c2ccnc(OCCN3CCCC3)c2)nc1[C@@H](C)Sc1nc(N)cc(N)n1] 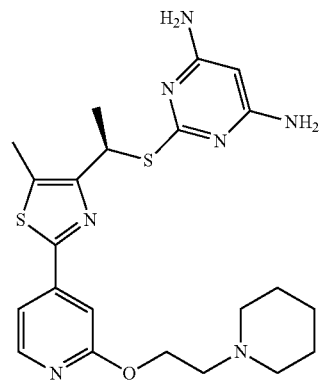 [SMILES: Cc1sc(-c2ccnc(OCCN3CCCCC3)c2)nc1[C@@H](C)Sc1nc(N)cc(N)n1]
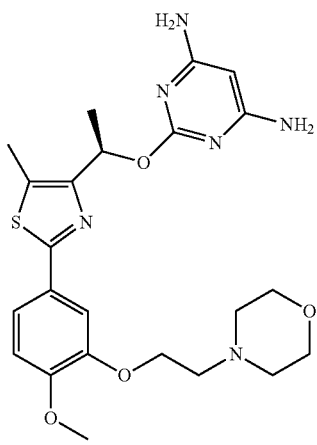 [SMILES: COc1ccc(-c2nc([C@@H](C)Oc3nc(N)cc(N)n3)c(C)s2)cc1OCCN1CCOCC1] 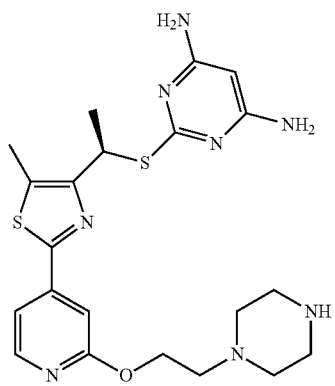 [SMILES: Cc1sc(-c2ccnc(OCCN3CCNCC3)c2)nc1[C@@H](C)Sc1nc(N)cc(N)n1] 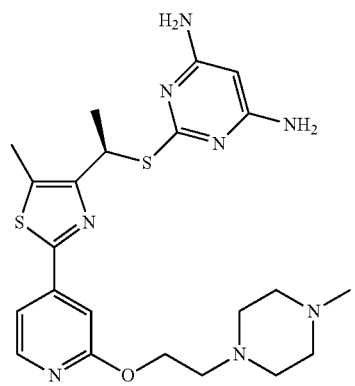
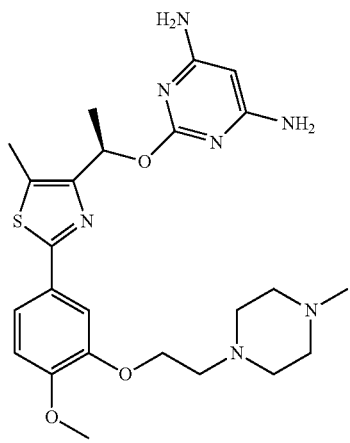 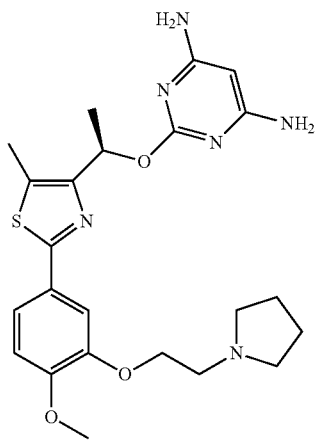 [SMILES: COc1ccc(-c2nc([C@@H](C)Oc3nc(N)cc(N)n3)c(C)s2)cc1OCCN1CCCC1] 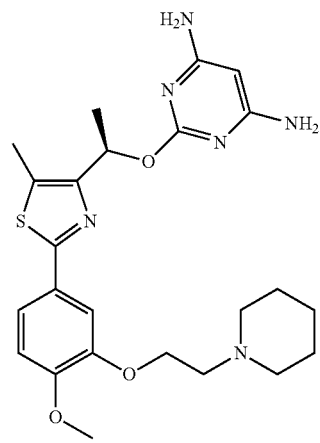 [SMILES: COc1ccc(-c2nc([C@@H](C)Oc3nc(N)cc(N)n3)c(C)s2)cc1OCCN1CCCCC1]

TABLE 2-continued
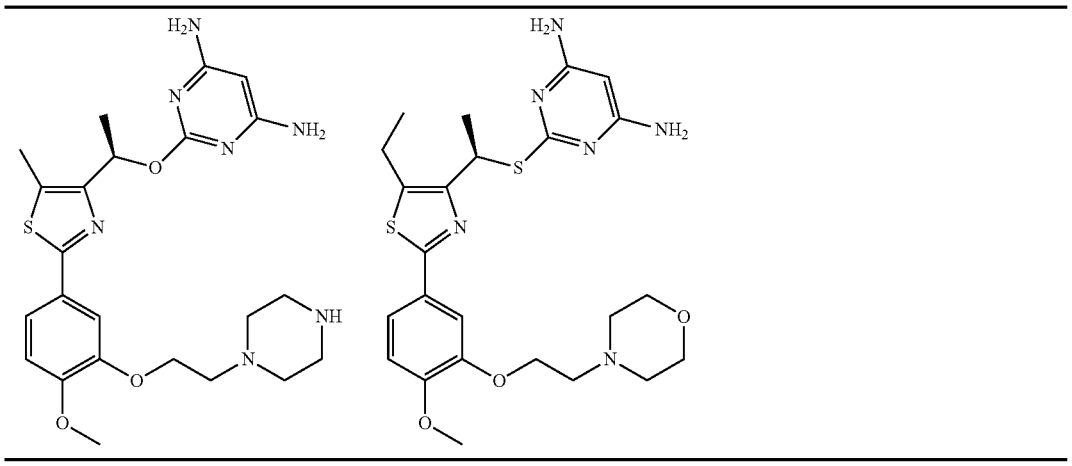
Example 5: The Following Compounds were Prepared According to the Procedures Described in Example 2 (Table 3)
TABLE 3
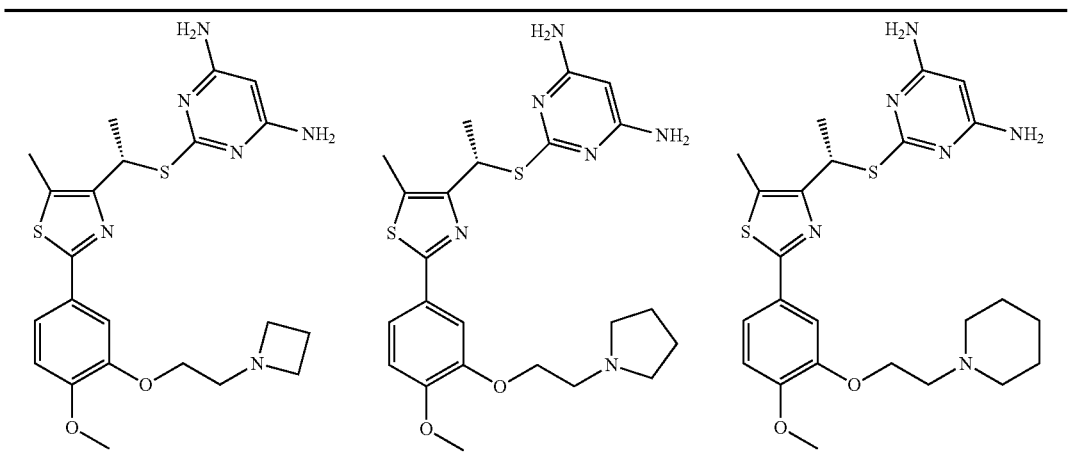
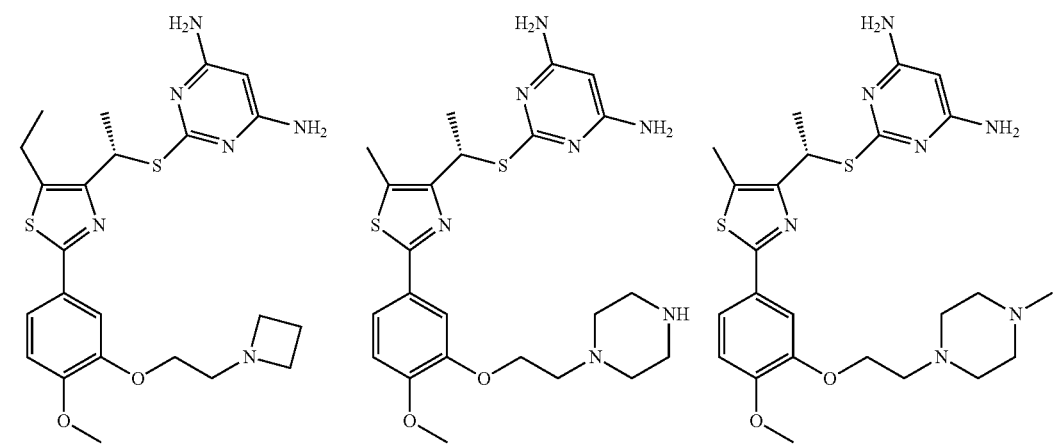

TABLE 3-continued
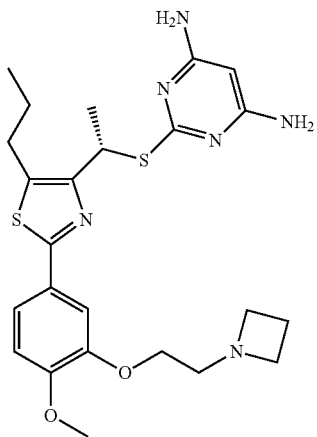 [SMILES: CCCc1sc(-c2ccc(OC)c(OCCN3CCC3)c2)nc1[C@H](C)Sc1nc(N)cc(N)n1] 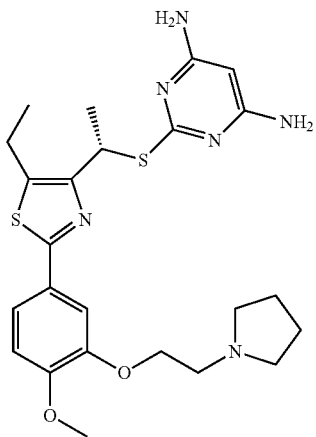 [SMILES: CCc1sc(-c2ccc(OC)c(OCCN3CCCC3)c2)nc1[C@H](C)Sc1nc(N)cc(N)n1] 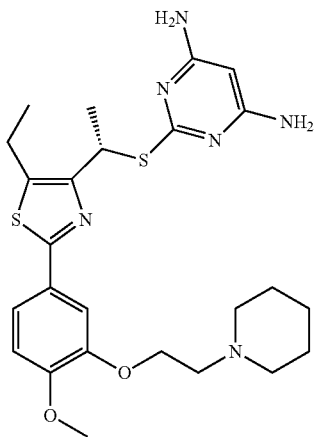 [SMILES: CCc1sc(-c2ccc(OC)c(OCCN3CCCCC3)c2)nc1[C@H](C)Sc1nc(N)cc(N)n1]
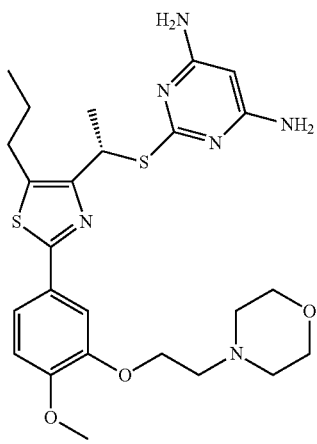 [SMILES: CCCc1sc(-c2ccc(OC)c(OCCN3CCOCC3)c2)nc1[C@H](C)Sc1nc(N)cc(N)n1] 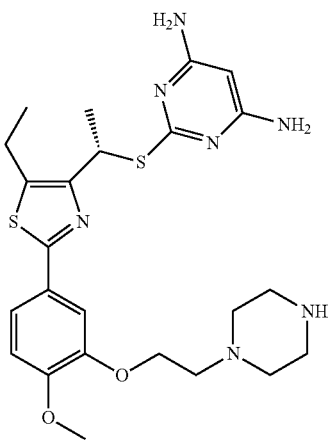 [SMILES: CCc1sc(-c2ccc(OC)c(OCCN3CCNCC3)c2)nc1[C@H](C)Sc1nc(N)cc(N)n1] 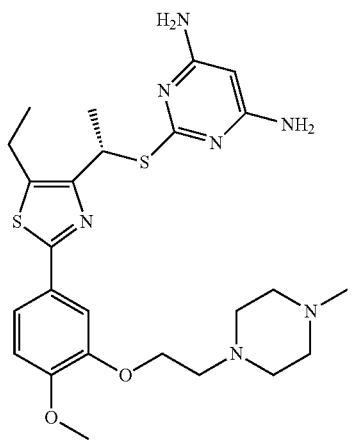 [SMILES: CCc1sc(-c2ccc(OC)c(OCCN3CCN(C)CC3)c2)nc1[C@H](C)Sc1nc(N)cc(N)n1]
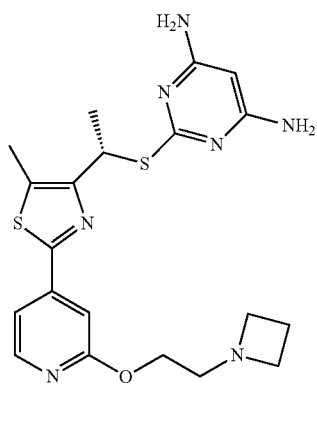 [SMILES: Cc1sc(-c2ccnc(OCCN3CCC3)c2)nc1[C@H](C)Sc1nc(N)cc(N)n1] 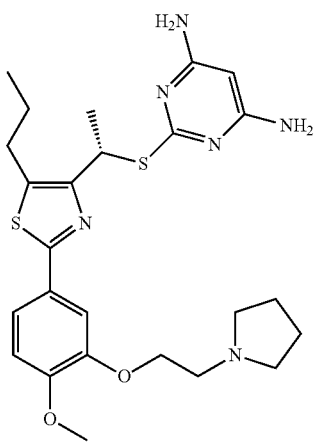 [SMILES: CCCc1sc(-c2ccc(OC)c(OCCN3CCCC3)c2)nc1[C@H](C)Sc1nc(N)cc(N)n1] 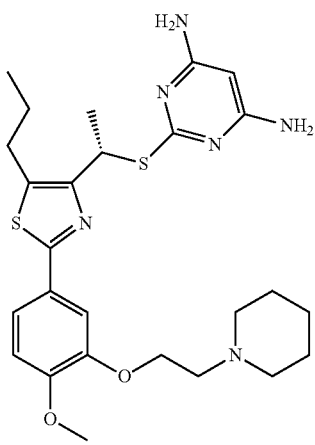 [SMILES: CCCc1sc(-c2ccc(OC)c(OCCN3CCCCC3)c2)nc1[C@H](C)Sc1nc(N)cc(N)n1]

TABLE 3-continued
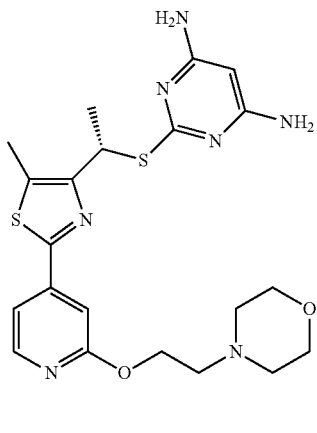 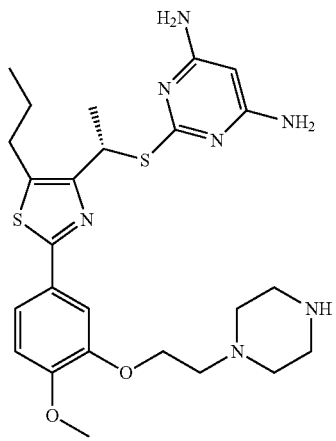 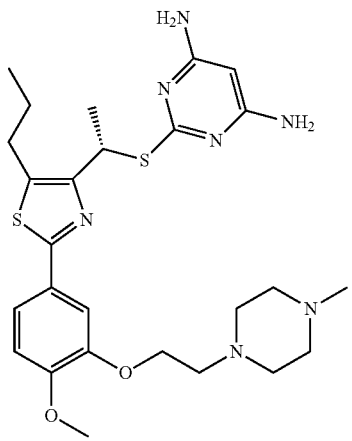 [SMILES: CCCc1sc(-c2ccc(OC)c(OCCN3CCN(C)CC3)c2)nc1[C@H](C)Sc1nc(N)cc(N)n1]
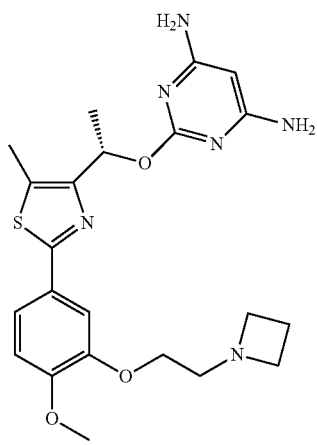 [SMILES: COc1ccc(-c2nc([C@H](C)Oc3nc(N)cc(N)n3)c(C)s2)cc1OCCN1CCC1] 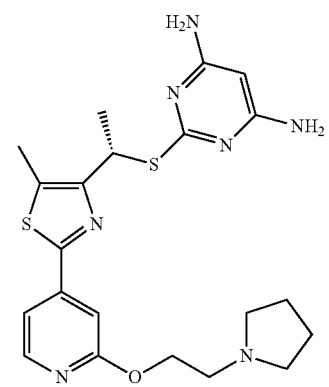 [SMILES: Cc1sc(-c2ccnc(OCCN3CCCC3)c2)nc1[C@H](C)Sc1nc(N)cc(N)n1] 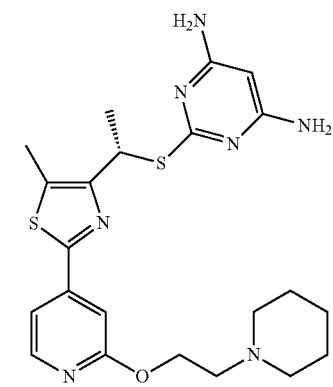
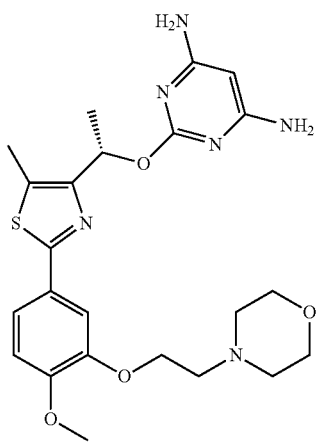 [SMILES: COc1ccc(-c2nc([C@H](C)Oc3nc(N)cc(N)n3)c(C)s2)cc1OCCN1CCOCC1] 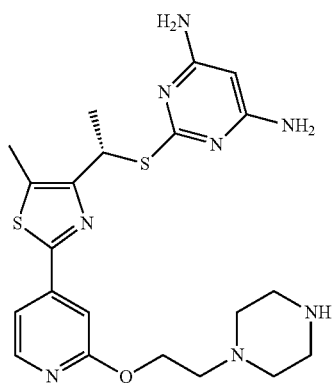 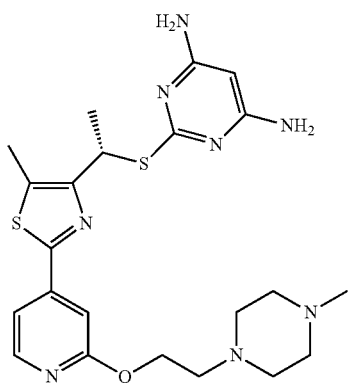

TABLE 3-continued

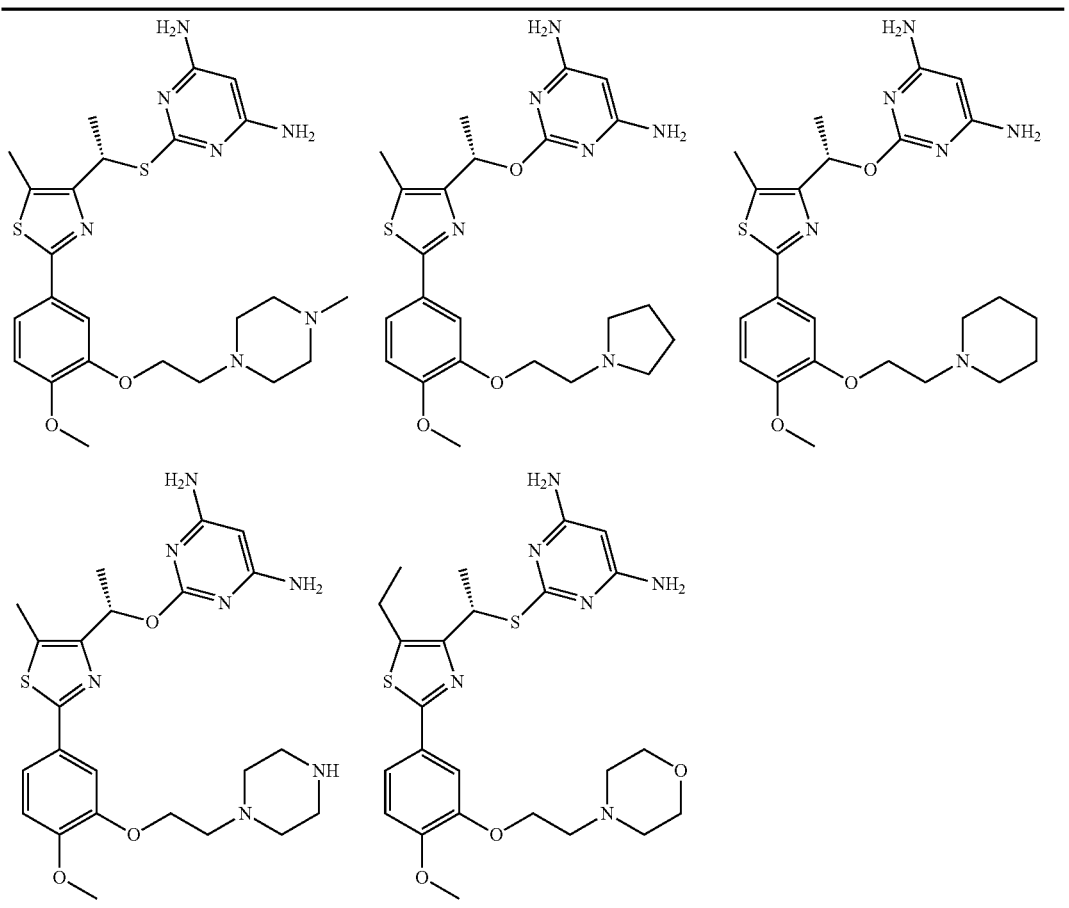

Example 6: Determination of Activity of dCK Inhibitors in Inhibition of [³H]-dCyd Uptake by CEM Cells Materials and Methods:

50,000 CEM cells/well were added to Millipore Multi-Screen GV 96 well plates. Cells were resuspended at 1×10^16 cells/mL and incubated for 30 minutes at 37° C. The drug dilution plate was prepared by starting with an initial drug concentration of 10 mM in DMSO, and proceeding to make 1:5 dilutions for drug. 10 mL of drug was added to 40 mL DMSO and mixed by pipetting 10 times before removing 10 uL for next well (1:5 serial dilutions). The media and tritiated deoxycytidine was mixed together. 245 mL of media/probe mixture was added to each well of an Optiplate. 5 mL from drug plate was added to each well in the Optiplate to obtain drug/media/probe mixture and mixed. 50 mL of drug/media/probe mixture from Optiplate was added to the cell plate and incubate at 37° C. for 1 hour. The cell plate was placed on vacuum to aspirate, and then washed with ice cold PBS: 200 mL 1×PBS 4 times. The backing of the plate was peeled off, and the plate was placed in dryer for at least 30 minutes or until dry at 37° C. 100 mL Scintillation fluid per well was added, and the plate was sealed with clear plate seal. The plate was read on the Microbeta instrument.

Figure 2:
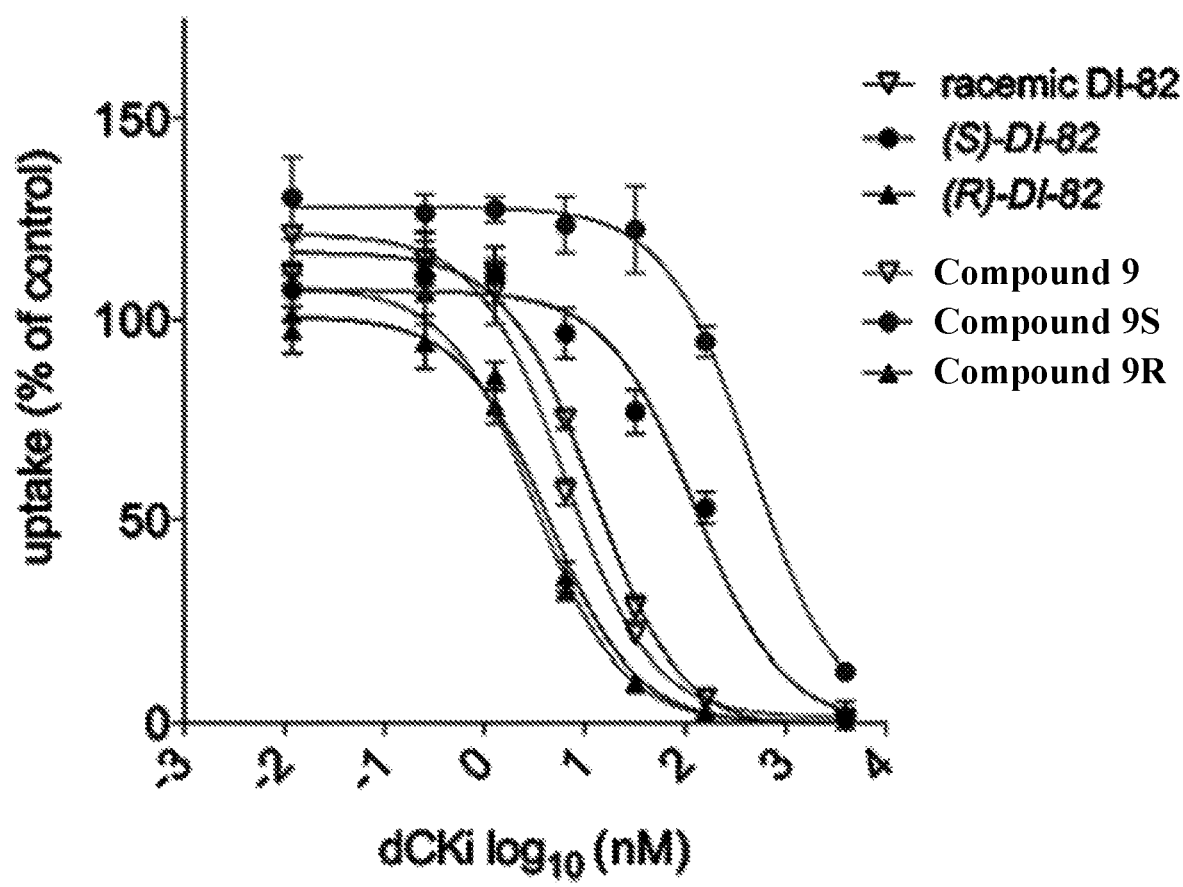
FIG. 2 shows the inhibition of the uptake by CEM leukemia cells of [$^3$H]-labeled deoxycytidine of DI-82, (S)-DI-82, (R)-DI-82, Compound 9, Compound 9S, and Compound 9R.

Inhibition of [³H]-deoxycytidine (dCyd) uptake by CEM cells was measured for Compounds DI-82, (S)-DI-82, (R)-DI-82, Compound 9, Compound 9S and Compound 9R (see FIG. 2 and Table 4).

TABLE 4

| Compound | dCKi-IC-50 (nM) |
|---|---|
| DI-82 | 11.9 |
| (S)-DI-82 | 123.6 |
| (R)-DI-82 | 4.33 |
| Compound 9 | 6.22 |
| Compound 9S | 468.4 |
| Compound 9R | 3.15 |

I.

Figure 3:
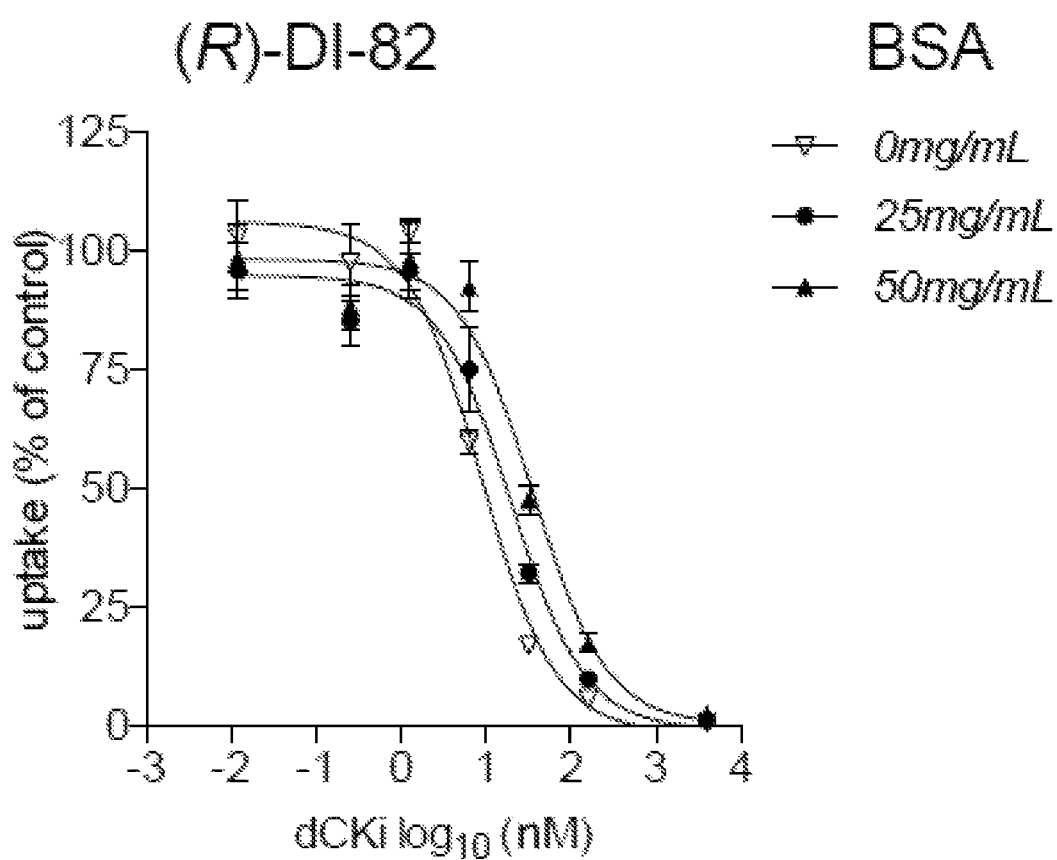
FIG. 3 shows the inhibition of the uptake by CEM leukemia cells of [$^3$H]-labeled deoxycytidine of (R)-DI-82 in the presence of varying concentration of BSA.
Figure 4:
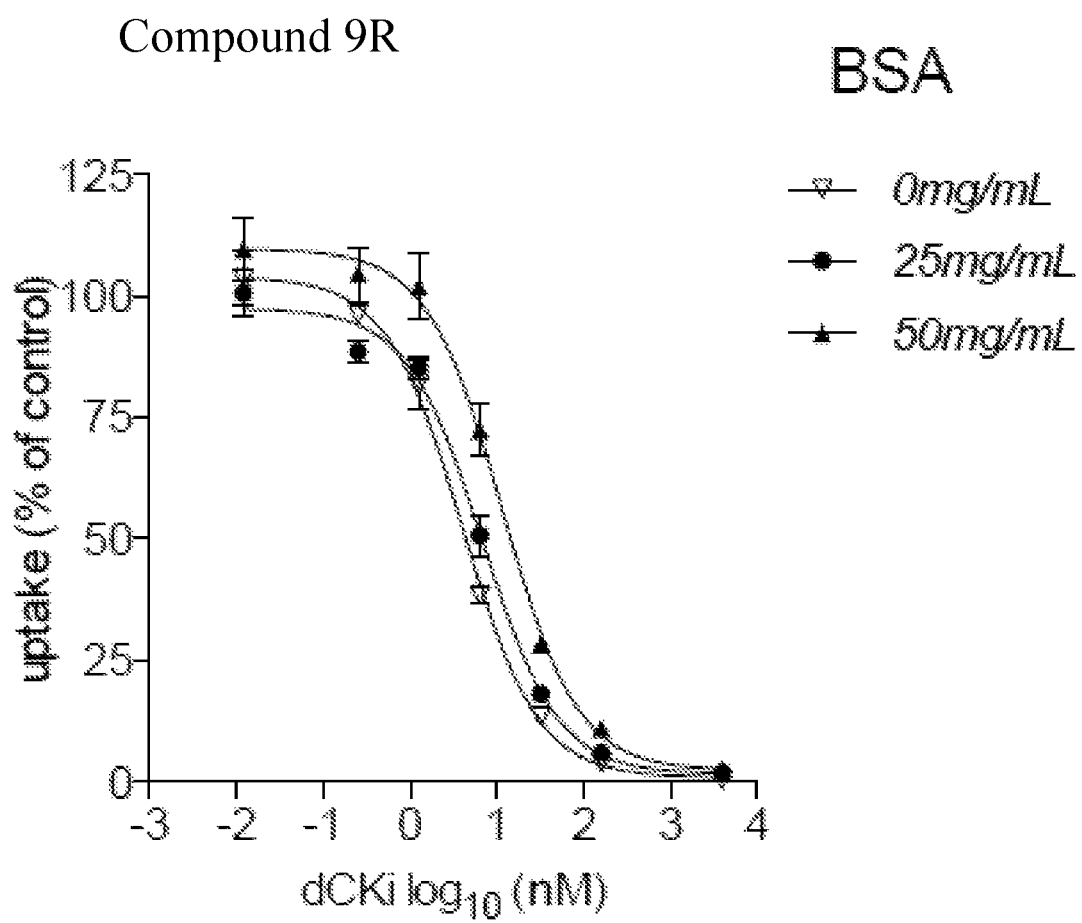
FIG. 4 shows the inhibition of the uptake by CEM leukemia cells of [$^3$H]-labeled deoxycytidine of Compound 9R in the presence of varying concentration of BSA.

The effect of BSA on the inhibition of [³H]dC uptake in CEM cells by (R)-DI-82 and Compound 9R was also measured (see FIG. 3 and FIG. 4 and table 5).

TABLE 5

| | dCKi-IC-50 (nM) | | |
|---|---|---|---|
| Compound | 0 mg/mL BSA | 25 mg/mL BSA | 50 mg/mL BSA |
| (R)-DI-82 | 8.87 | 19.93 | 35.78 |
| Compound 9R | 4.03 | 6.87 | 11.60 |

Example 7: Test for Inhibition of dCK Activity In Vivo Using PET Imaging

Mice were treated with DI-82, (R)-DI-82 and Compound 9R followed by injection of [¹⁸F]L-FAC 4 h after treatment and scanned at indicated time points by [¹⁸F]L-FAC PET/

CT to non-invasively determine dCK activity in vivo, throughout the body. [$^{18}$F]L-FAC PET/CT scans were performed as described in Shu, C. J. et al., "Novel PET probes specific for deoxycytidine kinase" J. Nucl. Med. 51(7): 1092-8 (2010).

Figure 5A:
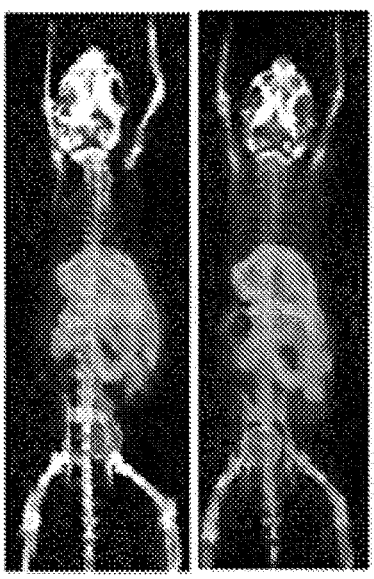
FIG. 5A shows the IP vehicle (PEG-Tris) [$^{18}$F]L-FAC microPET/CT scans.
Figure 5A:
Figure 5A:
Figure 5B:
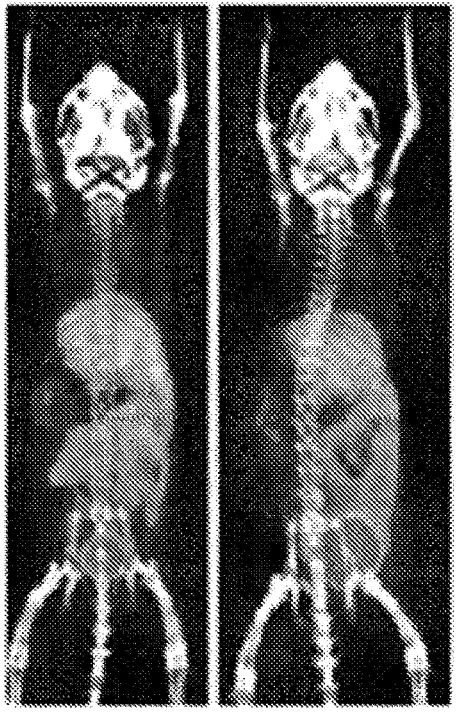
FIG. 5B shows the oral vehicle (P9 and P9') [$^{18}$F]L-FAC microPET/CT scans.
Figure 5B:
Figure 5B:
Figure 6A:
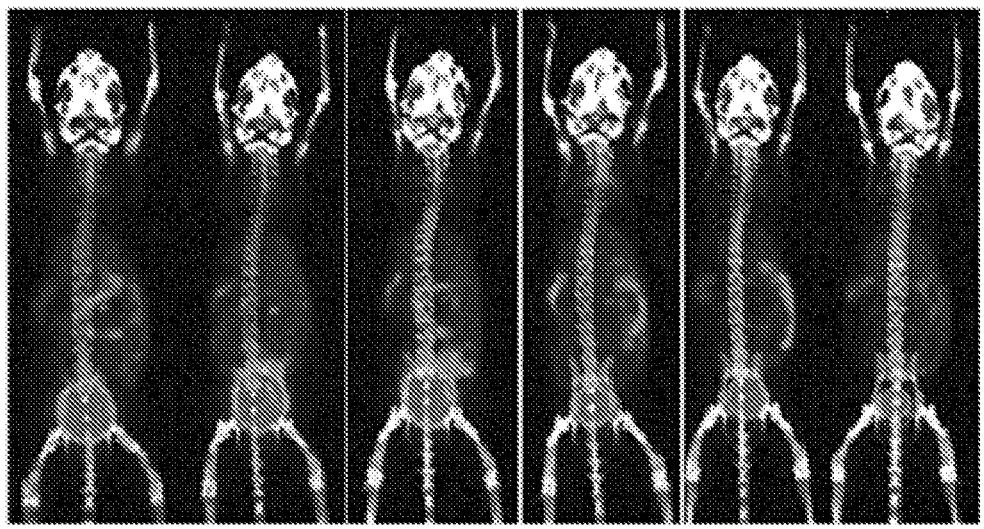
FIG. 6A shows the (R)-DI-82 [$^{18}$F]L-FAC microPET/CT scans (IP injection).
Figure 6B:
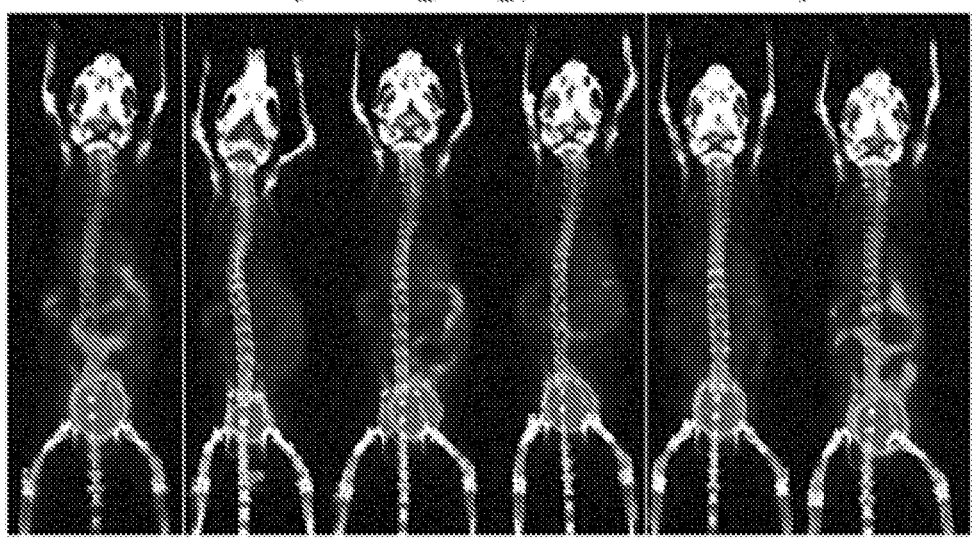
FIG. 6B shows the DI-82 [$^{18}$F]L-FAC microPET/CT scans (IP injection).
Figure 7:
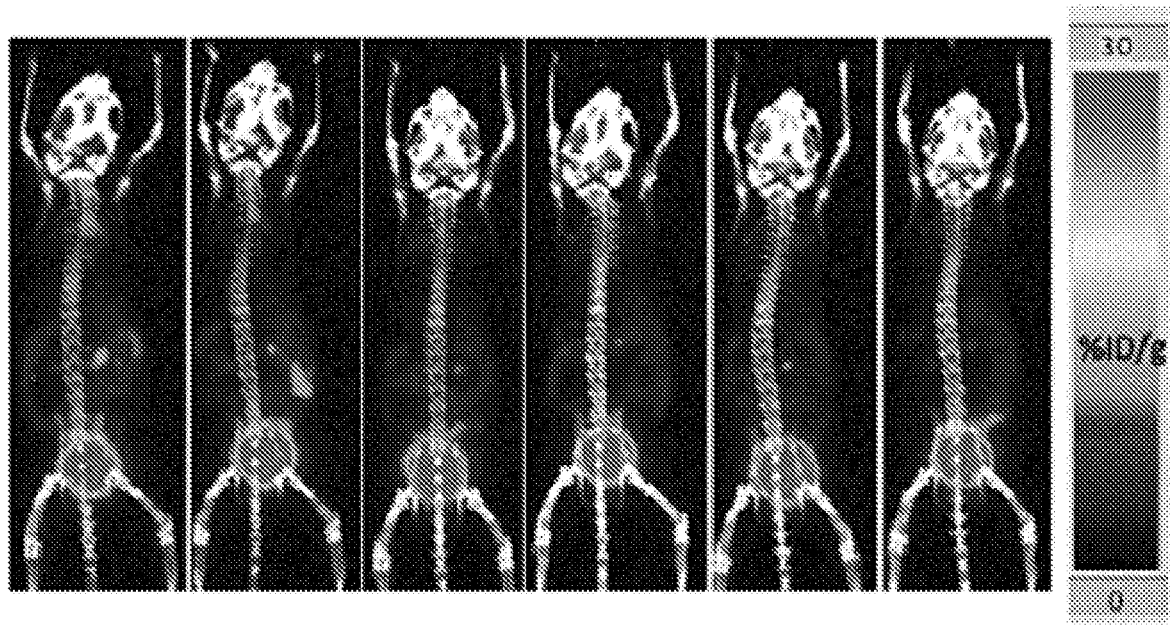
FIG. 7 shows the Compound 9R [$^{18}$F]L-FAC microPET/CT scans (IP injection).
Figure 8:
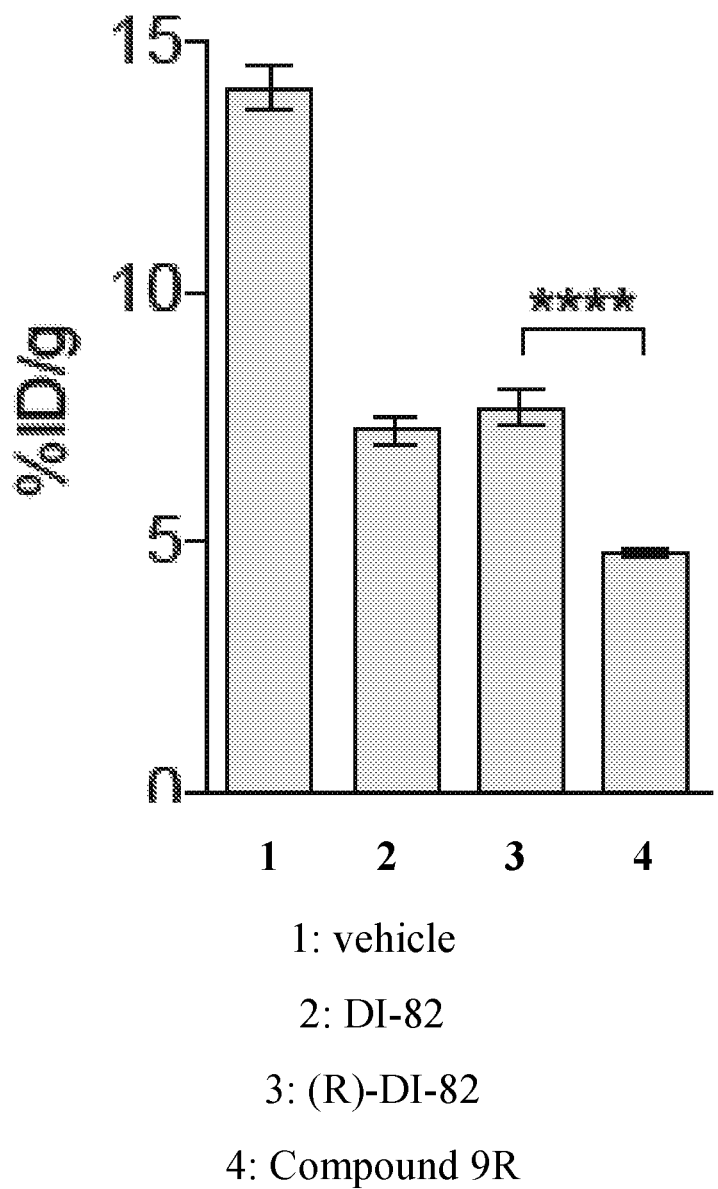
FIG. 8 shows the injected dose/gram of tissue percentages for DI-82, (R)-DI-82, and Compound 9R (IP injection).
Figure 9A:
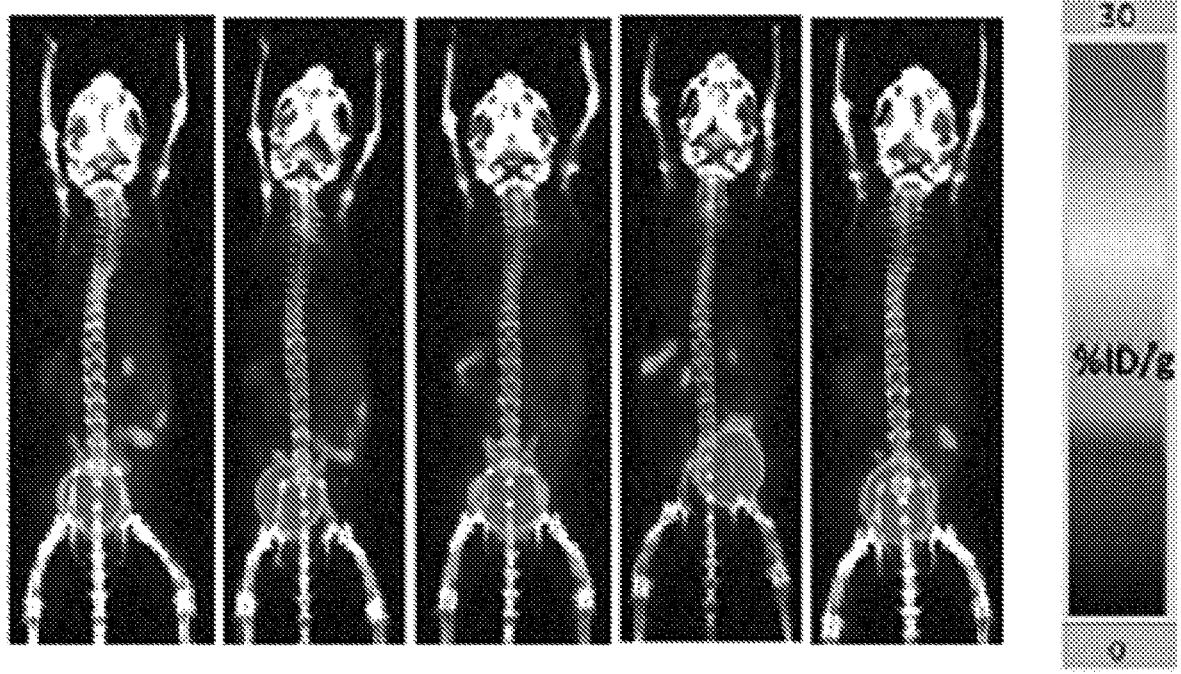
FIG. 9A shows the Compound 9R [$^{18}$F]L-FAC microPET/CT scans (oral dosage, vehicle: P9).
Figure 9B:
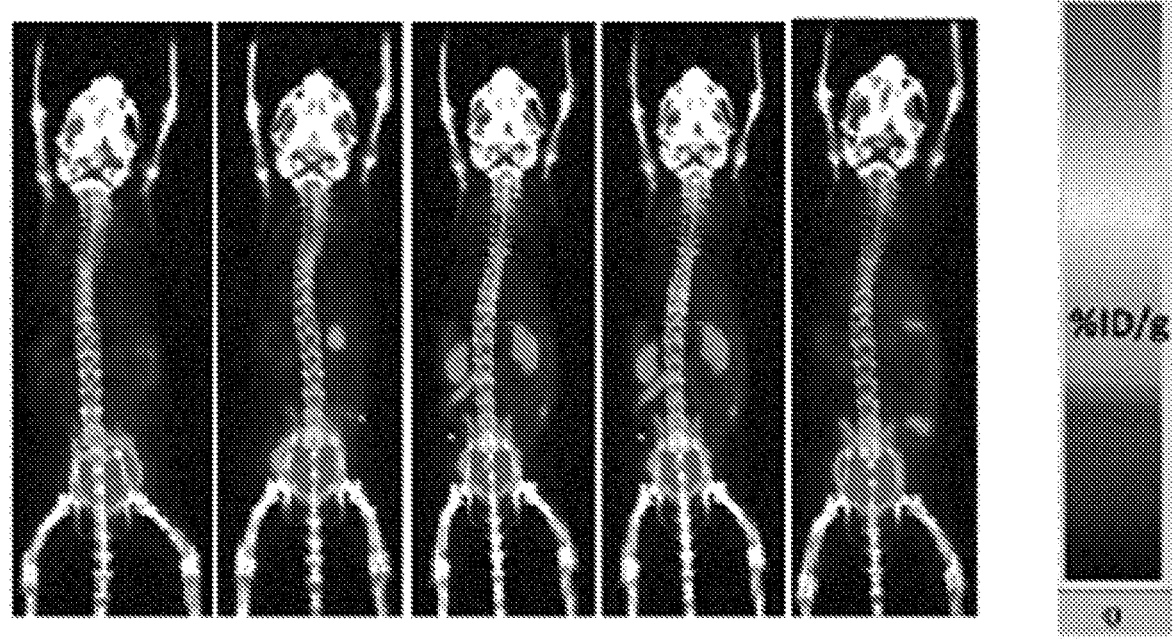
FIG. 9B shows the Compound 9R [$^{18}$F]L-FAC microPET/CT scans (oral dosage, vehicle: P9').
Figure 10A:
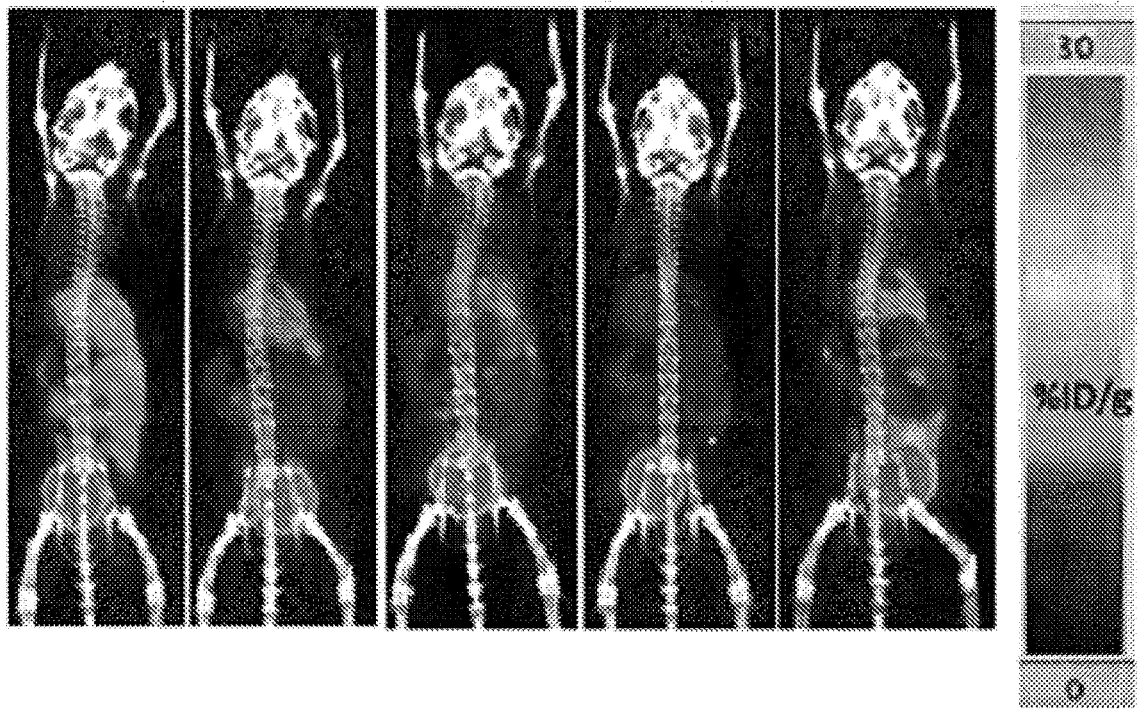
FIG. 10A shows the (R)-DI-82 [$^{18}$F]L-FAC microPET/CT scans (oral dosage, vehicle: P9).
Figure 10B:
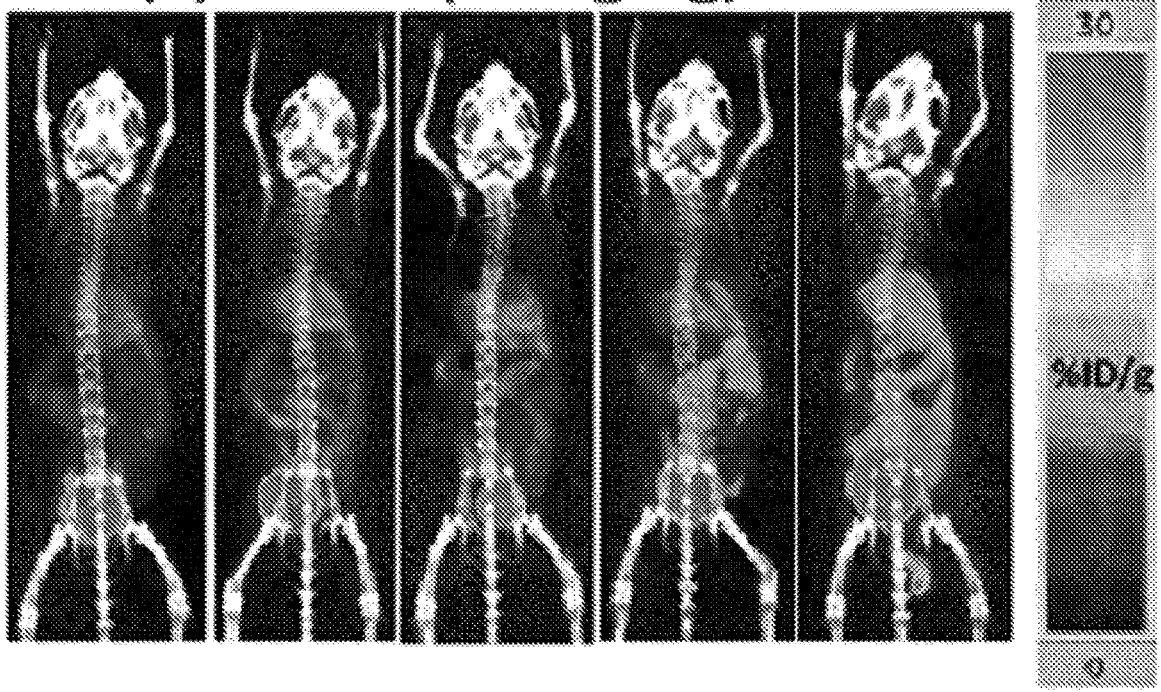
FIG. 10B shows the (R)-DI-82 [$^{18}$F]L-FAC microPET/CT scans (oral dosage, vehicle: P9').
Figure 11:
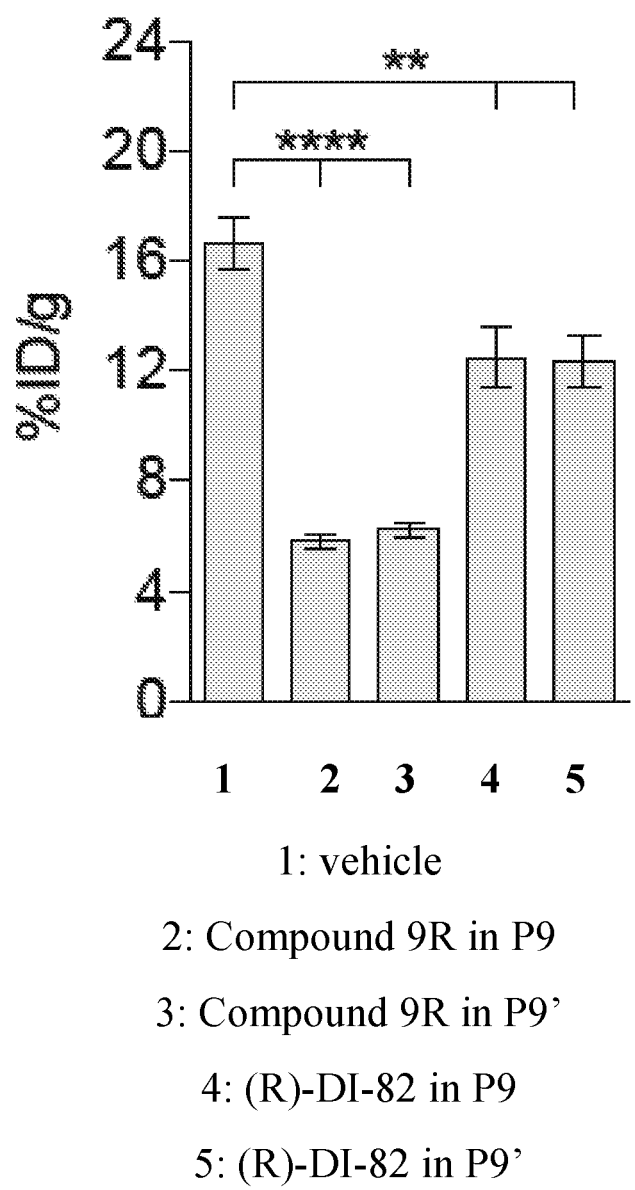
FIG. 11 shows the injected dose/gram of tissue percentages for (R)-DI-82 and Compound 9R (oral dosage) in formulation P9 and P9'.

IP injection: Injection volume 100 μL. (R)-DI-82 and Compound 9R strongly inhibit dCK activity in vivo (see FIG. 6A and FIG. 7). A greater inhibition of dCK was observed with Compound 9R. DI-82 and (R)-DI-82 induced similar inhibition of dCK activity (see FIG. 6A and FIG. 6B). Time-dependent inhibitory effect on the [$^{18}$F]L-FAC was observed with PEG-Tris (vehicle) (see FIG. 5A). The injected dose/gram of tissue percentages for IP dosing are shown in FIG. 8.

Example 8: Pharmacokinetics Profiles

To determine the pharmacokinetic profile of DI-82, (R)-DI-82, compound 9R and compound 6, C57Bl/6 or NSG mice were dosed with the compounds via intraperitoneal injection following the protocol described previously (Murphy, J. M., et al. 2013. Development of new deoxycytidine kinase inhibitors and noninvasive in vivo evaluation using positron emission tomography. J Med Chem. 56:6696-708). Dose formulation include PEG-200: transcutol: labrasol: Tween-80=5:3:1:1 (Prototype 9'). Approximately 75 μL of whole blood was obtained at various time points through retro-orbital sinus bleed using hematocrit capillary tubes.

Plasma Pharmacokinetic study comparing compound 6 and DI-82.

Figure 12:
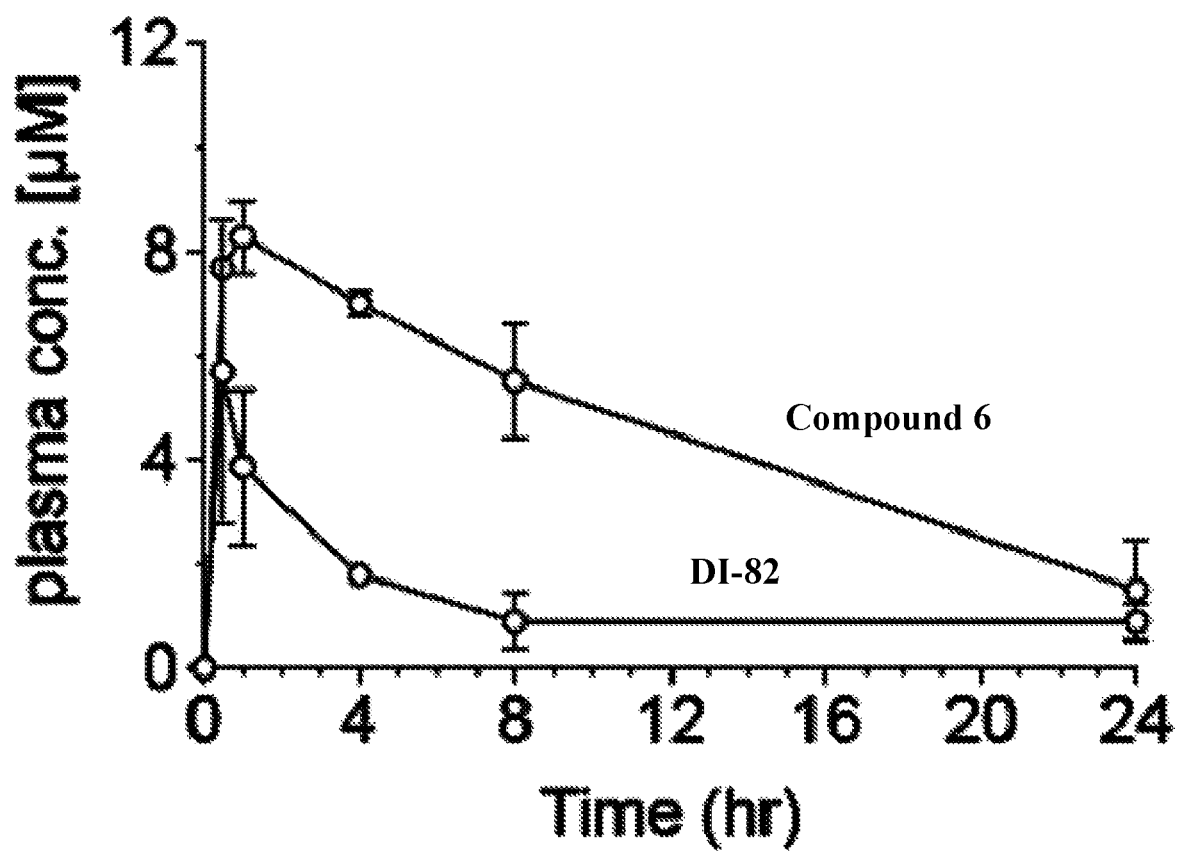
FIG. 12 shows the plasma concentrations of Compound 6 and DI-82.

C57Bl/6 mice (triplicates), 6 months, male, 30 g weight; dose: DI-82 and compound 6: 67 mg/kg; 100 μL. Sample collection: eye bleed at 0.5, 1, 4, 8, and 24 h. The samples were spun down (2000×g) for 15 min. 204 of plasma was collected followed by bioanalytical analysis. The plasma concentration of compound 6 versus DI-82 is shown in FIG. 12.

Plasma Pharmacokinetic study comparing compound 9R and (R)-DI-82.

Figure 14:
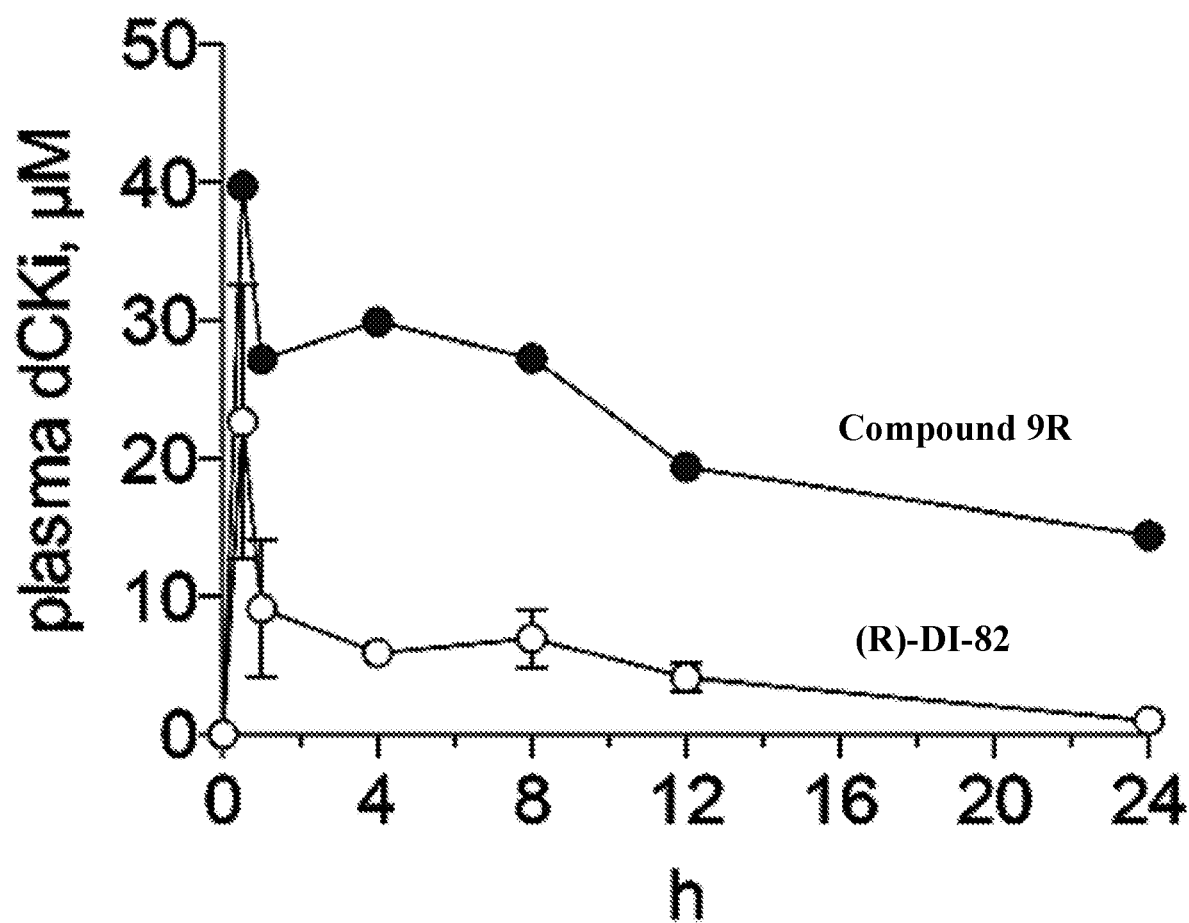
FIG. 14 shows the plasma concentrations of Compound 9R and (R)-DI-82.

C57Bl/6 mice (triplicates), 6 months, male, 30 g weight; dose: (R)-DI-82 and compound 9R: 67 mg/kg; 100 μL. Sample collection: eye bleed at 0.5, 1, 4, 8, and 24 h. The samples were spun down (2000×g) for 15 min. 204 of plasma was collected followed by bioanalytical analysis. The plasma concentration of compound 9R versus (R)-DI-82 is shown in FIG. 14.

Tumor/plasma Pharmacokinetic study comparing compound 6 and DI-82.

Figure 13A:
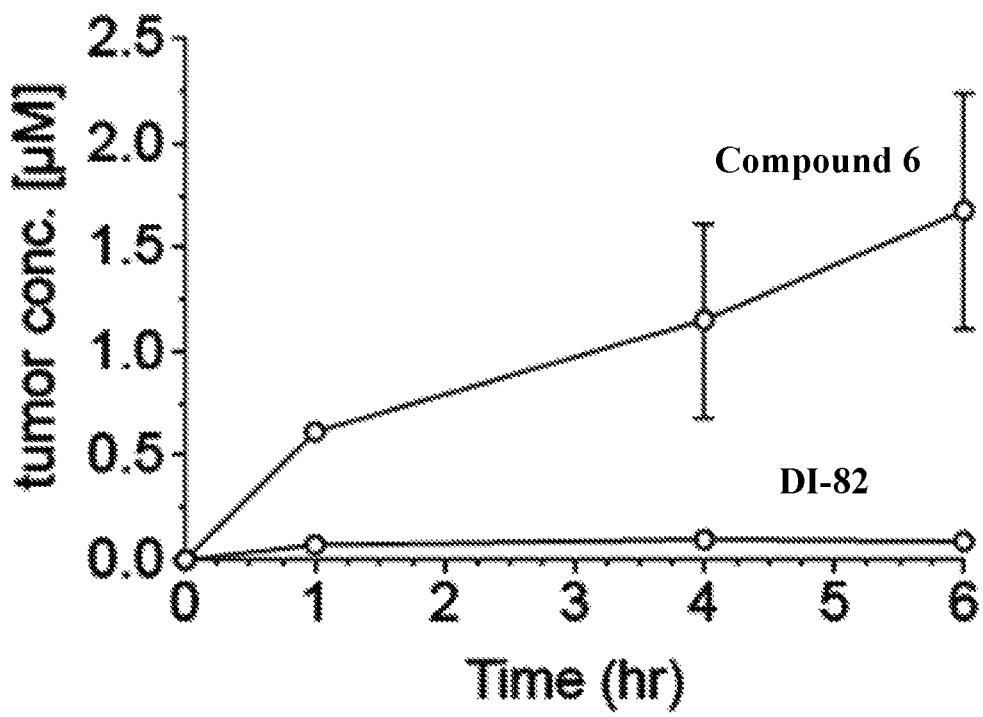
FIG. 13A shows the tumor concentration of Compound 6 and DI-82.
Figure 13B:
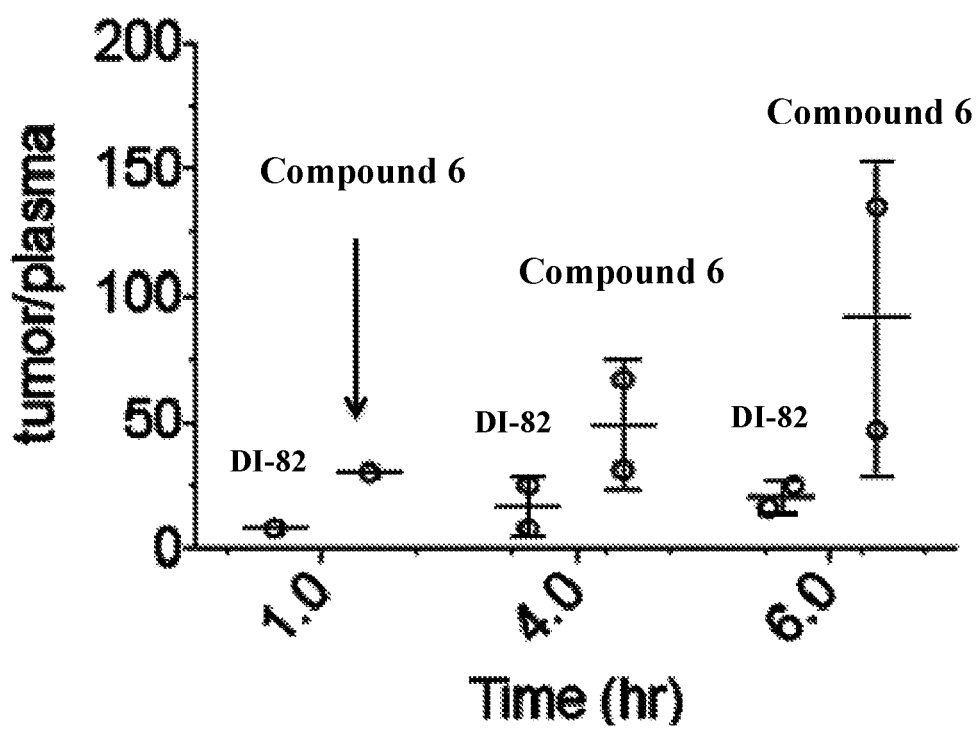
FIG. 13B shows the tumor/plasma ratio of Compound 6 and DI-82.

NSG mice (HEY tumor=ovarian), 2.5 months, female, 20 g weight; dose: DI-82 and Compound 6 were administered together (50 mg/Kg each). Sample collection: eye bleed and extract tumors: 1$^{st}$ mouse (1 h), 2$^{nd}$ and 3$^{rd}$ mouse (4 h), 4$^{th}$ and 5$^{th}$ mouse (6 h). The sample were spun down (2000×g) for 15 min. 204 of plasma was collected followed by bioanalytical analysis. The tumors were weighed and processed. The tumor concentration of compound 6 versus DI-82 is shown in FIG. 13A. FIG. 13B illustrates the ratio of tumor/plasma for DI-82 and Compound 6.

Example 9: Clinical Trial

This is a Phase I, open-label, multicenter, dose-escalation study to investigate the safety, PK and PD of a dCK inhibitor in patients with unresectable primary liver cancer (hepatocellular carcinoma or HCC, excluding HCV-associated HCC) or advanced or metastatic cancer with or without liver involvement. In addition, patients with hematologic malignancies, such as acute lymphocytic leukemia (ALL), lymphoma (including Hodgkin's and non-Hodgkin's lymphoma, B-cell or T-cell), chronic lymphocytic leukemia (CLL), multiple myeloma (MM), myelodysplastic syndrome (MDS) and chronic myeloid leukemia (CML) in accelerated or blast phase, will be accrued. The National Cancer Institute (NCI) Common Terminology Criteria for Adverse Events (CTCAE) version 4.03 will be used for this study to grade AEs. A Cohort Review Committee, CRC-US, will provide oversight over the study for US patients enrolled in US, CRC-K will provide oversight for the South Korean patients, and a CRC-H will provide oversight for patients with hematologic malignancy. The general term "CRC" refers to CRC-US, CRC-K and CRC-H individually or as a group.

For solid tumor patients: the dCK inhibitor will be administered IV twice a week for 3 weeks with 1 week off (total 28 days). A total of 28 days will equal one Cycle. The starting dose for the study is 10 mg/m$^2$ and in no circumstance will any single dose exceed 10 mg/kg (~370 mg/m$^2$). To provide consistency in the number of days between doses, doses will be given twice a week on Monday and Thursday. This schedule will be maintained throughout treatment. Variation of this scheduling to Tuesday and Friday may be accommodated secondary to clinic closures for holidays or patient needs and should be maintained through the duration of that cycle.

For solid tumor patients the study will enter 3 patients per cohort. Dose escalation will be according to a modified Fibonacci dose escalation schema increasing doses at 100%, 67%, 50%, 40%, and then in increments of 33%. At each dose level, if all three patients treated do not develop a DLT subsequent dose escalation will proceed. The observation period for each patient on the cohorts will be determined by the CRC after careful evaluation of all data on patients up to that time. The observation period for DLT determination is Cycle 1 or 28 days.

For all patients, aggressive hydration should be maintained (intravenous hydration, if necessary) after each dose, especially if the patient is experiencing decreased oral fluid intake, nausea, vomiting or diarrhea.

Inclusion/Exclusion Criteria:
Inclusion Criteria
Participating patients must fulfill all of the following criteria:
1. Aged≥18 years.
2. Patients with any of the following malignancies:
Primary liver cancer or hepatocellular carcinoma, histologically, cytologically or radiologically (using triple-phase CT/MRI) confirmed;
Hematologic malignancy; MM and NHL;
Selected solid tumors, including small cell lung cancer (SCLC), non-small cell lung cancer (NSCLC, all histologies), or melanoma, histologically or cytologically confirmed, with or without liver metastasis;
Other cancer types may be enrolled after discussion with and agreement of the Medical Monitor
3. One or more measurable tumors by radiological evaluation; for patients with HCC only, one or more contrast-enhancing measurable tumors in arterial phase of 3-phase contrast CT/MRI. (This eligibility criterion does not apply for the hematologic malignancy patients)
4. Eastern Cooperative Oncology Group (ECOG) performance status≤2.
5. Life expectancy of at least 3 months.
6. Signed, written IRB-approved informed consent.

7. A negative pregnancy test (if female of childbearing potential).

8. Acceptable liver function:

Total bilirubin≤1.5 times the upper limit of normal (ULN).

Aspartate aminotransferase (AST), alanine aminotransferase (ALT) and alkaline phosphatase (ALP)≤5×ULN.

9. Acceptable renal function:

Serum creatinine ≤1.5 times the ULN, or calculated creatinine clearance ≥60 mL/min/1.73 m² for patients with creatinine levels above 1.5 times the institutional ULN.

10. Acceptable hematological status:

Absolute Neutrophil Count (ANC) ≥1500 cells/mm³

Platelet count ≥100,000 plts/mm³ (without transfusion); ≥75,000 plts/mm³ for patients with hepatocellular carcinoma only.

Hemoglobin ≥9 g/dL

For patients with hematologic malignancy of MM, blood count values cited above do not apply.

11. Urinalysis—no clinically significant abnormalities.

12. Acceptable coagulation and albumin status:

Prothrombin time (PT) or International Normalized Ratio (INR)≤1.25×ULN;

for patients with hepatocellular carcinoma only, INR ≤1.7 or prothrombin time (PT) or ≤4 seconds above ULN (i.e., Child-Pugh Score is no greater than 1 for the coagulation parameter)

For patients with HCC only, serum albumin ≥2.8 g/dL (i.e., Child-Pugh Score for albumin is no greater than 2)

For patients with hematologic malignancy, the coagulation and albumin status cited above do not apply 13. Women of childbearing potential and men must agree to use adequate contraception (hormonal or barrier method of birth control or abstinence) prior to study entry and for the duration of study participation including 1 month after the last dose of study drug.

14. For patients with HCC only, Child-Pugh Class A (score 5-6) disease. Score for hepatic encephalopathy must be 1; the score for ascites must be no greater than 2 and clinically irrelevant; for the determination of the Child-Pugh Class.

15. Willingness and ability to comply with scheduled visits, treatment plans, laboratory tests, and other study procedures as specified in the protocol.

Exclusion Criteria

Any of the following will exclude a patient from the study:

1. New York Heart Association (NYHA) Class III or IV cardiac disease, myocardial infarction within the past 6 months, current unstable and/or symptomatic arrhythmia, or evidence of ischemia on ECG.

2. Active, uncontrolled bacterial, viral, or fungal infections requiring systemic therapy. Patients with active hepatitis B infections are eligible if the active infection is controlled with antiviral medications. For the hematologic malignancy patients, active GVHD that has not resolved to Gr 1 or less.

3. Pregnant or nursing women.

NOTE: Women of childbearing potential and men must agree to use adequate contraception (hormonal or barrier method of birth control or abstinence) prior to study entry and for the duration of study participation including for 1 month after the last dose of study drug. Should a woman become pregnant or suspect she is pregnant while participating in this study, she should inform her treating physician immediately.

4. Had major surgery, other than diagnostic surgery, within 4 weeks prior to Cycle 1 Day 1.

5. Patients who had minor surgery within 2 weeks prior to Cycle 1 Day 1 may be enrolled after discussion with the Medical Monitor. Insertion of central line is acceptable at any time prior to enrolment.

6. Treatment with radiation therapy within 4 weeks prior to Cycle 1 Day 1

7. Have received chemotherapy 3 weeks prior to study treatment (6 weeks for nitrosoureas or mitomycin C). Any clinically significant toxicity must have resolved to CTCAE Grade 1 or less. For the hematologic malignancy patients, more recent chemotherapy may be acceptable after discussion with the Medical Monitor.

8. Unwillingness or inability to comply with procedures required in this protocol.

9. Known infection with human immunodeficiency virus (HIV).

10. Serious active nonmalignant disease (e.g., hydronephrosis, liver failure, or other conditions) that could compromise protocol objectives in the opinion of the Investigator and/or the Sponsor.

11. Subjects with central nervous system (CNS) metastases.

12. Currently receiving or having received treatment with any other investigational agent within 4 weeks prior to Cycle 1 Day 1. For the hematologic malignancy patients, more recent treatment with other investigational agents may be acceptable after discussion with the Medical Monitor.

13. Patients with recent history of hemorrhage and patients predisposed to hemorrhage due to coagulopathies or structural anomalies. For the hematologic malignancy patients, these conditions may be acceptable after discussion with the Medical Monitor. In addition, for patients with hematologic malignancy, thrombocytopenia due to disease is acceptable.

14. Patients who require treatment with therapeutic doses of coumarin-type anticoagulants (maximum daily dose of 1 mg allowed for port line patency permitted).

15. Patients with cirrhosis classed as Child-Pugh B or C.

16. Patients receiving amphotericin B or liposomal amphotericin B.

17. Patients for whom dexamethasone is contraindicated.

Treatment Duration:

The schedule will continue as long as there is perceived benefit or until clinically significant disease progression. Clinically significant disease progression should be reviewed with the Medical Monitor. Patients may continue treatment beyond progression after consultation with the Medical Monitor.

The dCK inhibitor dose for the cohorts will be determined by the CRC based on the most current information from both solid tumor and hematologic malignancy cohorts.

Example 10: Acute Myeloid Leukemia Study

In this study, NOD/SCID mice were injected (i.v.) with cells from a human donor diagnosed with AML (IDH2, FLT3-ITD, DNMT3A, and CEBPA mutations identified). Tumor burden was assessed by evaluation of human CD45 positive leukemia cells using FACS. The primary end point was animal survival. Median survival time (MST) and increase in life-span (ILS) were calculated for all animals. The study design is shown in the Table 6.

TABLE 6

| Group | n | Treatment | Dose (mg/kg) | Dose volume (ml/kg) | Dosing Route | Schedule |
|---|---|---|---|---|---|---|
| 1 | 9 | Vehicle | — | 1.5 | po | BID (9 am, 7 pm) x 46 days |
| 2 | 7 | Compound 9R | 25 | 1.5 | po | BID (9 am, 7 pm) x 46 days |
| 3 | 7 | Compound 9R | 50 | 1.5 | po | BID (9 am, 7 pm) x 46 days |
| 4 | 7 | Compound 9R | 100 | 1.5 | po | BID (9 am, 7 pm) x 46 days | n: animal number;
Dosing volume: adjust dosing volume based on body weight (1.5 ml/kg).

The animals were inoculated HUKEMIA® Model AM-7577. The vehicle and treatment injections were started on Day 9 post cell inoculation Day 10 post cell inoculation, respectively.

Weekly Monitoring: Body weight was monitored twice a week. Human leukemia cells was detected by FACS weekly by CD45.

Endpoints and/or Termination: The end points varied according to the tumor burden growth in Vehicle group. The major end point was animal survival. The survival of all animals was followed and median survival time (MST) was calculated for each group. The increase in life-span (ILS) was calculated as follows: ILS (%)=100×[(Median Survival Time of drug treated group/Median Survival Time of vehicle group)−1](%).

Euthanasia: Animals were euthanized by IACUC-approved methods at the time point determined by the endpoints of the study. Animals that were observed to be in a continuing deteriorating condition were euthanized prior to death, or before reaching a comatose state. Animals showing obvious signs of severe distress and/or pain were humanely sacrificed.

Statistical Analysis: Data was evaluated using one way ANOVA. All data was analyzed using Prism 5.0 and IBM SPSS Statistics 19.0. $p<0.05$ was considered to be statistically significant.

Materials and Reagents
Animals
Species: *Mus Musculus*
Strain: NOD/SCID
Age: 3-4 weeks
Sex: Female
Total number for mice order: 39
Animal supplier: HFK Co., Ltd
Animal Batch ID: 20160621F
Animal certificate number: 11401300040888
HUKEMIA® model profile: HUKEMIA® Acute Myeloid Leukemia model AM-7577, Passage: 5 (Frozen)

Animals housing: An acclimation period of approximately one week was allowed between animal receipt and tumor inoculation in order to accustom the animals to the laboratory environment. The mice were maintained in a specific pathogen-free environment and in polysulfone cages (5 mice per cage). All cages, bedding, and water were sterilized before use. Each cage were clearly labeled with a cage card indicating number of animals, sex, strain, date received, treatment, study number, group number, and the starting date of the treatment. The cages with food and water were changed twice a week. The targeted conditions for animal room environment and photoperiod were as follows:
Temperature 20~26° C.
Humidity 30~70%
Light cycle 12 hours light and 12 hours dark Dietary Materials: All animals had free access to a standard certified commercial laboratory diet. Maximum allowable concentrations of contaminants in the diet were controlled and routinely analyzed by the manufacturers. Autoclaved municipal tap water, suitable for human consumption was available to the animals ad libitum.

The Test Article Formulation Preparation is as described in Table 7.

TABLE 7

| Treatment | Vehicle solution | Concentration | Storage |
|---|---|---|---|
| Vehicle | PEG 200:Transcutol ® HP (Gattefosse):Labrasol:Tween 20 (50:30:10:10 v/v/v/v) | — | RT |
| Compound 9R | PEG-200:Transcutol:Labrasol:Tween-20 = 50:30:10:10 v/v/v/v | 16.67 mg/ml 33.33 mg/ml 66.67 mg/ml | RT |

II.
Results and Summary
Tumor Burden Growth

Figure 15:
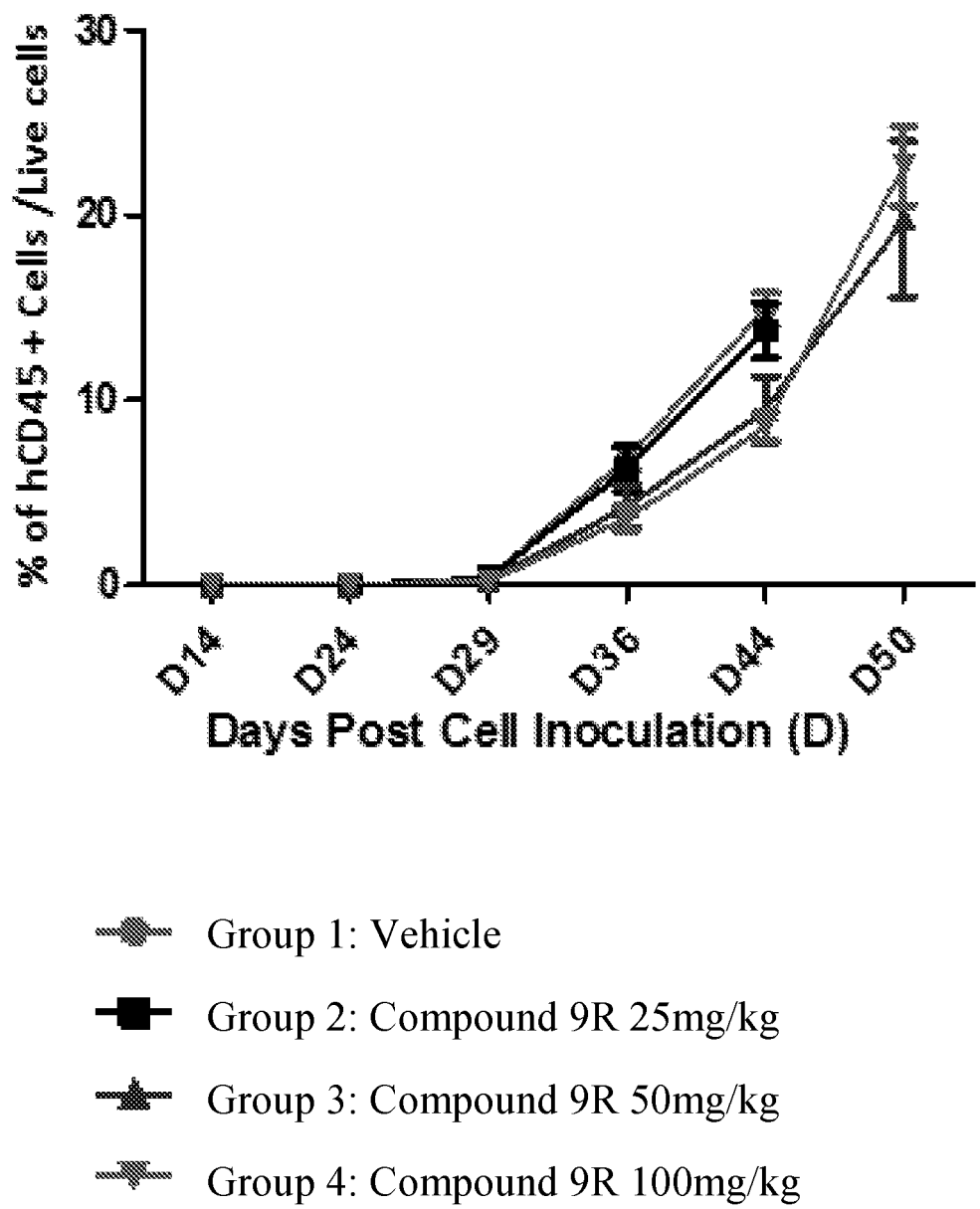
FIG. 15 shows the tumor burden growth curve following treatment with vehicle and Compound 9R (25, 50, and 100 mg/kg).

The tumor burden growth was analyzed by FACS with human CD45 and is shown in FIG. 15 (Note: Mean±SEM was calculated only when there are 80% or more animals (at least 6 animals per each cohort) on the study for each time point). The vehicle group showed significant increase for tumor burden post cells inoculation day 29. The tumor burden in Compound 9R (25 mg/Kg) treatment group also showed significant increase post cells inoculation day 29. The tumor burden in Compound 9R (50 mg/Kg) and Compound 9R (100 mg/Kg) treatment groups showed slowly increased during Day 29 to Day 44 post cell inoculation, then significant increase and end at Day55 post cell inoculation.

Figure 16:
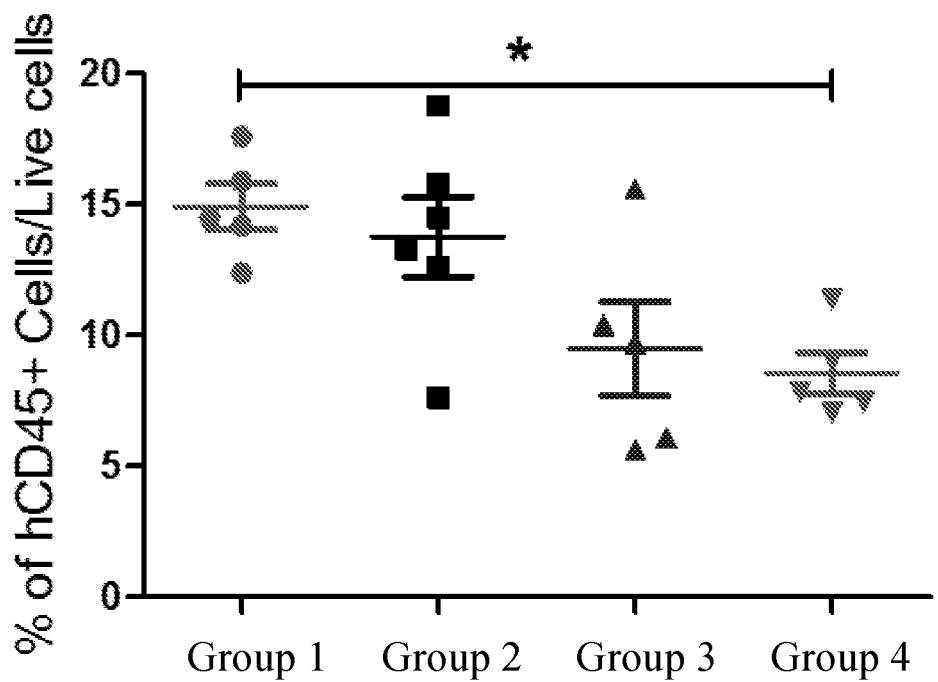
FIG. 16 shows the tumor burden in peripheral blood following treatment with vehicle and Compound 9R (25, 50, and 100 mg/kg) at Day 44 post inoculation

Tumor Growth Inhibition
Tumor Burden Scatter of Mice in Peripheral Blood at Day 44 post cell inoculation is shown in FIG. 16. The tumor burden (human CD45 positive leukemia cells) in PB for each group were analyzed by statistical software SPSS at day 44 post cell inoculation. Mice in Compound 9R 100 mg/kg treated group showed significant antitumor effects compared with vehicle treatment group (p=0.021).

Figure 17:
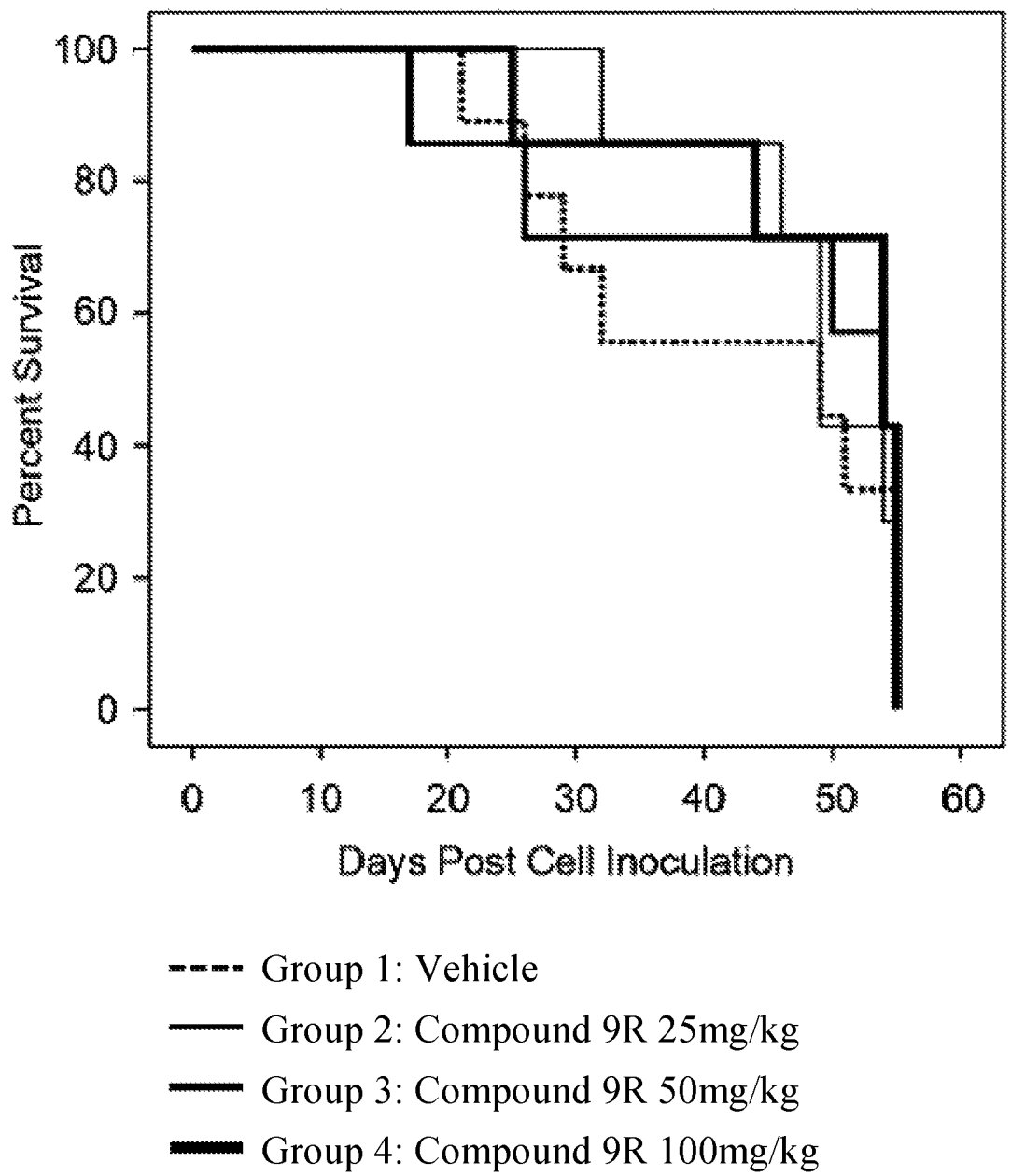
FIG. 17 shows the survival curves following treatment with vehicle and Compound 9R (25, 50, and 100 mg/kg).

Animal Survival
The survival curves of 4 groups of mice are shown in FIG. 17. The median survival of groups 1-4 was 49, 49, 54 and 54 days, respectively. The corresponding ILS (increase in lifespan) as compared with Group 1 for groups 2-4 were 0%, 10% and 10%, respectively, and their P value were 0.775, 0.656 and 0.458, respectively, as shown in Table 8.

TABLE 8

| Group | Treatment | Median survival (day) | ILS (%) | P value |
|---|---|---|---|---|
| 1 | Vehicle | 49 | — | — |
| 2 | Compound 9R 25 mg/kg | 49 | 0 | >0.05 |
| 3 | Compound 9R 50 mg/kg | 54 | 10 | >0.05 |
| 4 | Compound 9R 100 mg/kg | 54 | 10 | >0.05 |

Example 11: Acute Lymphoblastic Leukemia (ALL) Model

The efficacy of Compound 9R and (R)-DI-82 single agent therapy against short-term cultures of murine BCR-ABL (p185), Arf$^{-/-}$ pre-B ALL cells (p185$^{BCR-ABL}$/Arf$^{-/-}$) was assessed. This assay was previously described in Boulos, N. et al., 2011. "Chemotherapeutic agents circumvent emergence of dasatinib-resistant BCR-ABL kinase mutations in a precise mouse model of Philadelphia chromosome-positive acute lymphoblastic leukemia, Blood, 117:3585-3595 and Nathanson, D. 2014 "Co-targeting of convergent nucleotide biosynthetic pathways for leukemia eradication" J. Exp. Med. 211(3): 473-486, all of which are incorporated herein by reference.

Bioluminescent imaging and data analysis were performed using a Xenogen IVIS-200 system and Living Image Version 3.01 software (Caliper Life Sciences). Mice were injected intraperitoneally with D-luciferin (Caliper Life Sciences) at 100 mg/kg body weight and, after 3-5 minutes to allow substrate distribution, anesthetized for imaging using 2% isoflurane delivered at 2 L/min in $O_2$. Images were acquired using 1-minute exposures with small binning and with shortening of exposure times when signals were saturated. Total flux measurements (photons/second) were quantified over the whole-animal body or a contour drawn around a target organ. Images were normalized to the same color scale by setting maximum signal of luminescent activity to 1×10$^6$ photons/second/cm$^2$/steradian (sr).

Figure 18A:
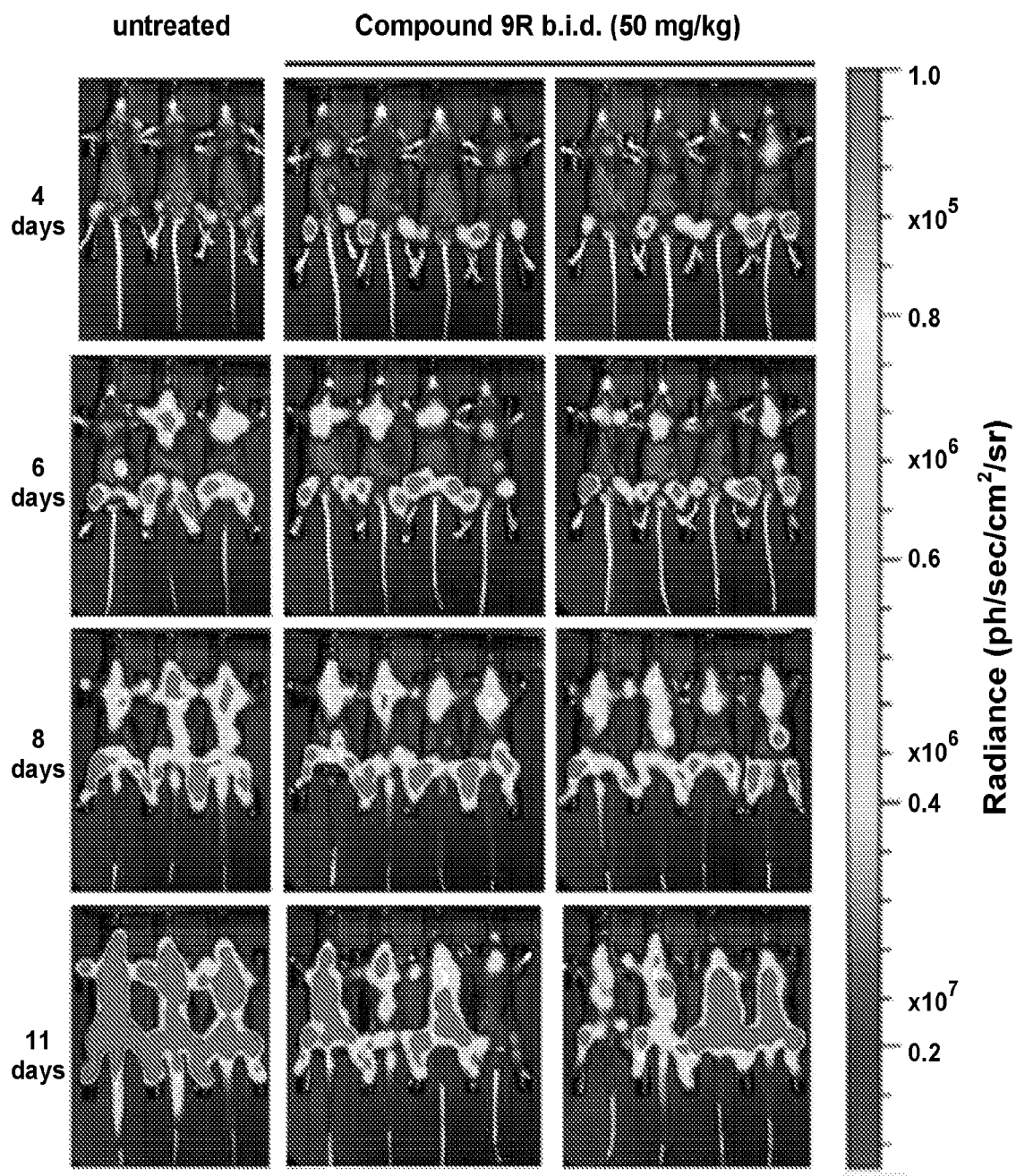
FIG. 18A shows the bioluminescence imagings of mice treated with Compound 9R (50 mg/kg) as compared with untreated mice at day 4, 6, 8, and 11 after intravenous injection of $2.0 \times 10^4$ pre-B leukemia cells/mouse.
Figure 18B:
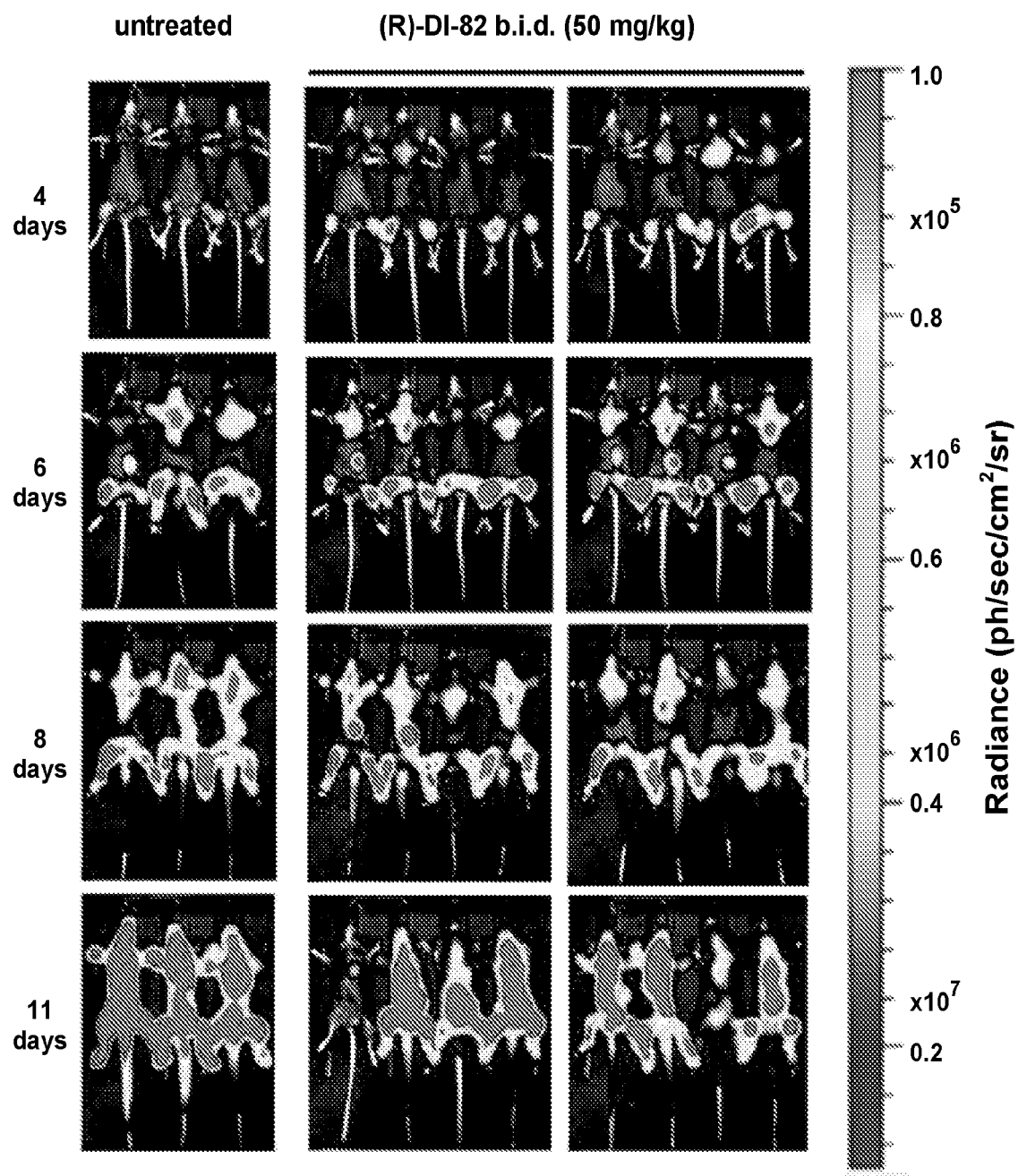
FIG. 18B shows the bioluminescence imagings of mice treated with (R)-DI-82 (50 mg/kg) as compared with untreated mice at day 4, 6, 8, and 11 after intravenous injection of $2.0 \times 10^4$ pre-B leukemia cells/mouse.
Figure 19:
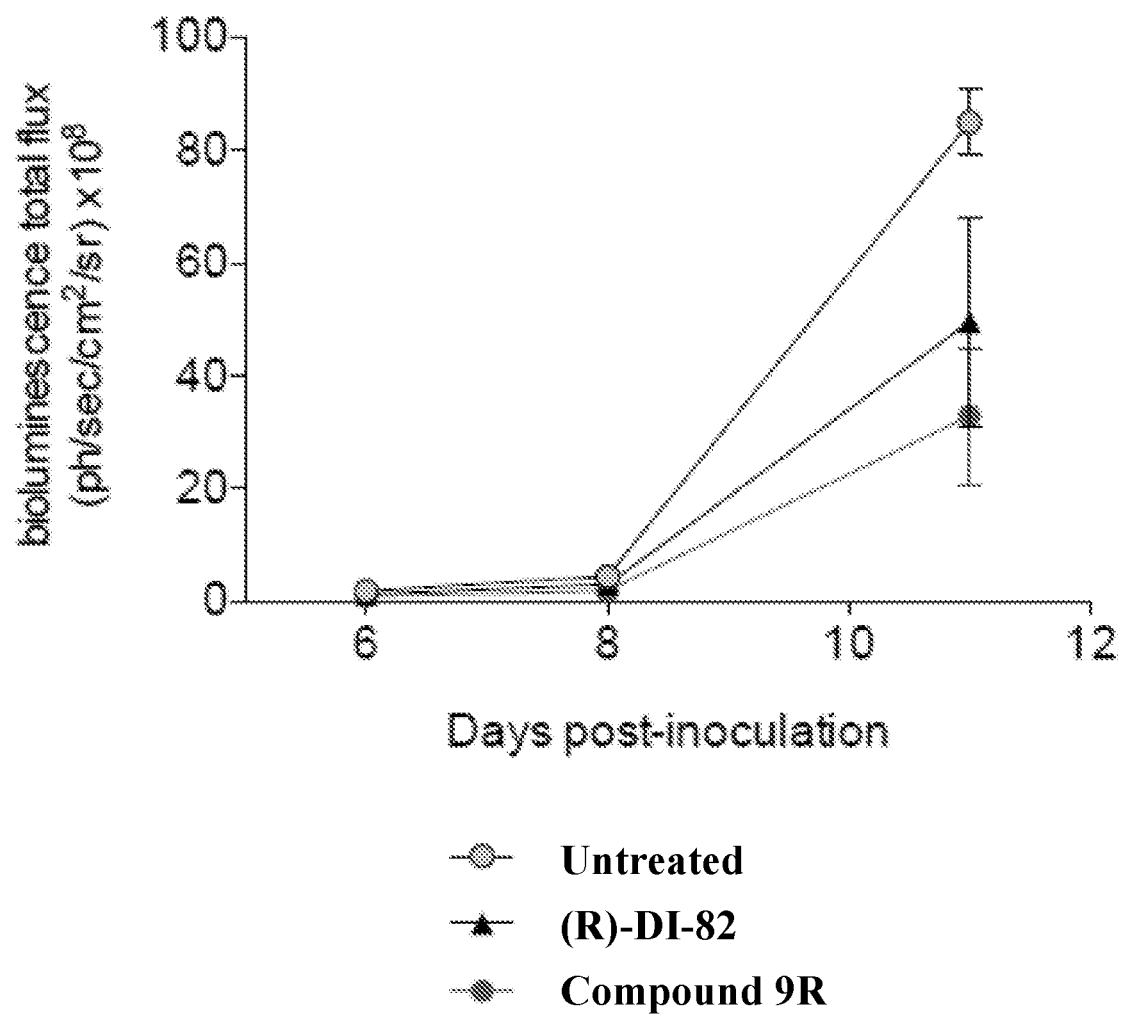
FIG. 19 shows the bioluminescence total flux over day 4, 6, 8, and 11 post inoculation of mice treated with (R)-DI-82 (50 mg/kg) and Compound 9R (50 mg/kg) as compared with untreated mice.
Figure 20:
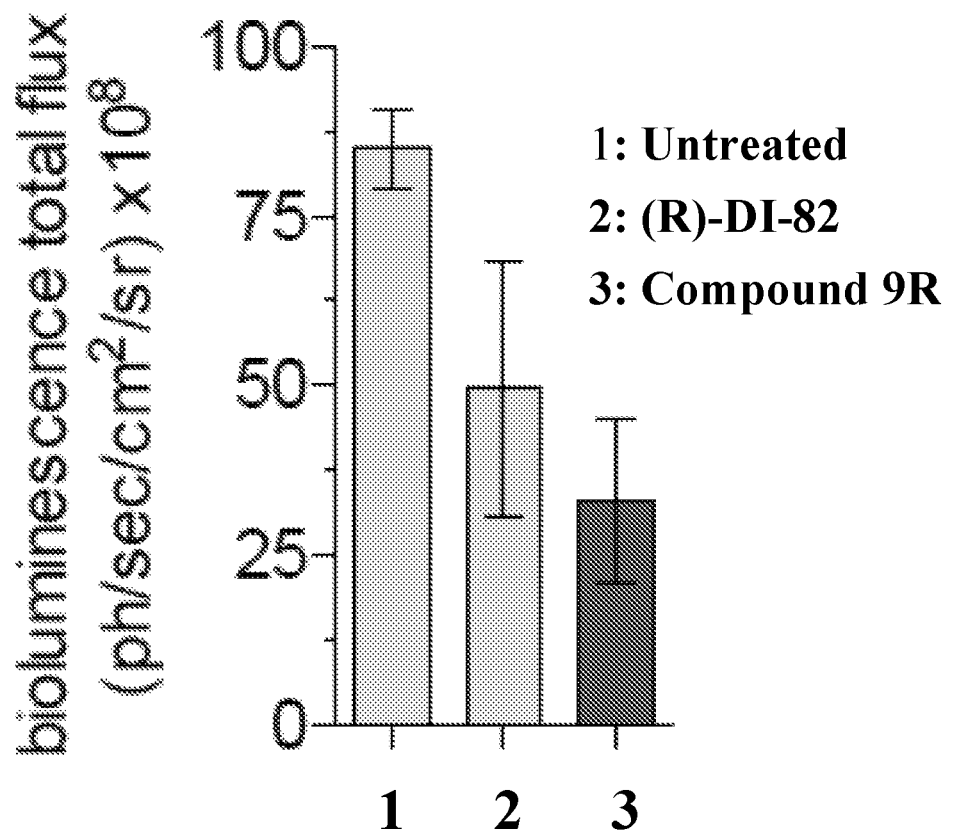
FIG. 20 shows the bioluminescence total flux at day 11 post inoculation of mice treated with (R)-DI-82 (50 mg/kg) and Compound 9R (50 mg/kg) as compared with untreated mice.

To evaluate the efficacy of Compound 9R and (R)-DI-82 in an in vivo B-ALL model, firefly luciferase—marked p185$^{BCR-ABL}$/Arf$^{-/-}$ cells were inoculated intravenously in NSG mice. 4 days, 6 days, 8 days and 11 days after inoculation, bioluminescence imaging (BLI) of firefly luciferase-marked p185$^{BCR-ABL}$/Arf$^{-/-}$ ALL-bearing NSG mice treated with 50 mg/kg compound 9R or 50 mg/kg (R)-DI-82 were measured. Results comparing compound 9R and untreated animal are shown in FIG. 18A. Results comparing (R)-DI-82 and untreated animal are shown in FIG. 18B. The bioluminescence total flux comparison are shown in FIG. 19 and FIG. 20 (day 11 post inoculation). Both compound 9 and (R)-DI-82 show efficacy in the p185$^{BCR-ABL}$/Arf$^{-/-}$ ALL model.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A compound of Formula (I), or a pharmaceutically acceptable salt or solvate thereof:

A.

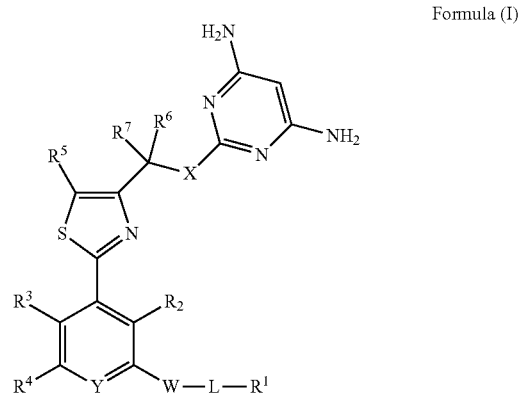

Formula (I)

wherein:
W is —O—, —S—, or —N(R$^8$)—;
L is optionally substituted alkylene, optionally substituted alkenylene, or optionally substituted alkynylene;
X is —CH$_2$—, —O—, —N(R$^8$)—, —S—, —S(O)—, or —S(O)$_2$—;
Y is N or C(R$^9$);
R$^1$ is optionally substituted heterocycloalkyl;
R$^2$, R$^3$, R$^4$ are independently hydrogen, halogen, —CN, —N$_3$, —CF$_3$, —CCl$_3$, —CBr$_3$, —Cl$_3$, —CN, —C(O)H, —OH, —NH$_2$, —C(O)OH, —C(O)NH$_2$, —NO$_2$, —SH, optionally substituted alkyl, optionally substituted heteroalkyl, optionally substituted heterocycloalkyl, optionally substituted aryl, optionally substituted heteroaryl, optionally substituted alkoxy, or optionally substituted cycloalkyl;
R$^5$ is hydrogen, halogen, —CN, —N$_3$, —CF$_3$, —CCl$_3$, —CBr$_3$, —Cl$_3$, —CN, —C(O)H, —OH, —NH$_2$, —C(O)OH, —C(O)NH$_2$, —NO$_2$, —SH, optionally substituted alkyl, optionally substituted heteroalkyl, optionally substituted heterocycloalkyl, optionally substituted alkoxy, optionally substituted cycloalkyl, optionally substituted aryl, or optionally substituted heteroaryl;
R$^6$ and R$^7$ are independently hydrogen, halogen, or optionally substituted alkyl; or
R$^6$ and R$^7$ are taken together with the carbon to which they are attached to form a cycloalkyl;
R$^8$ is hydrogen or optionally substituted alkyl; and
R$^9$ is hydrogen, halogen, —CN, —N$_3$, —CF$_3$, —CCl$_3$, —CBr$_3$, —Cl$_3$, —CN, —C(O)H, —OH, —NH$_2$, —C(O)OH, —C(O)NH$_2$, —NO$_2$, —SH, optionally substituted alkyl, optionally substituted heteroalkyl, optionally substituted heterocycloalkyl, optionally substituted aryl, optionally substituted heteroaryl, optionally substituted alkoxy, or optionally substituted cycloalkyl.

2. The compound of claim 1, wherein R$^2$ and R$^3$ are hydrogen.

3. The compound of claim 1, wherein R$^4$ is hydrogen or halogen.

4. The compound of claim 1, wherein R$^6$ and R$^7$ are independently hydrogen or optionally substituted alkyl.

5. The compound of claim 1, wherein R$^7$ is hydrogen.

6. The compound of claim 5, wherein the compound of Formula (I) is a compound of Formula (Ia):

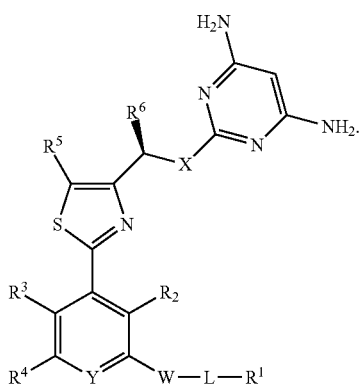

Formula (Ia)

7. The compound of claim 5, wherein the compound of Formula (I) is a compound of Formula (Ib):

B.

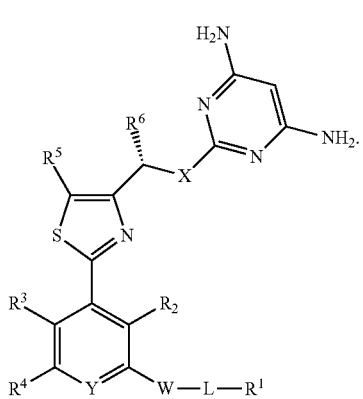

Formula (Ib)

8. The compound of claim 1, wherein $R^5$ is optionally substituted alkyl.

9. The compound of claim 1, wherein X is —S— or —CH$_2$—.

10. The compound of claim 1, wherein Y is N or C($R^9$).

11. The compound of claim 10, wherein $R^9$ is hydrogen, optionally substituted alkyl, or optionally substituted alkoxy.

12. The compound of claim 1, wherein W is —O—.

13. The compound of claim 1, wherein L is optionally substituted alkylene.

14. The compound of claim 1, wherein $R^1$ is a 5-membered or a 6-membered optionally substituted heterocycloalkyl.

15. The compound of claim 1, wherein $R^1$ is pyrrolidinyl, piperidinyl, piperizanyl, or morpholinyl.

16. The compound of any one of claims 1-3, 4-7, 8, 9, 10, 11, 12, 13, 14, and 15, wherein the compound of Formula (I) is selected from:

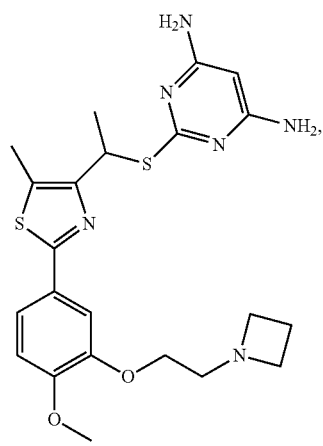

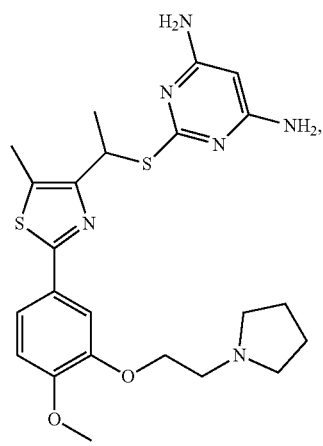

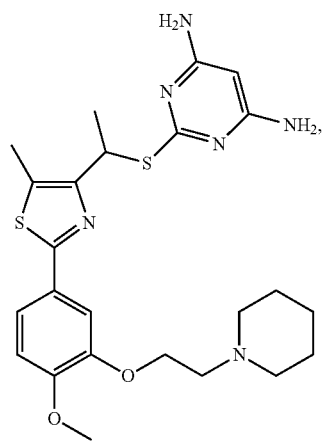

143
-continued
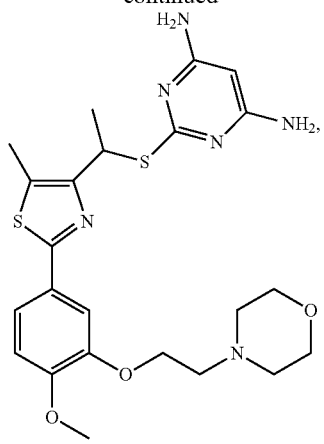
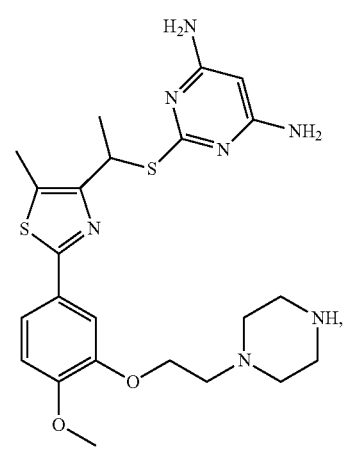
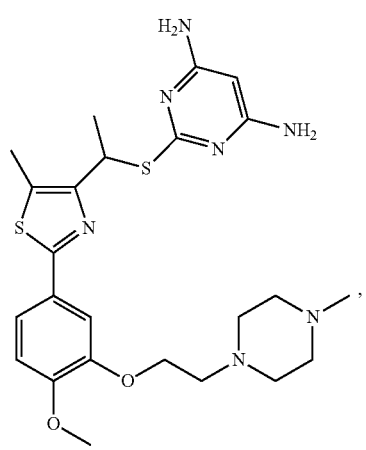
144
-continued
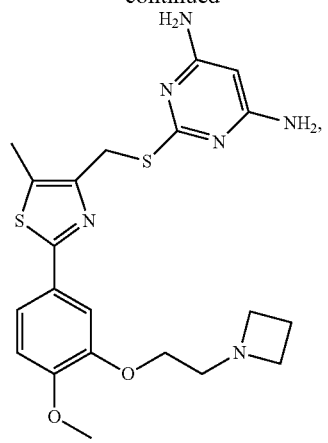
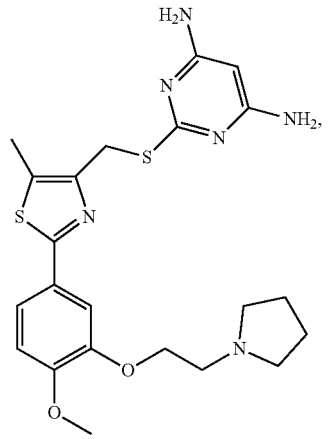

145
-continued
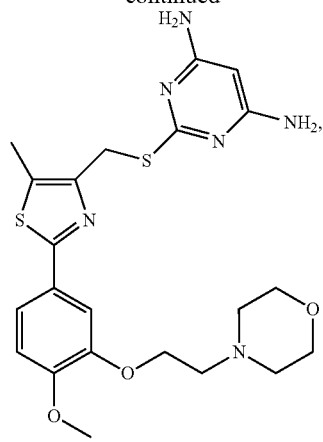
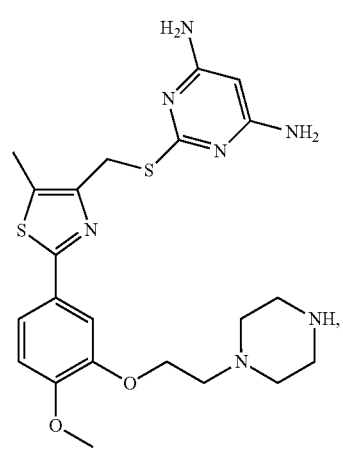
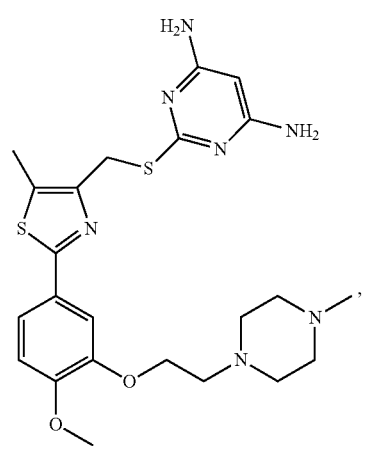
146
-continued
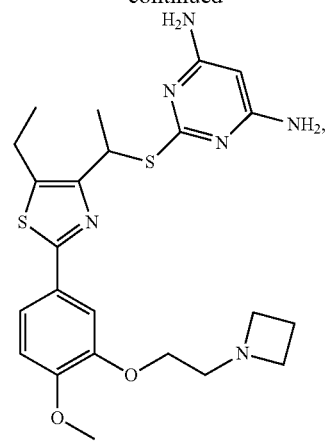
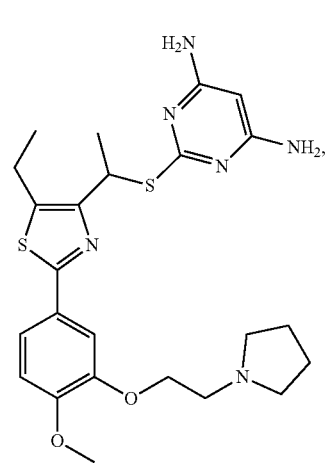
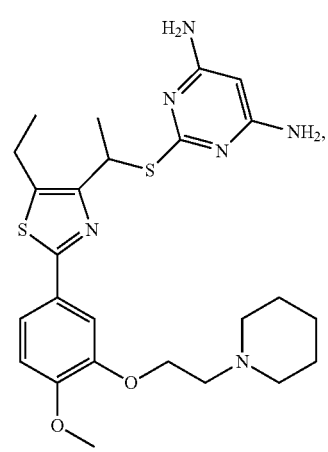

147
-continued
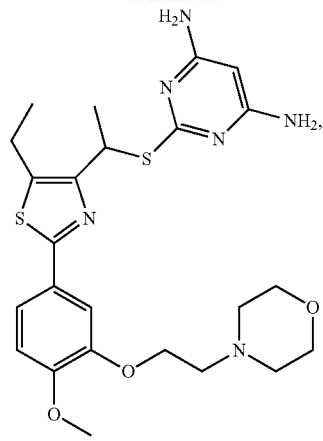
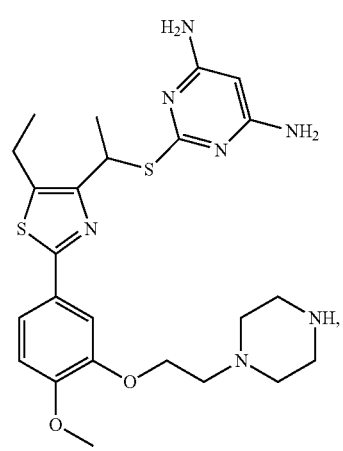
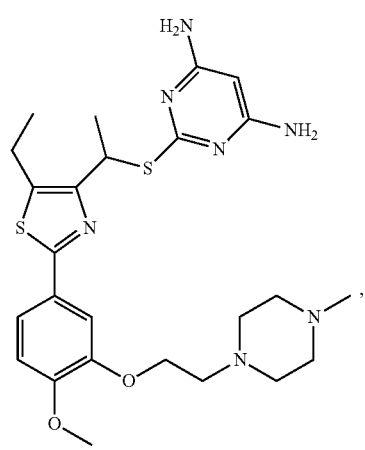
148
-continued
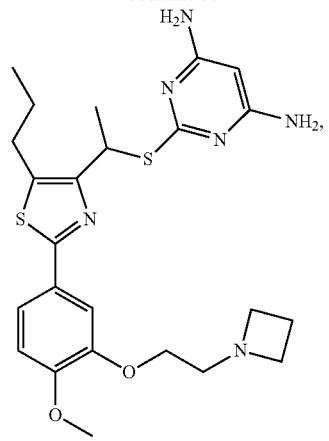
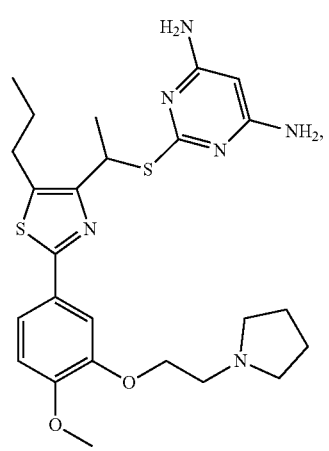
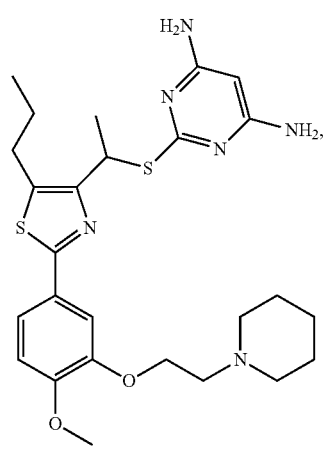

-continued
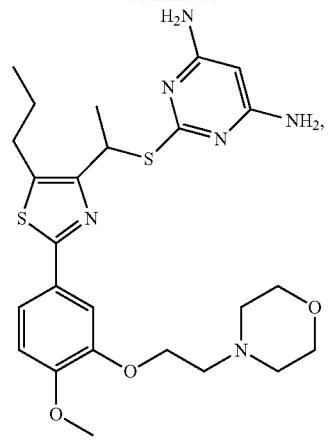
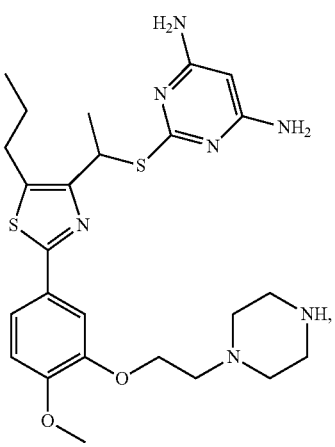
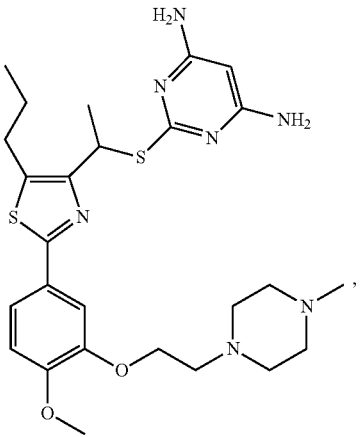
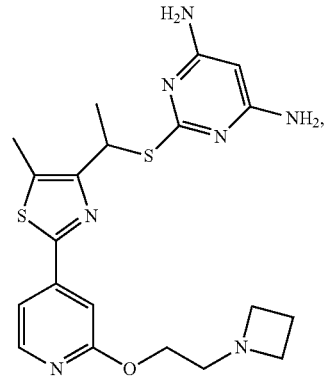
-continued
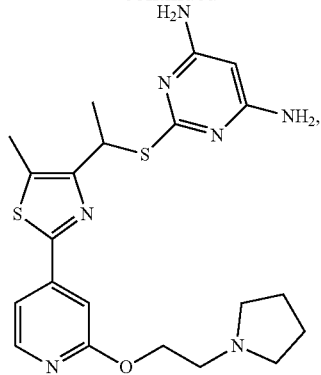
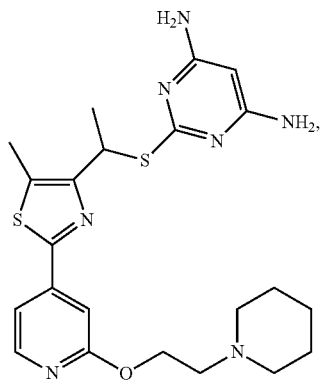
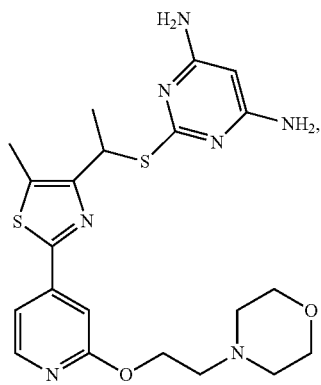
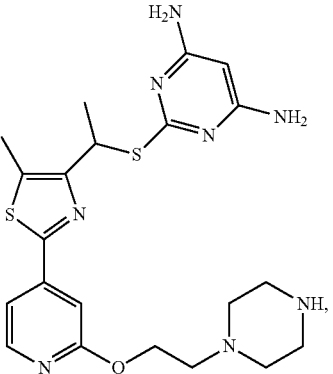

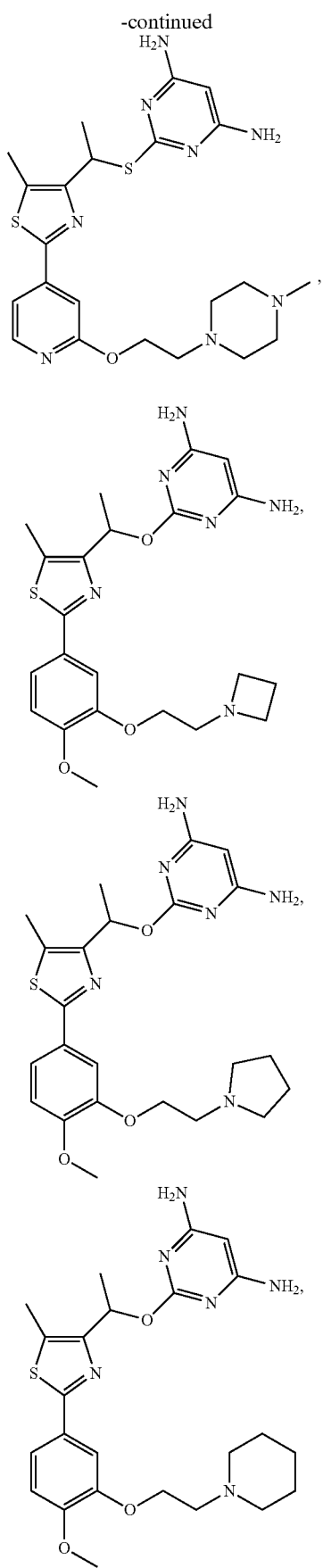

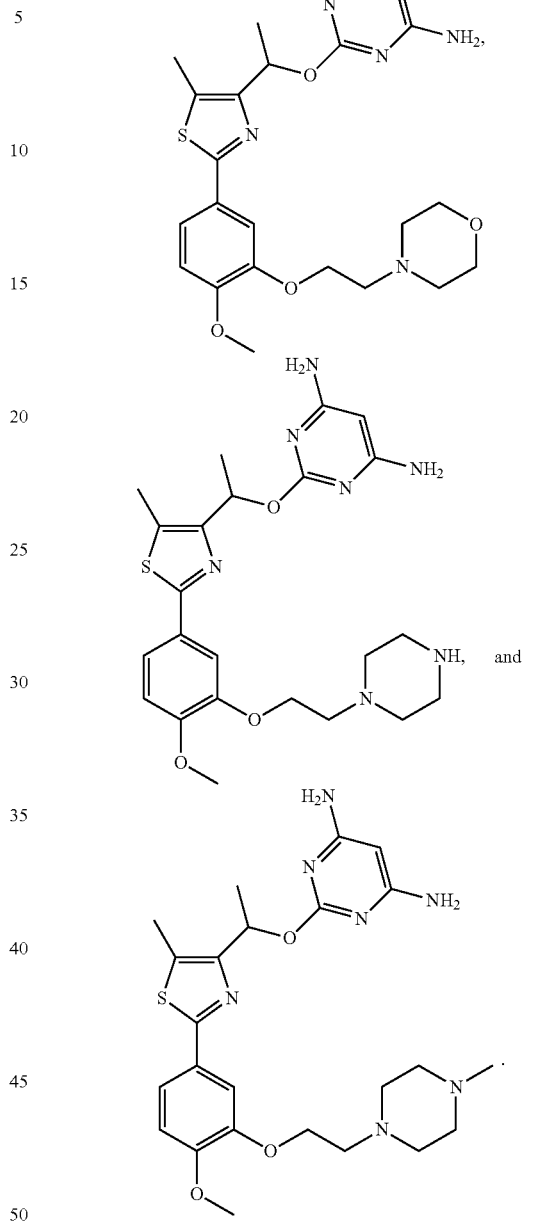

17. The compound of claim 1, wherein
W is —O—, —S—, or —N(R$^8$)—;
L is optionally substituted alkylene, optionally substituted alkenylene, or optionally substituted alkynylene;
X is —CH$_2$—, —O—, —N(R$^8$)—, —S—, —S(O)—, or —S(O)$_2$—;
Y is N or C(R$^9$);
R$^1$ is optionally substituted heterocycloalkyl;
R$^2$, R$^3$, R$^4$ are independently hydrogen, halogen, —CN, optionally substituted alkyl, optionally substituted alkoxy, or optionally substituted cycloalkyl;
R$^5$ is hydrogen, halogen, optionally substituted alkyl, optionally substituted alkoxy, optionally substituted cycloalkyl, optionally substituted aryl, or optionally substituted heteroaryl;

$R^6$ and $R^7$ are independently hydrogen, halogen, or optionally substituted alkyl; or $R^6$ and $R^7$ are taken together with the carbon to which they are attached to form a cycloalkyl;

$R^8$ is hydrogen or optionally substituted alkyl; and $R^9$ is hydrogen, halogen, —CN, optionally substituted alkyl, optionally substituted alkoxy, or optionally substituted cycloalkyl.

18. A pharmaceutical composition, comprising a compound of claim 1 or a pharmaceutically acceptable salt or solvate thereof, and a pharmaceutically acceptable excipient.

19. A method for inhibiting a deoxycytidine kinase (dCK) activity, comprising contacting a deoxycytidine kinase with an effective amount of the compound of claim 1, thereby inhibiting the deoxycytidine kinase.

20. A method of treating leukemia in a subject in need thereof, comprising administering to the subject an effective amount of the compound of claim 1.

21. A method of treating leukemia in a subject in need thereof, comprising administering to the subject a pharmaceutical composition of claim 18.

22. The method of claim 20, wherein the leukemia is acute myeloid leukemia or acute lymphoblastic leukemia.

23. The method of claim 21, wherein the leukemia is acute myeloid leukemia or acute lymphoblastic leukemia.

* * * * *